United States Patent
Pfeifer et al.

(10) Patent No.: US 11,103,568 B2
(45) Date of Patent: Aug. 31, 2021

(54) PNEUMOCOCCAL VACCINE FORMULATIONS

(71) Applicant: The Research Foundation for The State University of New York, Amherst, NY (US)

(72) Inventors: Blaine Pfeifer, Buffalo, NY (US); Charles Jones, North Tonawanda, NY (US); Jonathan Lovell, Niagara Falls (CA)

(73) Assignee: The Research Foundation for The State University of New York, Amherst, NY (US)

( * ) Notice: Subject to any disclaimer, the term of this patent is extended or adjusted under 35 U.S.C. 154(b) by 13 days.

(21) Appl. No.: 16/091,032

(22) PCT Filed: Apr. 5, 2017

(86) PCT No.: PCT/US2017/026060
§ 371 (c)(1),
(2) Date: Oct. 3, 2018

(87) PCT Pub. No.: WO2017/176833
PCT Pub. Date: Oct. 12, 2017

(65) Prior Publication Data
US 2019/0307873 A1    Oct. 10, 2019

Related U.S. Application Data

(60) Provisional application No. 62/318,514, filed on Apr. 5, 2016.

(51) Int. Cl.
*A61K 39/09* (2006.01)
*A61P 31/04* (2006.01)
(Continued)

(52) U.S. Cl.
CPC .......... *A61K 39/092* (2013.01); *A61K 9/1271* (2013.01); *A61P 31/04* (2018.01);
(Continued)

(58) Field of Classification Search
CPC ........ A61P 11/00; A61P 31/04; A61K 39/092; A61K 2039/55555; A61K 2039/55505;
(Continued)

(56) References Cited

U.S. PATENT DOCUMENTS 6,699,703 B1 *   3/2004   Doucette-Stamm .........................
                                                     A61K 31/7052
                                                         435/252.3
2004/0146486 A1   7/2004  Sun
(Continued)

FOREIGN PATENT DOCUMENTS

WO    2006/084467 A1    8/2006
WO    2009/059054 A2    5/2009
(Continued)

OTHER PUBLICATIONS

Shao, S., et al., Functionalization of cobalt porphyrin-phospholipid bilayers with his-tagged ligands and antigens, Nature Chemistry, Apr. 20, 2015, vol. 7, No. 5, pp. 438-446.
(Continued)

*Primary Examiner* — Jana A Hines
(74) *Attorney, Agent, or Firm* — Hodgson Russ LLP

(57) ABSTRACT

Immunogenic composition are provided comprising PnCo and/or GlpO polypeptides identified as being preferentially expressed during the virulent phase of an infection related to streptococcal bacteria. The compositions can be used for eliciting immune response against streptococcal infections, such as against infections caused by *S. pneumoniae*.

10 Claims, 48 Drawing Sheets

Specification includes a Sequence Listing.

(51) Int. Cl.
*A61K 9/127* (2006.01)
*A61K 39/00* (2006.01)

(52) U.S. Cl.
CPC .............. *A61K 2039/55505* (2013.01); *A61K 2039/55555* (2013.01); *A61K 2039/55566* (2013.01)

(58) Field of Classification Search
CPC ........ A61K 47/544; A61K 2039/55566; A61K 9/1271
See application file for complete search history.

(56) References Cited

U.S. PATENT DOCUMENTS

| | | |
|---|---|---|
| 2008/0009035 A1 | 1/2008 | Doucette-Stamm et al. |
| 2010/0183596 A1 | 7/2010 | Bootsma et al. |

FOREIGN PATENT DOCUMENTS

| | | | |
|---|---|---|---|
| WO | 2010/150242 A2 | 12/2010 | |
| WO | 2013/040648 A1 | 3/2013 | |
| WO | WO-2016168817 A1 * | 10/2016 | ............. A61K 9/127 |

OTHER PUBLICATIONS

Reeck, G.R., et al., "Homology" in Proteins and Nucleic Acids: A Terminology Muddle and a Way out of it, Cell, Jan. 1, 1987, vol. 50, p. 667.

Saxena, S., et al., Additive impact of pneumococcal conjugate vaccines on pneumonia and empyema hospital admissions in England, Journal of Infection, Jul. 6, 2015, vol. 71, No. 4, pp. 428-436.

Kim, E., et al., The effect of ionic strength and hardness of water on the non-ionic surfactant-enhanced remediation of perchloroethylene contamination, Journal of Hazardous Materials, Mar. 17, 2005, vol. 119, No. 1-3, pp. 195-203.

UNIPROT, Database accession No. A7XHI4, Oct. 23, 2007, CPBP family intramembrane metalloprotease, 3 pages.

Lux, T., et al., Diversity of Bacteriocins and Activity Spectrum in *Streptococcus pneumoniae*, Journal of Bacteriology, Aug. 17, 2007, vol. 189, No. 21, pp. 7741-7751.

Carter, K. A., et al., Metal Chelation Modulates Phototherapeutic Properties of Mitoxantrone-Loaded Porphyrin-Phospholipid Liposomes, Molecular Pharmaceutics, Dec. 31, 2015, vol. 13, No. 2, pp. 420-427.

Li, Y., et al., Directed vaccination against pneumococcal disease, PNAS, Jun. 21, 2016, vol. 113, No. 25, pp. 6898-6903.

* cited by examiner

A) Top-view

Side-view

A)(cont.)

A)

Days After Bacterial Administration

A) (cont.)

```
                        SEQUENCE LISTING

<160> NUMBER OF SEQ ID NOS: 24

<210> SEQ ID NO 1
<211> LENGTH: 229
<212> TYPE: PRT
<213> ORGANISM: Streptococcus pneumoniae

<400> SEQUENCE: 1

Met Lys Lys Tyr Gln Leu Leu Phe Lys Ile Ser Ala Val Phe Ser Tyr
1               5                   10                  15

Leu Phe Phe Val Phe Gly Leu Ser Gln Leu Thr Leu Ile Val Gln Asn
            20                  25                  30

Tyr Trp Gln Phe Ser Ser Gln Ile Gly Asn Phe Val Trp Ile Gln Asn
        35                  40                  45

Ile Leu Ser Leu Leu Phe Ser Gly Val Met Ile Trp Ile Leu Val Lys
    50                  55                  60

Thr Gly His Gly Tyr Leu Phe Arg Ile Pro Arg Lys Lys Trp Leu Trp
65                  70                  75                  80

Tyr Ser Ile Leu Thr Val Leu Val Val Leu His Ile Ser Phe Asn
                85                  90                  95

Val Gln Thr Ala Lys His Val Gln Ser Thr Ala Glu Gly Trp Asn Val
            100                 105                 110

Leu Ile Gly Tyr Ser Gly Thr Asn Phe Ala Glu Leu Gly Ile Tyr Val
        115                 120                 125

Thr Leu Phe Phe Leu Thr Pro Leu Met Glu Glu Leu Ile Tyr Arg Gly
    130                 135                 140

Leu Leu Gln His Ala Phe Phe Lys His Ser Arg Phe Gly Leu Asp Leu
145                 150                 155                 160

Leu Leu Pro Ser Ile Leu Phe Ala Leu Pro His Phe Leu Ser Leu Pro
                165                 170                 175

Ser Leu Leu Asp Ile Phe Val Phe Ala Thr Phe Gly Ile Ile Phe Ala
            180                 185                 190

Gly Leu Thr Arg Tyr Thr Lys Ser Ile Tyr Pro Ser Tyr Ala Val His
        195                 200                 205

Val Ile Asn Asn Ile Val Ala Thr Phe Pro Phe Leu Leu Thr Phe Leu
    210                 215                 220

His Arg Val Leu Gly
225

<210> SEQ ID NO 2
<211> LENGTH: 608
<212> TYPE: PRT
<213> ORGANISM: Streptococcus pneumoniae

<400> SEQUENCE: 2

Met Glu Phe Ser Lys Lys Thr Arg Glu Leu Ser Ile Lys Lys Met Gln
1               5                   10                  15

Glu Arg Thr Leu Asp Leu Leu Ile Ile Gly Gly Ile Thr Gly Ala
            20                  25                  30

Gly Val Ala Leu Gln Ala Ala Ala Ser Gly Leu Glu Thr Gly Leu Ile
        35                  40                  45

Glu Met Gln Asp Phe Ala Glu Gly Thr Ser Ser Arg Ser Thr Lys Leu
    50                  55                  60
```

```
Val His Gly Gly Leu Arg Tyr Leu Lys Gln Phe Asp Val Glu Val Val
 65                  70                  75                  80

Ser Asp Thr Val Ser Glu Arg Ala Val Val Gln Gln Ile Ala Pro His
                 85                  90                  95

Ile Pro Lys Pro Asp Pro Met Leu Leu Pro Val Tyr Asp Glu Asp Gly
            100                 105                 110

Ala Thr Phe Ser Leu Phe Arg Leu Lys Val Ala Met Asp Leu Tyr Asp
        115                 120                 125

Leu Leu Ala Gly Val Ser Asn Thr Pro Thr Ala Asn Lys Val Leu Ser
130                 135                 140

Lys Asp Gln Val Leu Glu Arg Gln Pro Asn Leu Lys Lys Glu Gly Leu
145                 150                 155                 160

Val Gly Gly Val Tyr Leu Asp Phe Arg Asn Asn Asp Ala Arg Leu
                165                 170                 175

Val Ile Glu Asn Ile Lys Arg Ala Asn Gln Asp Gly Ala Leu Ile Ala
                180                 185                 190

Asn His Val Lys Ala Glu Gly Phe Leu Phe Asp Glu Ser Gly Lys Ile
        195                 200                 205

Thr Gly Val Val Ala Arg Asp Leu Leu Thr Asp Gln Val Phe Glu Ile
210                 215                 220

Lys Ala Arg Leu Val Ile Asn Thr Thr Gly Pro Trp Ser Asp Lys Val
225                 230                 235                 240

Arg Asn Leu Ser Asn Lys Gly Thr Gln Phe Ser Gln Met Arg Pro Thr
                245                 250                 255

Lys Gly Val His Leu Val Val Asp Ser Ser Lys Ile Lys Val Ser Gln
            260                 265                 270

Pro Val Tyr Phe Asp Thr Gly Leu Gly Asp Gly Arg Met Val Phe Val
        275                 280                 285

Leu Pro Arg Glu Asn Lys Thr Tyr Phe Gly Thr Asp Thr Asp Tyr
290                 295                 300

Thr Gly Asp Leu Glu His Pro Lys Val Thr Gln Glu Asp Val Asp Tyr
305                 310                 315                 320

Leu Leu Gly Ile Val Asn Asn Arg Phe Pro Glu Ser Asn Ile Thr Ile
                325                 330                 335

Asp Asp Ile Glu Ser Ser Trp Ala Gly Leu Arg Pro Leu Ile Ala Gly
            340                 345                 350

Asn Ser Ala Ser Asp Tyr Asn Gly Gly Asn Asn Gly Thr Ile Ser Asp
        355                 360                 365

Glu Ser Phe Asp Asn Leu Ile Ala Thr Val Glu Ser Tyr Leu Ser Lys
        370                 375                 380

Glu Lys Thr Arg Glu Asp Val Glu Ser Ala Val Ser Lys Leu Glu Ser
385                 390                 395                 400

Ser Thr Ser Glu Lys His Leu Asp Pro Ser Ala Val Ser Arg Gly Ser
                405                 410                 415

Ser Leu Asp Arg Asp Asp Asn Gly Leu Leu Thr Leu Ala Gly Gly Lys
            420                 425                 430

Ile Thr Asp Tyr Arg Lys Met Ala Glu Gly Ala Met Glu Arg Val Val
        435                 440                 445

Asp Ile Leu Lys Ala Glu Phe Asp Arg Ser Phe Lys Leu Ile Asn Ser
        450                 455                 460

Lys Thr Tyr Pro Val Ser Gly Gly Glu Leu Asn Pro Ala Asn Val Asp
465                 470                 475                 480
```

```
Ser Glu Ile Glu Ala Phe Ala Gln Leu Gly Val Ser Arg Gly Leu Asp
            485                 490                 495

Ser Lys Glu Ala His Tyr Leu Ala Asn Leu Tyr Gly Ser Asn Ala Pro
        500                 505                 510

Lys Val Phe Ala Leu Ala His Ser Leu Glu Gln Ala Pro Gly Leu Ser
    515                 520                 525

Leu Ala Asp Thr Leu Ser Leu His Tyr Ala Met Arg Asn Glu Leu Ala
530                 535                 540

Leu Ser Pro Val Asp Phe Leu Arg Arg Thr Asn His Met Leu Phe
545                 550                 555                 560

Met Arg Asp Ser Leu Asp Ser Ile Val Glu Pro Val Leu Asp Glu Met
            565                 570                 575

Gly Arg Phe Tyr Asp Trp Thr Glu Glu Lys Ala Thr Tyr Arg Ala
            580                 585                 590

Asp Val Glu Ala Ala Leu Ala Asn Asn Asp Leu Ala Glu Leu Lys Asn
            595                 600                 605

<210> SEQ ID NO 3
<211> LENGTH: 40
<212> TYPE: DNA
<213> ORGANISM: Streptococcus pneumoniae

<400> SEQUENCE: 3
taagcacata tgcaagaaaa atggtggcat aatgccgtag                           40

<210> SEQ ID NO 4
<211> LENGTH: 33
<212> TYPE: DNA
<213> ORGANISM: Streptococcus pneumoniae

<400> SEQUENCE: 4
taagcactcg agttccacac agaaagcatc cca                                  33

<210> SEQ ID NO 5
<211> LENGTH: 37
<212> TYPE: DNA
<213> ORGANISM: Streptococcus pneumoniae

<400> SEQUENCE: 5
taagcaccat ggggaaacat ctaaaaacat tttacaa                              37

<210> SEQ ID NO 6
<211> LENGTH: 32
<212> TYPE: DNA
<213> ORGANISM: Streptococcus pneumoniae

<400> SEQUENCE: 6
taagcactcg agagattcta aatcacctga ac                                   32

<210> SEQ ID NO 7
<211> LENGTH: 41
<212> TYPE: DNA
<213> ORGANISM: Streptococcus pneumoniae

<400> SEQUENCE: 7
taagcagagc tcgaattttc aaaaaaaaca cgtgaattgt c                         41

<210> SEQ ID NO 8
<211> LENGTH: 41
<212> TYPE: DNA
<213> ORGANISM: Streptococcus pneumoniae
```

-continued

```
<400> SEQUENCE: 8
taagcactcg agatttttta attctgctaa atcgttgtta g                41

<210> SEQ ID NO 9
<211> LENGTH: 32
<212> TYPE: DNA
<213> ORGANISM: Streptococcus pneumoniae

<400> SEQUENCE: 9
taagcacata tgatccaaat cggcaagatt tt                          32

<210> SEQ ID NO 10
<211> LENGTH: 36
<212> TYPE: DNA
<213> ORGANISM: Streptococcus pneumoniae

<400> SEQUENCE: 10
taagcagcgg ccgcaggagt agctgaagtt gtttta                      36

<210> SEQ ID NO 11
<211> LENGTH: 34
<212> TYPE: DNA
<213> ORGANISM: Streptococcus pneumoniae

<400> SEQUENCE: 11
taagcaccat ggggaatcct aatcttttta gaag                        34

<210> SEQ ID NO 12
<211> LENGTH: 34
<212> TYPE: DNA
<213> ORGANISM: Streptococcus pneumoniae

<400> SEQUENCE: 12
taagcactcg agatcagaat gggttaaaat ttta                        34

<210> SEQ ID NO 13
<211> LENGTH: 32
<212> TYPE: DNA
<213> ORGANISM: Streptococcus pneumoniae

<400> SEQUENCE: 13
taagcacata tgaaaaagta tcaacttcta tt                          32

<210> SEQ ID NO 14
<211> LENGTH: 34
<212> TYPE: DNA
<213> ORGANISM: Streptococcus pneumoniae

<400> SEQUENCE: 14
taagcactcg agccccaaga ccctatgtag aaaa                        34

<210> SEQ ID NO 15
<211> LENGTH: 32
<212> TYPE: DNA
<213> ORGANISM: Streptococcus pneumoniae

<400> SEQUENCE: 15
taagcagagc tcaaaaaaag cacagtattg tc                          32

<210> SEQ ID NO 16
<211> LENGTH: 34
<212> TYPE: DNA
```

<213> ORGANISM: Streptococcus pneumoniae

<400> SEQUENCE: 16
taagcactcg agatcttgat ttttttctt caat        34

<210> SEQ ID NO 17
<211> LENGTH: 37
<212> TYPE: DNA
<213> ORGANISM: Streptococcus pneumoniae

<400> SEQUENCE: 17
gcgggatccc aagaaaaatg gtggcataat gccgtag        37

<210> SEQ ID NO 18
<211> LENGTH: 30
<212> TYPE: DNA
<213> ORGANISM: Streptococcus pneumoniae

<400> SEQUENCE: 18
ataggcgcgc cttatagtaa ttccacacag        30

<210> SEQ ID NO 19
<211> LENGTH: 40
<212> TYPE: DNA
<213> ORGANISM: Streptococcus pneumoniae

<400> SEQUENCE: 19
gcggtcgaca aggagatata atggaatttt caaaaaaaac        40

<210> SEQ ID NO 20
<211> LENGTH: 29
<212> TYPE: DNA
<213> ORGANISM: Streptococcus pneumoniae

<400> SEQUENCE: 20
gcggcggccg cttaattttt taattctgc        29

<210> SEQ ID NO 21
<211> LENGTH: 31
<212> TYPE: DNA
<213> ORGANISM: Streptococcus pneumoniae

<400> SEQUENCE: 21
gcgcatatga tccaaatcgg caagattttt g        31

<210> SEQ ID NO 22
<211> LENGTH: 35
<212> TYPE: DNA
<213> ORGANISM: Streptococcus pneumoniae

<400> SEQUENCE: 22
gcgcaattgt taaggagtag ctgaagttgt tttag        35

<210> SEQ ID NO 23
<211> LENGTH: 44
<212> TYPE: DNA
<213> ORGANISM: Streptococcus pneumoniae

<400> SEQUENCE: 23
ataggccggc caaggagata taatggaaga atctcccgta gcca        44

<210> SEQ ID NO 24
<211> LENGTH: 34

```
<212> TYPE: DNA
<213> ORGANISM: Streptococcus pneumoniae

<400> SEQUENCE: 24
atactcgagt tattctgggg ctggagtttc tgga                              34
```

PNEUMOCOCCAL VACCINE FORMULATIONS

CROSS-REFERENCE TO RELATED APPLICATIONS

This application claims priority to U.S. Provisional Patent Application No. 62/318,514, filed on Apr. 5, 2016, the disclosure of which is incorporated herein by reference.

STATEMENT REGARDING FEDERALLY SPONSORED RESEARCH

This invention was made with government support under contract no. AI088485 awarded by the National Institutes of Health. The government has certain rights in the invention.

BACKGROUND OF THE DISCLOSURE

*Streptococcus pneumoniae* (the pneumococcus) is regarded as a major human pathogen and the most common cause of community-acquired pneumonia (CAP), bacterial meningitis, bacteremia, and otitis media (OM). In addition, *S. pneumoniae* has been implicated as an important cause of sinusitis, septic arthritis, osteomyelitis, peritonitis, and endocarditis. Regardless of clinical manifestation, infection is always preceded by colonization of the nasopharynx and greater than 95% of children will have been colonized within the first few weeks or months of life by serotypes that are sequentially replaced as more serotypes are acquired. Interestingly, pneumococcal colonization is asymptomatic, and it is only upon external triggering (via viral infection, for example) that virulent *S. pneumoniae* sub-populations disseminate and cause disease. The illnesses caused by this transition from carriage to disease result in an approximately 15-20% mortality rate in adults with an even higher rate in elderly patients. Pediatric cases include >20 million yearly occurrences in the U.S. and account for the majority of emergency room admissions and associated antibiotic prescriptions, accruing billions of dollars in annual socioeconomic costs. Invasive disease has a more devastating impact in resource-poor countries with an estimated one million children (11% of all deaths in children below age five) succumbing to pneumococcal infection annually.

Effectively treating pneumococcal disease is difficult due to multiple populations of *S. pneumoniae* with different characteristics, including cells localized to a colonizing biofilm and cells triggered for dissemination and disease. Antibiotic treatment options have become limited due to the emergence of antibiotic resistance. Prior to the 1990s, most *S. pneumoniae* strains demonstrated universal sensitivity to penicillin. However, today penicillin-resistance varies from 5-60% in various parts of the world. Of particular concern is the increase in multidrug-resistant *S. pneumoniae* strains, demonstrating resistance to 3+ drug classes, which attaches substantial concerns to current antibiotic regimens regarding both efficacy and continual resistance development. In addition, *S. pneumoniae* biofilm formation during colonization provides a barrier to effective antibiotic activity, thus, limiting complete bacterial clearance and promoting resistance development. Finally, and more importantly, even in the event of successful bacterial clearance with antibiotic treatment, there is a risk for re-colonization by potentially more dangerous serotypes or alternative pathogens (e.g., *Staphylococcus aureus*), which are equally adept at biofilm formation as well as effective mechanical tolerance and high biological resistance to antibiotics.

There are currently two pneumococcal vaccine compositions on the US market: the Prevnar® family (Pfizer) and Pneumovax® (Merck). Prevnar vaccines contain capsular polysaccharides conjugated to the diphtheria CRM197 protein. The most recent composition is Prevnar 13, which is designed to encompass 13 of the most common invasive serotypes of *S. pneumoniae* and provides protection against 74-88% of invasive pneumococcal disease cases (Alicinoet et al., Minerva Med 105, 89-97 (2014), Loo et al., The Pediatric infectious disease journal 33 Suppl 2, S140-151 (2014)). Pneumovax is a pneumococcal polysaccharide vaccine, introduced in 1977, that since 1983 has provided protection against 23 serotypes of *S. pneumoniae* (PPSV23) with 56-75% efficacy overall. However, efforts with current vaccination strategies have met with incomplete success due to 1) an inability to account for and include all current and future *S. pneumoniae* serotypes capable of establishing nasopharyngeal residence and 2) analogous to antibiotic treatment, the complete displacement of the asymptomatic vaccine-type *S. pneumoniae* biofilms with non-vaccine serotypes and by organisms (such as methicillin-resistant *S. aureus* [MRSA] or *Haemophilus influenzae*) capable of equal or greater pathologies (FIG. 1B) (Taylor et al., *Clin Infect Dis* 54, 1765-1773, (2012), Feldman et al., *The Journal of Infection* 69, 309-325, (2014), Madhi et al., *Journal of Infectious Diseases* 196, 1662-1666, (2007).

SUMMARY OF THE DISCLOSURE

This disclosure provides vaccine compositions that can be termed as "smart vaccines" and that leverage the current understanding of disease transition from bacterial carriage to infection with the pneumococcus serving as a model organism. Using conserved surface proteins highly expressed during virulent transition, the present vaccine compositions mount an immune response specifically against disease-causing bacterial populations without affecting carriage. Aided by a delivery technology capable of multivalent surface display, which can easily be adapted to a changing clinical picture, results include enhanced (including complete) protection against the development of pneumonia and sepsis during animal challenge experiments with multiple, highly-variable, and clinically-relevant pneumococcal isolates. The approach thus offers a unique and dynamic treatment option easily adaptable to other commensal pathogens.

In this disclosure, antigens associated with biofilm-released, virulent pneumococci have been demonstrated to show challenge protection and reduction in bacterial burden of a range of clinically-relevant *S. pneumoniae* strains under varying disease conditions. The results offer a response to a globally-relevant disease and growing concerns associated with current treatment options including risks posed by emerging serotype- and niche-replacement pathogens. Importantly, the same tools enabling the results of this work can be applied to continually identify and simultaneously deliver new antigens as a means to address the diversity and antigenic drift potential of *S. pneumoniae* and other pathogens that exhibit similar virulence progression.

In one aspect, this disclosure provides immunogenic compositions. For example, this disclosure provides vaccine compositions comprising bacterial antigens of *S. pneumoniae* that are expressed at relatively higher levels during virulent phase. The vaccine compositions may comprise PncO, GlnO or a combination of these two antigens. The compositions may comprise PncO, or PncO and GlpO as the only antigenic components. The compositions may additionally or alternatively comprise antigenic fragments of these antigens, such as those that are surface exposed. The compositions may additionally or alternatively comprise other antigens of *S. pneumoniae* or antigenic fragments of such antigens. The compositions may be delivered by any delivery vehicle. For example, one or more antigens may be present in solution or in suitable delivery vehicles such as nanovesicle, nanoparticles, microparticles, virus, and the like. Nanovesicles may be liposomes. Nanovesicles may comprise porphyrin phospholipid conjugates having cobalt chelated thereto. Delivery vehicles may be biological based hybrid delivery vehicles.

In one aspect, this disclosure provides a method of eliciting an immune response against streptococcal bacteria in an individual comprising administering to the individual an immunogenic composition comprising PncO, GlnO or a combination of these two antigens. The compositions administered to the individual, may comprise only PncO and/or GlpO, or may additionally or alternatively comprise antigenic fragments of these antigens, such as fragments that are surface exposed. The compositions may additionally comprise other antigens of *S. pneumoniae* or antigenic fragments of such antigens. The polypeptides used in the present compositions may be isolated polypeptides. The immunogenic compositions may be administered to an individual at risk of getting a streptococcal infection. The immunogenic compositions may be administered to populations of individuals who may be at risk of streptococcal infections, and may be part of routine yearly vaccinations.

In one aspect, this disclosure provides a method of identifying antigens for effective vaccine compositions against streptococcal infections, comprising identifying antigens, exclusively or preferentially expressed by strains of bacteria during the virulent phase, such as bacteria that are released by the nasopharynx mucosal biofilm during virulent phase, testing the antigens or fragments thereof, either alone or in combination with other antigens, to determine if such antigens provide protection against streptococcal infections, such as infections by *S. pneumoniae*.

BRIEF DESCRIPTION OF THE FIGURES

FIG. 15. Antibody profiles upon vaccination with the hybrid vector containing PspA. Distributions are provided at day 14 (D14; A) and 28 (D28; B) across administration routes. In the bar graphs under Weighted AbT, for A), and B), for each set, bars from left to right are IP, SQ, and IN.

DETAILED DESCRIPTION OF THE DISCLOSURE

Figure 1:
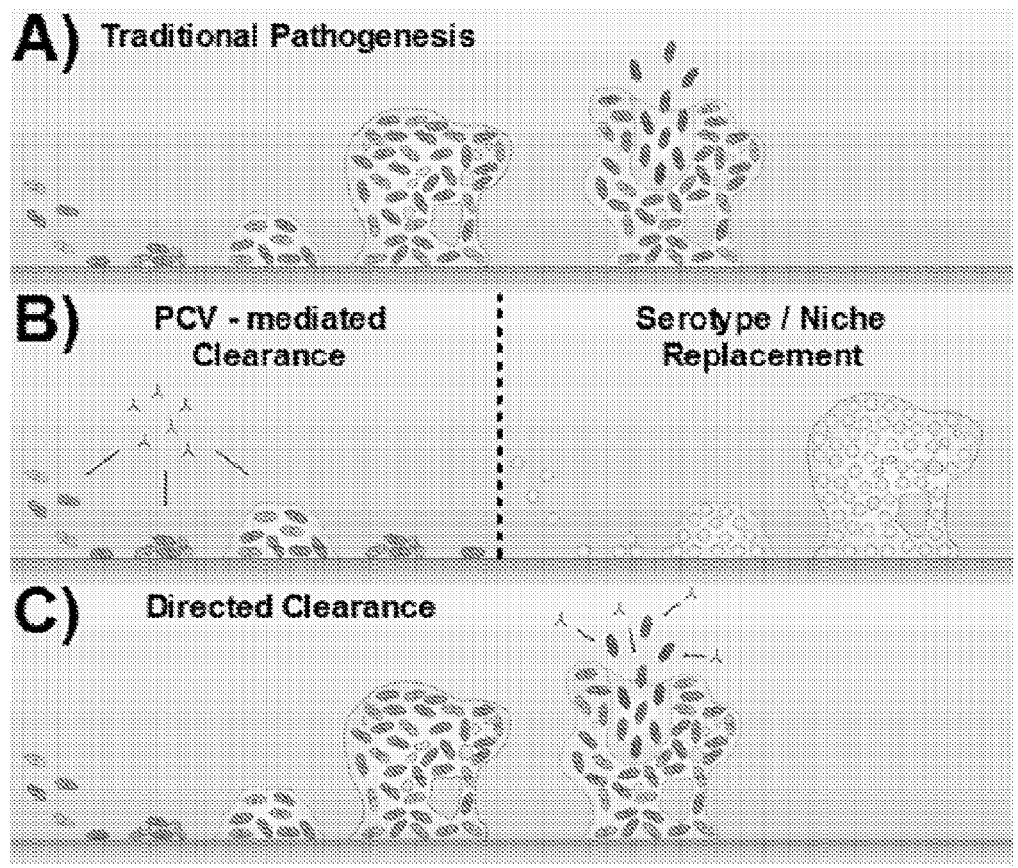
FIG. 1. *Streptococcus pneumoniae* pathogenesis outcomes and infectious disease statistics in the United States (1998-2013). (A) *S. pneumoniae* colonizes the human nasopharynx and produces bacterial communities or biofilms with a self-produced extracellular matrix and specialized structures protective from external and host challenges. External triggers such as viral infection prompt the active release of virulent pneumococci that disseminate to secondary sites and cause disease. (B) Leading vaccination strategies (polysaccharide conjugates vaccines [PCVs], such as the Prevnar family) mediate protection by promoting clearance of bacteria prior to biofilm establishment of serotypes included in the vaccines. By clearing all bacteria, the niche will be replaced by non-vaccine serotypes or other bacterial species. (C) The strategy featured in this work mediates clearance of only virulent, actively biofilm-released bacteria while simultaneously maintaining the presence of the pre-existing biofilm. (D) Annual infection rate per 100,000 people for the total population and children under the age of five from 1998-2013. The first year following introduction of Prevnar 7 and 13 are marked with dotted lines. (E) Prevalence of infectious pneumococcal strains from 1999 to 2011 (Richter et al., *Emerg Infect Dis* 19, 1074-1083, (2013)). Strains are grouped into those covered by Prevnar 7 (from left, first in each set), those covered by Prevnar 13 (second (middle) in each set), and non-vaccine types (NVT; third (right) in each set). (F) Reduction in annual infection rate in children under the age of five from 1998 to 2008 relative to 1998-1999. Dashed line corresponds to division between Prevnar 7 vaccine and non-vaccine type strains in 1999-2000 (Richter et al., *Emerg Infect Dis* 19, 1074-1083, (2013)). (G) Reduction in annual infection rate in children under the age of five from 2008 to 2013. Dashed line corresponds to division between Prevnar 13 vaccine and non-vaccine type strains in 2008-2009 (Richter et al., *Emerg Infect Dis* 19, 1074-1083, (2013)).
Figure 1:
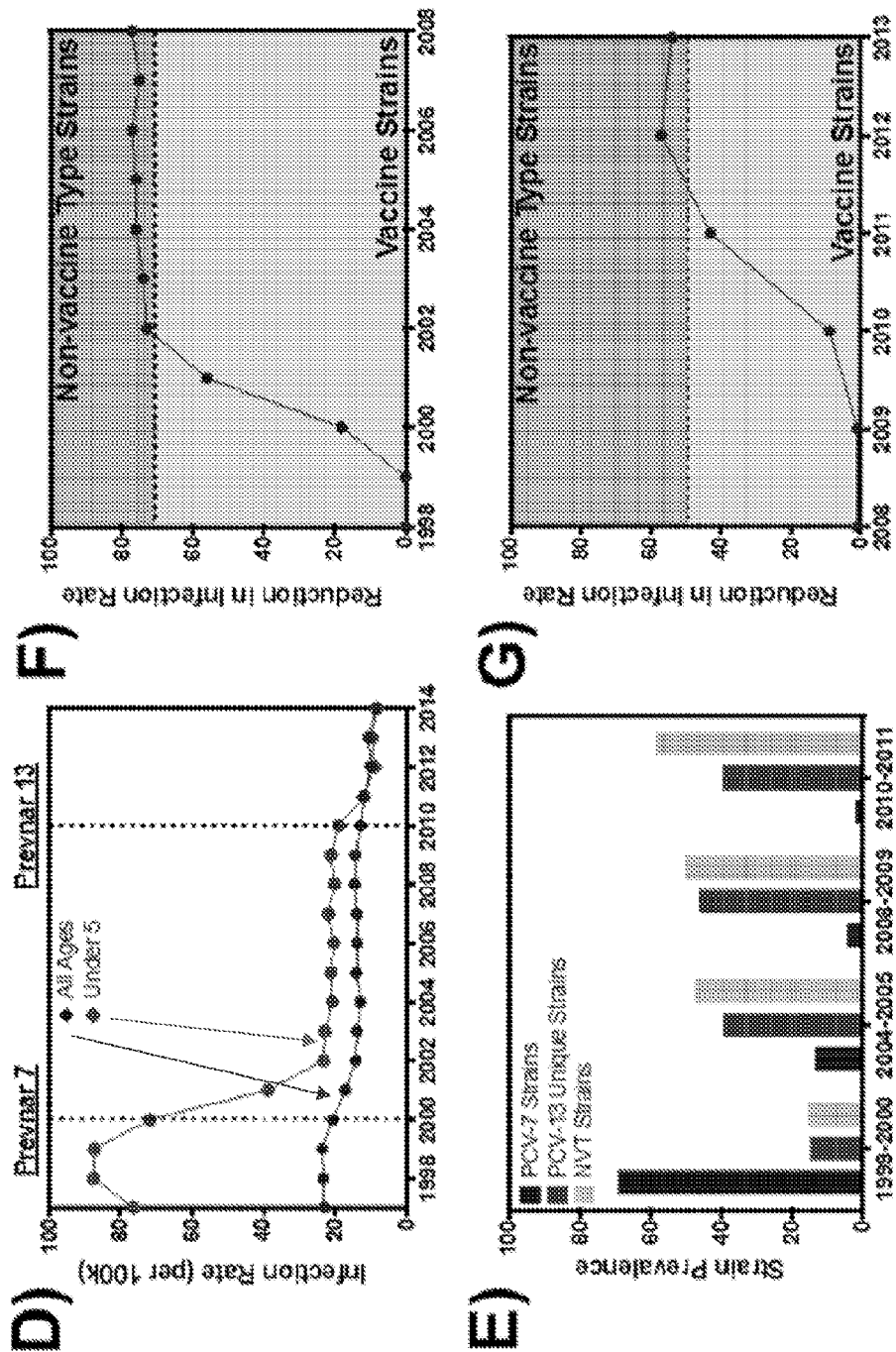

In this disclosure we provide a treatment approach directed at a disease progression state of a microbial population rather than the general population. Doing so offers the potential to optimize treatment and reduce unintended pathological consequences. Such an approach is provided herein in the context of pneumococcal disease, culminating in a "smart vaccine" that directs an immune response to virulent cell populations while minimizing disruption of avirulent commensal colonization.

The term "immune response" as used herein refers to the concerted action of the cells of the immune system including one or more of lymphocytes, antigen presenting cells, phagocytic cells, granulocytes, and others that results in selective damage to, destruction of, or elimination from the animal body of invading pathogens, cells or tissues infected with pathogens.

The term "immunogen" as used herein refers to a substance that is able to stimulate or induce a humoral antibody and/or cell-mediated immune response in a mammal. This term may be used interchangeably with "antigen" herein.

The term "isolated" as used herein with respect to polypeptides means polypeptides that are substantially separated from other macromolecules normally associated with the polypeptide in its natural state. An isolated polypeptide can be completely free of other macromolecules normally associated with the polypeptide in its natural state. For example, polypeptides may be at least 50, 60, 70, 80, 90, 95, or 99% pure. An isolated polypeptide, for example, can be purified from a cell that normally expresses the polypeptide, may be synthesized, or can be produced using recombinant DNA methodology.

The terms "polypeptide", "peptide" and "protein" may be used interchangeably to mean a polymer comprising two or more amino acids joined to each other by peptide bonds or modified peptide bonds. Short chains are generally referred to as peptides (about 30 amino acids or less), medium chains as polypeptides (from 30 to 1,000 amino acids), and longer chains as proteins. Polypeptides may contain amino acids other than the 20 gene-encoded amino acids. Polypeptides include amino acid sequences modified either by natural processes, such as post-translational processing, or by chemical modification techniques that are well known in the art.

The present disclosure provides compositions comprising PncO or a fragment thereof that elicits an immune response protective against a *streptococcus*, such as, for example, *Streptococcus pneumoniae*. The PncO may be any one of those produced by a *Streptococcus* species, including those from *Streptococcus pneumoniae*, *Streptococcus gordonii*, *Streptococcus sanguinis*, *Streptococcus thermophilus*, *Streptococcus suis*, *Streptococcus agalactiae*, *Streptococcus pyogenes*, *Streptococcus mutans*, *Enterococcus faecalis*, *Enterococcus faecium*, *Rhodococcus* sp.

The PncO need not be identical to the amino acid sequence of the PncO *S. pneumoniae*. Various modifications can be made to the protein sequence without altering its immunogenicity, and protective capacity of antibodies raised thereto. For example, conservative substitutions may be made within the group of following amino acids 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). For example, the antigen may be from 90 to 99% identical to the sequence of PncO provided herein, wherein the antigen is able to generate protective antibodies against a *streptococcus*, such as, for example, *Streptococcus pnuemoniae*.

The sequence of PncO is available as GenBank Accession No. ABJ54598.1 for pncO (blpY) from *Streptococcus pneumoniae* D39. The sequence is provided below.

```
                                          SEQ ID NO: 1
MKKYQLLFKI SAVFSYLFFV FGLSQLTLIV QNYWQFSSQI

GNFVWIQNIL SLLFSGVMIW ILVKTGHGYL FRIPRKKWLW

YSILTVLVVV LHISFNVQTA KHVQSTAEGW NVLIGYSGTN

FAELGIYVTL FFLTPLMEEL IYRGLLQHAF FKHSRFGLDL

LLPSILFALP HFLSLPSLLD IFVFATFGII FAGLTRYTKS

IYPSYAVHVI NNIVATFPFL LTFLHRVLG.
```

Figure 28:
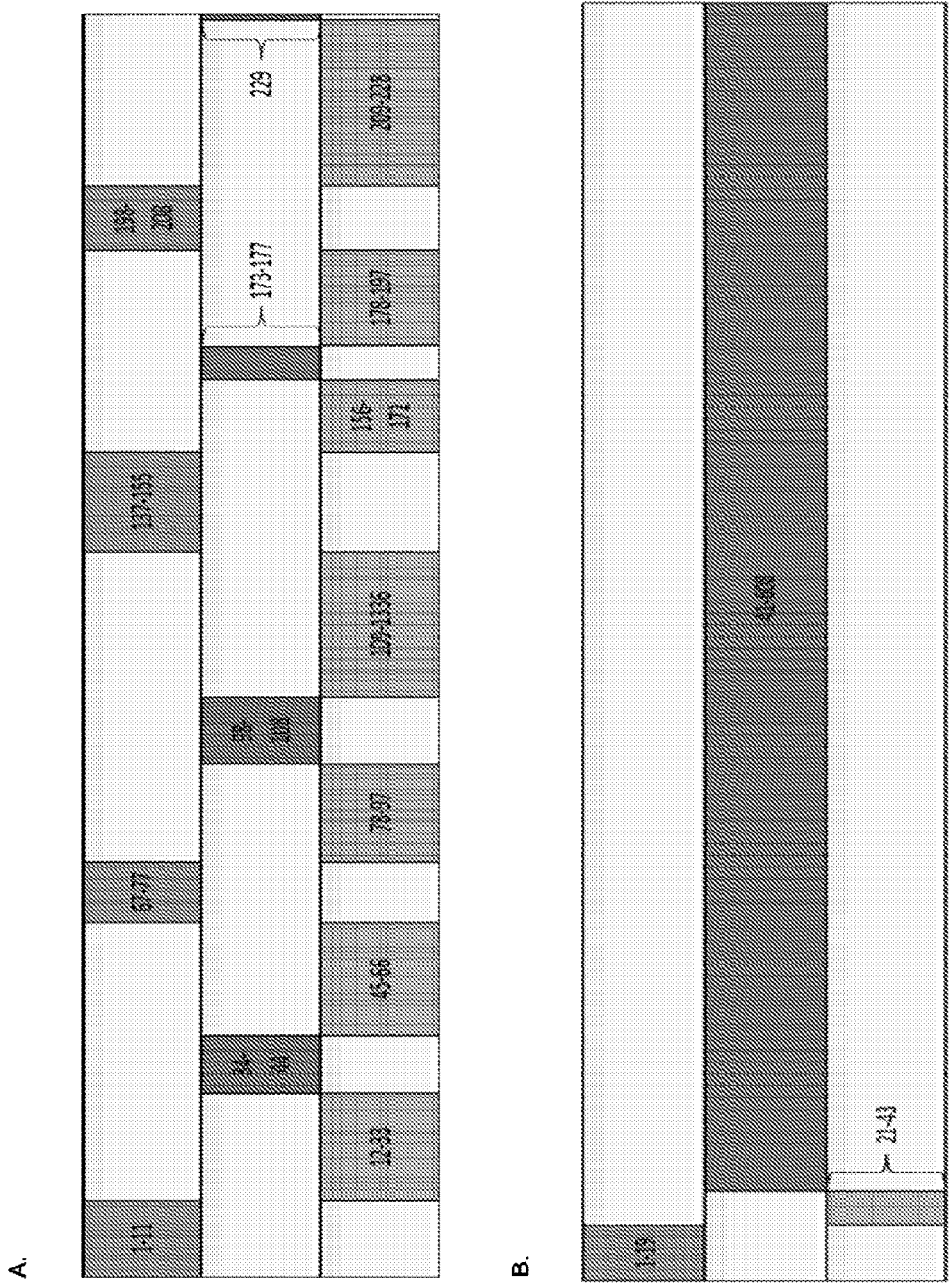
FIG. 28. Graphical representation of surface accessible regions in the PncO sequence (A) and GlpO sequence (B). Top row shows darker shaded cytoplasmic regions, the middle row shows darker shaded surface accessible regions and the bottom row shows darker shaded transmembrane regions. Amino acid numbers are from SEQ ID NO:1 for PncO (A) and from SEQ ID NO:2 for GlpO (B) corresponding to the regions are provided in the boxes.

The surface accessible regions in the PncO sequence are bolded above. This is also illustrated in FIG. 28, where the top row shows dark shaded cytoplasmic regions, the middle row shows dark shaded surface accessible regions and the bottom row shows dark shaded transmembrane regions.

The immunogenic antigen may be from 80 to 99% identical to the sequence of PncO provided herein, wherein the antigen is able to generate protective antibodies against a *streptococcus*, such as, for example, *Streptococcus pnuemoniae*. In one embodiment, the PncO has at least 70% identity, preferably 80 or 85%, such as at least 90% or at least 95, 98 or 99% identity to the PncO of SEQ ID NO:1.

The sequence of GlpO is available as GenBank Accession No. EC 1.1.3.21 from *Streptococcus pneumoniae* D39. The sequence is provided below.

```
                                          SEQ ID NO: 2
MEFSKKTRELSIKKMQERTLDLLIIGGGITGAGVALQAAASGLETGLIE

MQDFAEGTSSRSTKLVHGGLRYLKQFDVEVVSDTVSERAVVQQIAPHIP

KPDPMLLPVYDEDGATFSLFRLKVAMDLYDLLAGVSNTPTANKVLSKDQ

VLERQPNLKKEGLVGGGVYLDFRNNDARLVIENIKRANQDGALIANHVK

AEGFLFDESGKITGVVARDLLTDQVFEIKARLVINTTGPWSDKVRNLSN

KGTQFSQMRPTKGVHLVVDSSKIKVSQPVYFDTGLGDGRMVFVLPRENK

TYFGTTDTDYTGDLEHPKVTQEDVDYLLGIVNNRFPESNITIDDIESSW

AGLRPLIAGNSASDYNGGNNGTISDESFDNLIATVESYLSKEKTREDVE

SAVSKLESSTSEKHLDPASVSRGSSLDRDDNGLLTLAGGKITDYRKMAE

GAMERVVDILKAEFDRSFKLINSKTYPVSGGELNPANVDSEIEAFAQLG

VSRGLDSKEAHYLANLYGSNAPKVFALAHSLEQAPGLSLADTLSLHYAM

RNELALSPVDFLLRRTNHMLFMRDSLDSIVEPVLDEMGRFYDWTEEEKA

TYRADVEAALANNDLAELKN
```

The surface accessible regions in the GlpO sequence are bolded above. This is also illustrated in FIG. 28B, where the top row shows darker shaded cytoplasmic regions, the middle row shows darker shaded surface accessible regions and the bottom row shows darker shaded transmembrane regions.

The immunogenic antigen may be from 80 to 99% identical to the sequence of GlpO provided herein, wherein the antigen is able to generate protective antibodies against a *streptococcus*, such as, for example, *Streptococcus pnuemoniae*. In one embodiment, the GlpO immunogenic antigen has at least 70% identity, preferably 80 or 85%, such as at least 90% identity or at least 95, 98 or 99% identity to the GlpO sequence provided herein.

The immunogenic composition can have PncO as the only antigen, PncO and GlpO as the only antigens or it can have additional antigens. For example, the immunogenic composition can comprise PncO and other *Streptococcus* antigens, such as antigens from *S. pnuemoniae*, particularly those that are at least partially or fully surface exposed. For example, the compositions can have stkP and PspA.

The composition can comprise PncO and GlpO, and/or antigenic fragments thereof, which fragments are able to generate protective antibodies against a *streptococcus*, such as, for example, *Streptococcus pnuemoniae*. The antigenic fragments may be isolated fragments. The antigenic fragments are typically 15 to 30 amino acid (and all amino acid numbers therebetween) long and will ideally comprise an epitope from the surface exposed portions of the sequences. For example, the fragments may comprise amino acid sequences that contain the sequences of the surface exposed portions shown in FIG. 28 for PncO and GlpO.

The formulation can include a carrier or excipient. The formulations can include an adjuvant to enhance the extent or nature of the immune reaction. Determination of the amount of the immunogenic antigen and/or the adjuvant can be in accordance with standard techniques in the pharmaceutical or veterinary arts.

Adjuvants that may be usefully employed in the preparation of vaccines include the following: oil adjuvants, for example, Freund's complete and incomplete adjuvants, mineral salts, alum, silica, kaolin, and carbon, polynucleotides and certain natural substances of microbial origin. An example of an adjuvant is a non-covalent complex of alpha-lactalbumin and fatty acid. Fatty acids useful for making the complex include unsaturated cis C14 to C20 fatty acids. (See WO 2014/008465). An example of an adjuvant is monophsophryl A.

With administration of immunogenic antigens, typically an adjuvant is used. For example, an adjuvant can be used as a 0.001 to 50 wt % solution in phosphate buffered saline, and the antigen is present in the order of micrograms to milligrams, such as about 0.0001 to about 5 wt %, such as about 0.0001 to about 1 wt %, such as about 0.0001 to about 0.05 wt %. The antigen can be present in an amount in the order of micrograms to milligrams, or, about 0.001 to about 20 wt %, such as about 0.01 to about 10 wt %, or about 0.05 to about 5 wt %.

The present disclosure provides pharmaceutical preparations which comprise, consist essentially of, or consist of PncO or immunogenic fragments thereof. The preparations can comprise other antigens such as, for example, GlpO. In one embodiment, the only antigens in the preparation are PncO and GlpO and/or immunogenic fragments thereof. For example, the composition may comprise PncO and/or GlpO as the only polypeptides in the composition.

The pharmaceutical preparations can comprise additives, such as diluent, adjuvant, excipient, or carrier. Such additives can be liquids, such as water and oils, saline, glucose or the like, and auxiliary, stabilizing, thickening, or lubricating agents, wetting or emulsifying agents, or pH buffering agents, gelling or viscosity enhancing additives, detergents and solubilizing agents (e.g., TWEEN® 20, TWEEN® 80 also referred to as polysorbate 20 or 80), anti-oxidants (e.g., ascorbic acid, sodium metabisulfite), preservatives (e.g., Thimersol, benzyl alcohol), bulking substances (e.g., lactose, mannitol), flavoring agents, colors, and the like, depending upon the route of administration and the preparation desired. See "Remington's Pharmaceutical Science", 17th edition, 1985. Non-aqueous solvents or vehicles can be used such as propylene glycol, polyethylene glycol, vegetable oils, such as olive oil and corn oil, gelatin, and injectable organic esters such as ethyl oleate. The formulations may be lyophilized and redissolved or resuspended just before use. The formulation may be sterilized by, for example, filtration through a bacteria retaining filter, by incorporating sterilizing agents into the compositions, by irradiating the compositions, or by heating the compositions.

The present compositions can be provided as liquid preparations, suspensions, emulsions, tablets, pills, sustained-release formulations, emulsions, aerosols, sprays, or any other form suitable for introducing the compositions into a subject to generate an immune response protective against *S. pneumoniae* or other streptococcaciae. The compositions may be administered to a human or a non-human animal.

The antigenic compositions can be administered in delivery vehicles, which can include, but are not limited to, nanoparticles, nanovesicles (such as liposomes or other lipidic structures) and biological or hybrid delivery vehicles. Liposomes may comprise one or more types of phospholipids known in the art. Nanovesicles comprising porphyrin conjugates can be used. The nanovesicles comprising porphyrin conjugates may have cobalt chelated to the porphyrin moiety. For example, the nanovesicles can comprise porphyrin phospholipid conjugate, phospholipid that is not conjugated to phospholipid, optionally cholesterol, and optionally PEG-phospholipid. The phospholipids can be any phospholipids, saturated or unsaturated, such as DOPC, DMPC and DSPC. Nanovesicle carrier capable of surface-orienting peptide-based antigens are useful for enhanced immune responses. The nanovesicles may have an in-built adjuvant component. A biological based delivery vehicle can also be used. For example, a hybrid vector delivery vehicle described in WO2016019126 can be used. The hybrid vehicle can have incorporated therein an adjuvant.

The adjuvant can be administered as a separate component in the immunogenic compositions or it can be incorporated into the delivery vehicle.

The antigenic compositions may be used with a hybrid vector delivery vehicle. For example, a hybrid vector designed to assist the intracellular delivery of antigen cargo to antigen presenting cells can be used. The hybrid vector can be a biological based vector. For example, as a combination of biomaterial and biological components, each chosen due to individual use as delivery vehicles, the combined vector allows synergistic delivery mechanisms and disparate engineering tools to influence the process of antigen transport. Thus, steps associated with antigen presenting cells (APC) targeting, uptake, activation, and intracellular antigen release have been designed through a combination of the two components of the hybrid device. Highlighting the dual engineering capabilities of the hybrid vector are the polymer chemistry steps used to conjugate a mannose ligand to the poly(beta-amino ester) shell of the device which aids in APC targeting and vector uptake. Similarly, expression and localization of the LyE protein to the bacterial component of the hybrid vector safely extends the dose limits of the device.

A different aspect of the vector is also highlighted. Namely, the option for in situ antigen generation. Here, the biological core of the vector allows the molecular biology tools associated with a facile microbe like *E. coli* to be used in both antigen consolidation and internal expression prior to delivery. This capability makes the normal requirement of separate bioprocesses dedicated to antigen generation and purification unnecessary and allows a "one-pot" production and delivery device for vaccine applications.

The hybrid vector design also offers options associated with stable storage and widespread distribution; however, features related to production and access are targets of future research. In the present work, the results illustrate the first directed application of the vector, tested in the context of pneumococcal disease. The hybrid vector demonstrated improved immune response metrics using a model protein antigen (PspA) when compared to traditional vaccine formulations with alum and CFA. More importantly, once the molecular biology tools of the vector were utilized to consolidate newly-identified antigens, protection was provided across a range of clinically-relevant *S. pneumoniae* strains and disease models.

The antigens selected for consolidation to the hybrid vector are based upon those upregulated during virulent transition, thus, the objective is to target the disease-causing subset from a greater population of colonizing and asymptomatic *S. pneumoniae* cells. This capability was observed across different pneumococci strains, administration routes, and in vivo conditions, including disease onset triggered by influenza. Furthermore, the effectiveness of the antigens delivered with the hybrid vector resulted in protection extended to 10 additional *S. pneumoniae* strains. Though not all levels of protection were the same, complete protection was observed in 11 of 15 cases, emphasizing the broad coverage potential of the consolidated antigens tested in this study. Owing to the tools associated with the hybrid vector, even broader coverage can be expected upon the consolidation of additional virulence-associated antigens into the vector design. This feature, coupled with the conserved nature of the antigens identified and tested (Table 1 and FIG. 21), offers an excellent prospect of combatting antigenic drift and the resulting reduction in vaccine efficacy. Such concerns currently plague various vaccines associated with this and other diseases. Thus, the conserved nature of the antigens selected and consolidation options provided through the hybrid vector offer a solution to this issue.

Balancing the capabilities offered by the hybrid design is the potential for toxicity given the bacterial nature of the vector's core and the cationic charge of the polymer coating. As demonstrated, the final vector provides attenuation through cellular engineering of the bacterial core and via the process of polymer coating. More importantly, the vector has not provoked any toxicity upon administration unless heightened dosages are utilized. Yet, even under enhanced dosage levels, it is possible to negate toxic effects due to the biological attenuation afforded by the LyE gene, providing another level of engineering design in applying the hybrid vector.

Consolidating virulent-specific antigens to the hybrid device also offers a smart vaccine with in-built antigen production or an in situ means of cargo generation. Combined, the vector offers engineering elements that range from process-level scalability and distribution to cellular-level immune response tunability with the potential to be directed at a number of challenging vaccine opportunities beyond pneumococcal disease.

The compositions can be administered to a population in general, or can be targeted to individuals who are at risk for developing *Streptococcus* infections such as *S. pneumoniae*. For example, it can be administered to any individual who is in close contact with an infected individual.

The compositions can be introduced into a subject using any suitable administration route, including but not limited to parenteral, subcutaneous, intraperitoneal, intramuscular, intravenous, mucosal, topical, intradermal, and oral administration.

Immunization can be done by way of a single dose or it can be done by multiple doses that are spaced apart. For example, an initial administration and subsequent booster doses can be used. The compositions can be administered alone, or can be co-administered or sequentially administered with other prophylactic (such as, for example, other immunogenic compositions) or therapeutic compositions (such as, for example, antibiotics).

In one aspect, this disclosure provides a method of preventing pneumonia in an individual comprising administering to the individual an effective amount of a composition described herein. This disclosure also provides a method of reducing the overall incidence of pneumonia in a population comprising administering to a plurality of individuals in the population an effective amount of compositions described herein, whereby administration of the immunogenic compositions prevents the occurrence of pneumonia in at least some of the individuals in the population such that overall incidence of pneumonia n the population is reduced.

The method of the present disclosure provides a strategy to induce an antibody-mediated immune response against a disease-causing subset of a commensal microbial population. Specifically, antigens associated with biofilm-released, virulent pneumococci have demonstrated unequivocal challenge protection and reduction in bacterial burden of a range of clinically-relevant *S. pneumoniae* strains under varying disease conditions. The results offer a response to a globally-relevant disease and growing concerns associated with current treatment options including risks posed by emerging serotype- and niche-replacement pathogens. Importantly, the same tools enabling the results of this work can be applied to continually identify and simultaneously deliver new antigens as a means to address the diversity and antigenic drift potential of *S. pneumoniae* and other pathogens that exhibit similar virulence progression.

In one aspect, the present disclosure provides a method of identifying immunogens, such as genes, RNA, proteins, immunogens, or polypeptides that can be used for vaccine compositions against pathogens colonizing the nasal cavity mucosa—generally as a biofilm. Such pathogens will include new serotypes of *S. pneumoniae*, other bacteria (including those commonly found in the nasopharynx and those that colonize in addition), or other microbial targets (including viruses or fungal organisms). The method comprises inducing release of the pathogens by applying external triggers, including viral induced release or heat triggered release etc. For example, heat triggered release can be achieved by exposure to temperatures higher than normal body temperatures. For example, the biofilm release can be achieved by exposure to temperatures from 37° C. to 39° C. for about 1 to 6 hours, or more. The released cells can be collected and characterized. Specific serotypes can be identified, cultured and surface exposed proteins can be identified that are unique to the serotype, for example. The same analysis can identify numerous molecular antigenic targets, as introduced above that could also be valuable vaccine ingredients. The newly identified proteins or portions thereof can be used to determine if immunizations with these proteins or portions thereof (such as surface exposed portions) can induce immunity against a broad spectrum of *S. pneumoniae* and/or other microbial targets.

Example 1

The current work presents a strategy capable of providing directed protection against virulent, biofilm-released *S. pneumoniae*. Thus, the present strategy is based upon selectively targeting those pneumococci that are triggered for virulent biofilm escape in response to changes in the nasopharyngeal environment (FIG. 1C).

Figure 2:
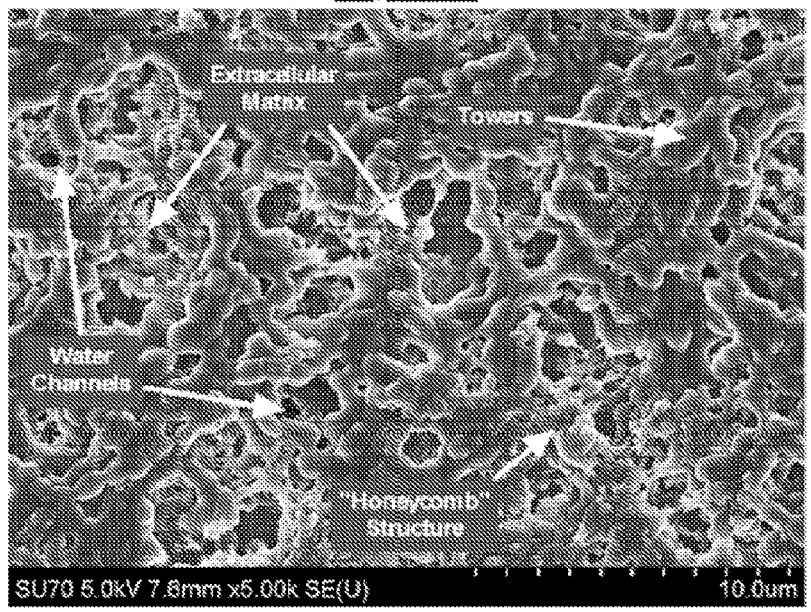
FIG. 2. Identification and characterization of antigens associated with biofilm-released *S. pneumoniae* bacteria. (A) *S. pneumoniae* D39 were seeded on epithelial cells, and the biofilm structure was investigated using SEM. Visible in these images are the extracellular matrix, water channels, tower formations, and the "honeycomb" structure that pneumococci form with larger biofilms. Mouse bacterial burden was determined of pneumococcal populations after (B) intraperitoneally injections (sepsis model) or (C) intranasal aspiration with anesthesia (pneumonia model) using broth grown (Planktonic), biofilm-associated (Biofilm), or heat-dispersed (Heat) EF3030. Each dot in the graphs represents an individual mouse. (D) Time to death assessment of mice inoculated with heat-released bacteria from the sepsis (B) and pneumonia (C) models. Mice that were inoculated with either planktonic or biofilm-associated bacteria did not render death in any challenge model. Mice were immunized with various antigens and challenged with heat-released EF3030 in sepsis (E and F) and pneumonia (G) models. Dotted line represents limit of detection for bacterial counts. *$P<0.05$, $P<0.01$, and *$P<0.001$, compared to Planktonic and Biofilm samples (B and C) and PspA (E). In (B), the dots in each set from left to right represent: Blood, Liver, and Spleen. In (C), the dots in each set from left to right represent: Blood, and Lung. In B, C and E, for each group of dots, thick bars indicate mean.
Figure 2:
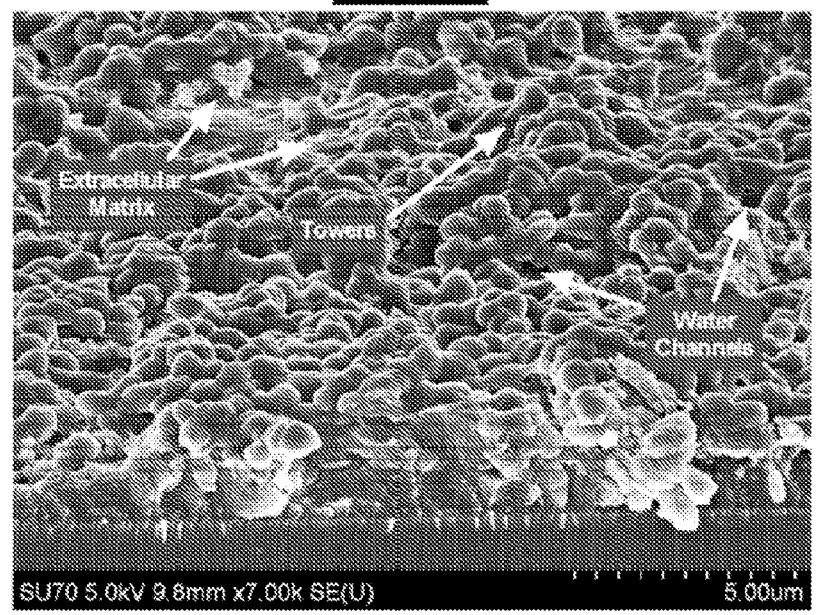
Figure 2:
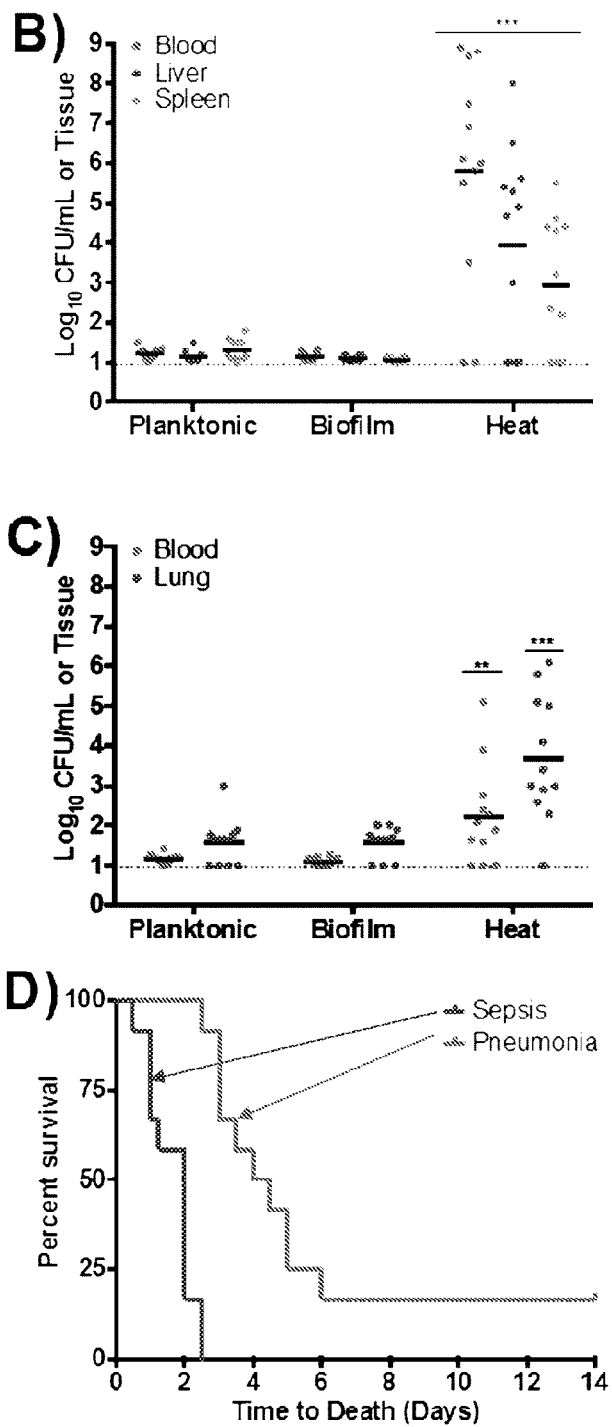
Figure 2:
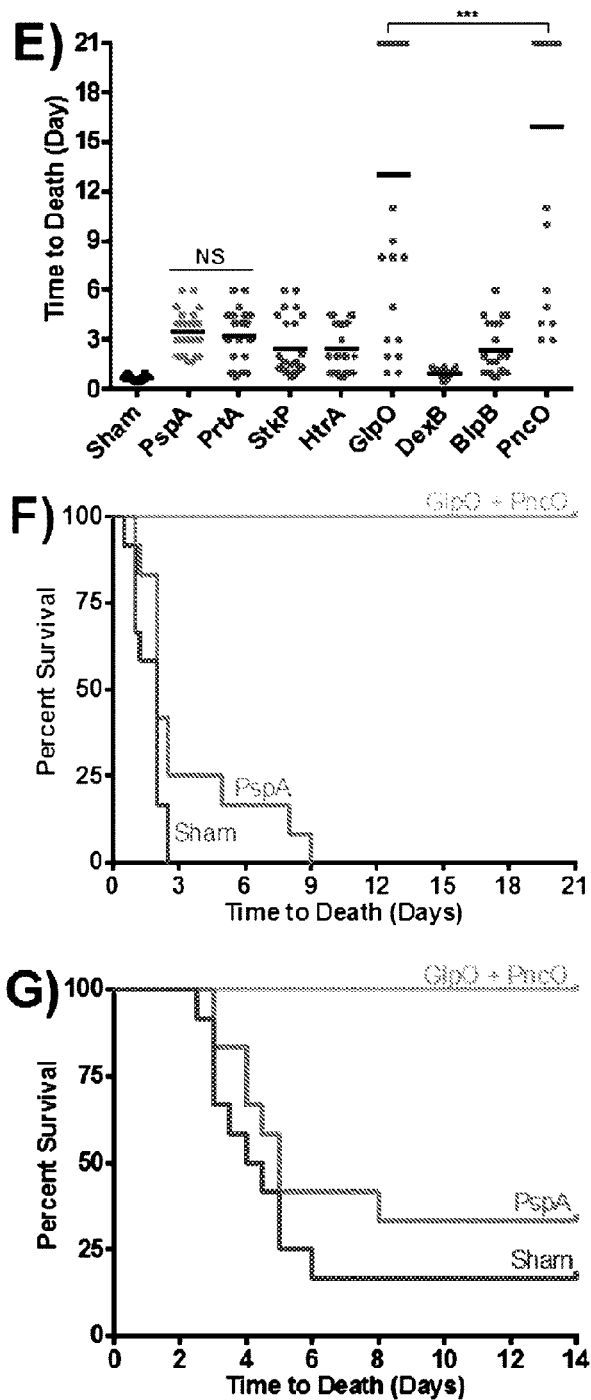

Through the combination of an in vitro biofilm model (FIG. 2A), which was treated with or without factors associated with virus-induced inflammation of the nasopharynx, and transcriptional analysis of the bacterial populations comprising this model, antigens were identified that were specifically upregulated in biofilm-released pneumococci which demonstrated increased virulence. *S. pneumoniae* is a human pathogen that, with the exception of a few strains, cannot cause invasive disease in mice. The biofilm model was used to condition a clinical isolate of *S. pneumoniae* (EF3030, serotype 19F), that is cleared from the bloodstream of mice when grown in broth, to become lethally infectious. Specifically, EF3030 cells released from biofilms by increased temperature (38.5° C., mimicking fever) induced septicemia and death in mice and thus offered a clinically-relevant surrogate model of human pneumococcal disease (FIG. 2B-D). Planktonic, broth grown EF3030 pneumococci or those mechanically isolated from biofilms had no such virulence. Initial protection was then investigated by immunizing with a range of promising new antigen targets (Table 1) selected on the basis of 1) conserved sequence homology across all *S. pneumoniae* strains (thus, offering broad coverage potential) and, critically, 2) specific prominence in the virulent, biofilm-released bacterial population compared with the asymptomatic biofilm population. Namely, antigen targets up-regulated in biofilm-released pneumococci were prepared as recombinant proteins and tested for protection relative to the established *S. pneumoniae* surface protein antigen (PspA), which is also up-regulated during virulence transition (FIG. 2E). To better compare efficacy of novel antigens with PspA, a bacterial challenge dosage was chosen that resulted in incomplete protection with PspA vaccination. Under these conditions, GlpO (an α-glycerophosphate oxidase) and PncO (a bacteriocin ABC transporter transmembrane protein) demonstrated promising individual protection. However, complete protection and effective bacterial reduction were conferred upon immunization with both antigens (FIGS. 2F&G), an important result considering the effectiveness of the antigens against a clinical isolate of *S. pneumoniae* and a clear improvement relative to current vaccine candidates (i.e., PspA).

Figure 5:
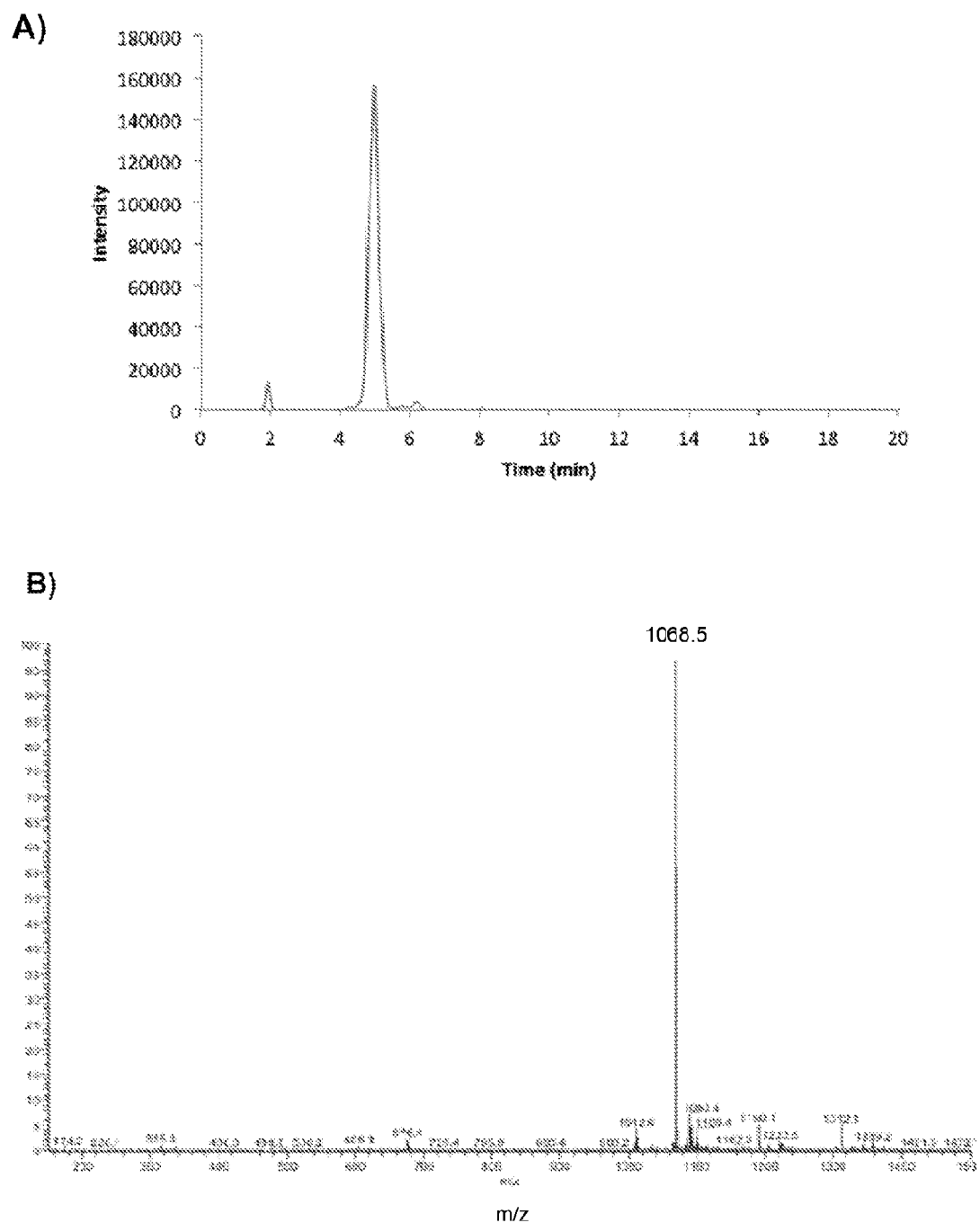
FIG. 5. Characterization of lipid synthesis and liposomes. (A) The high performance liquid chromatography (HPLC) of cobalt porphyrin-phospholipid (Co-PoP) and the (B) resulting mass spectrum. (C) Binding analysis for all proteins used in the study. (D) Particle diameter and (E) zeta potential of liposomes formulated with 0, 5, and 15 µg of PspA.
Figure 5:
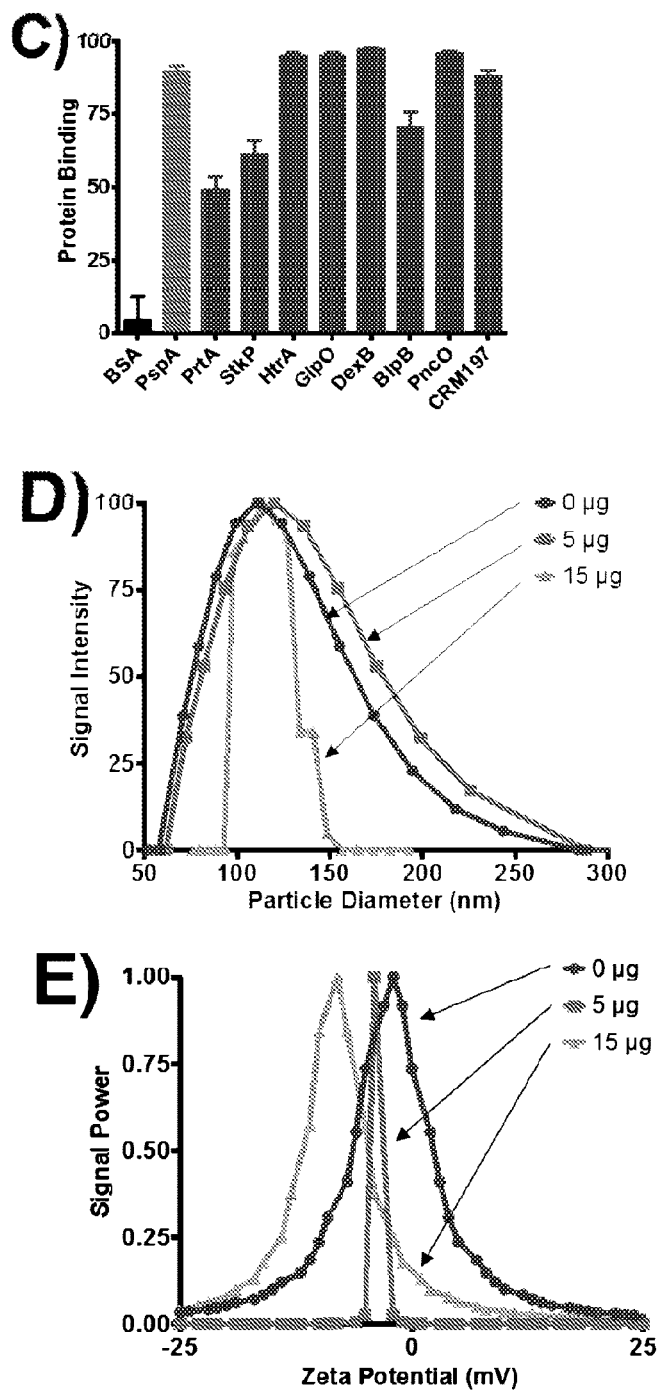
Figure 6:
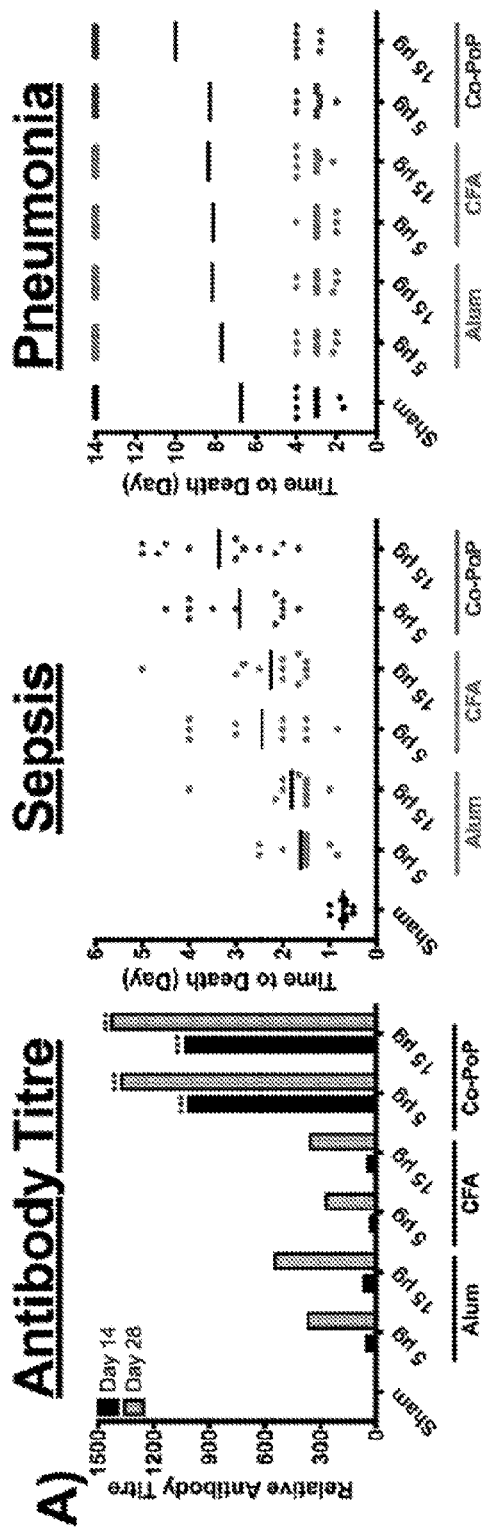
FIG. 6. Optimization of immunization delivery parameters. PspA was formulated with alum, complete Freund's adjuvant, and Co-PoP liposomes at two concentrations and administered (A) i.p., (B) s.q., and (C) i.n. before being assessed for antibody titer or in either a sepsis or pneumonia challenge model using planktonic D39 ($1 \times 10^6$ cells). *$P<0.05$, $P<0.01$, and *$P<0.001$, indicating significant differences between the immunization doses and time points. For example, Co-PoP:5 µg at Day 14 was compared to Alum:5 µg and CFA:5 µg at Day 14. In A), B), and C), under Sepsis, and Pneumonia, for each group of dots, bars indicate mean.
Figure 6:
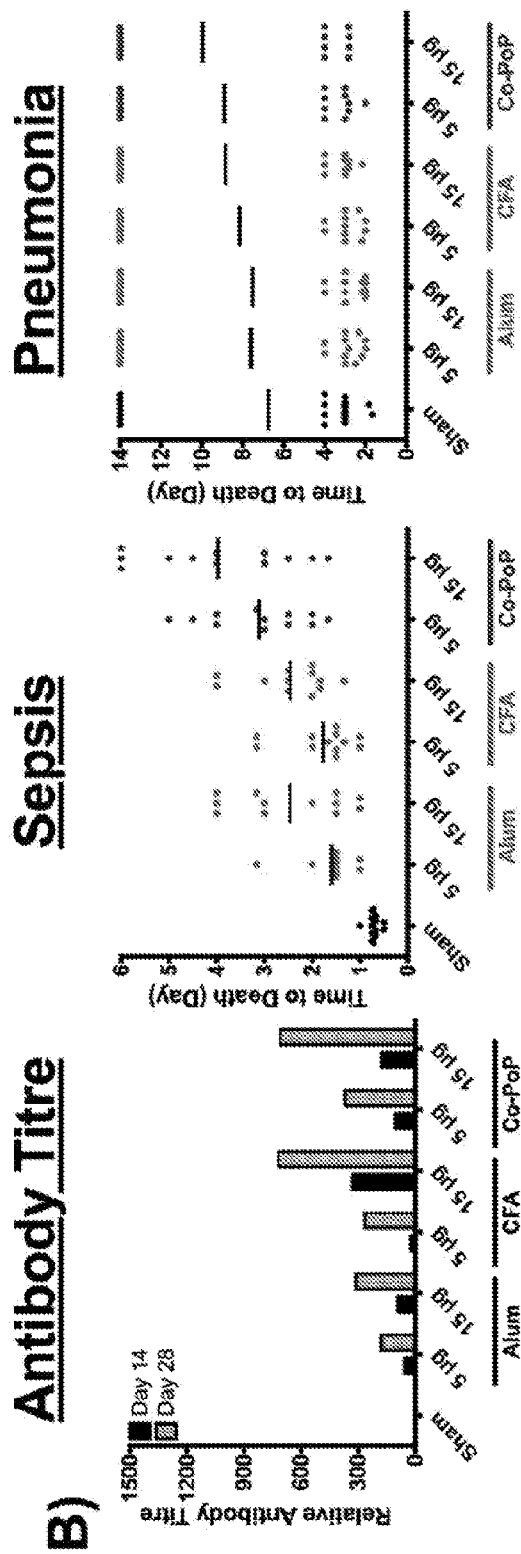
Figure 6:
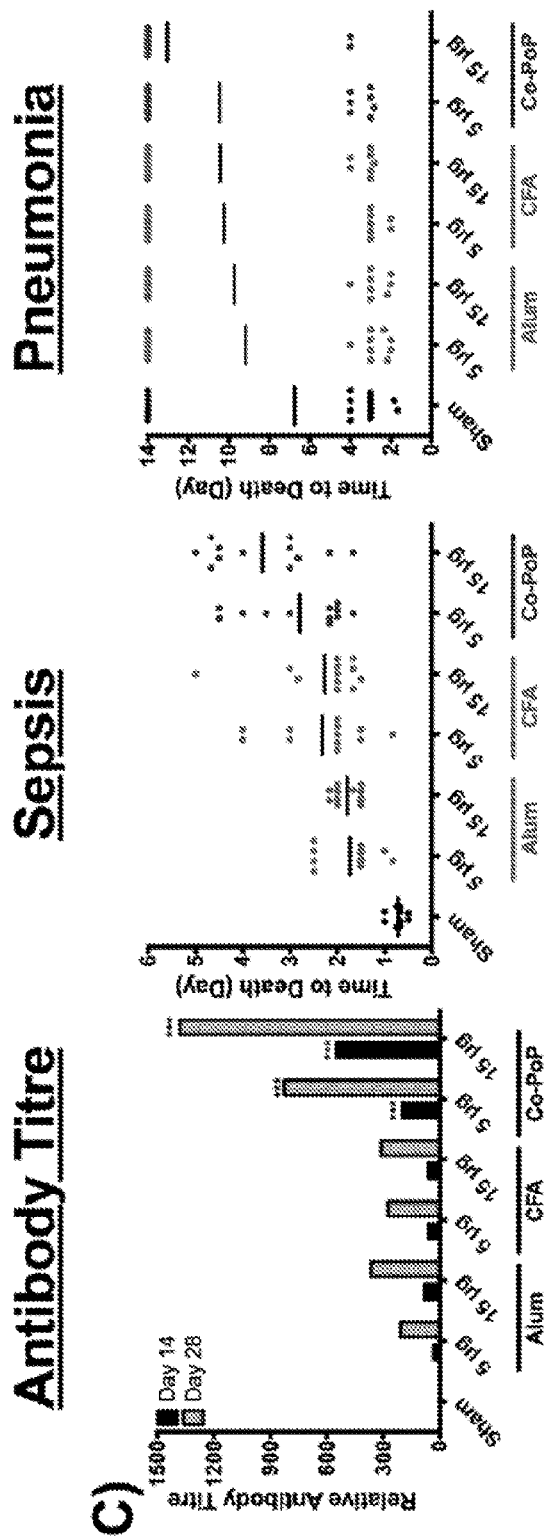
Figure 7:
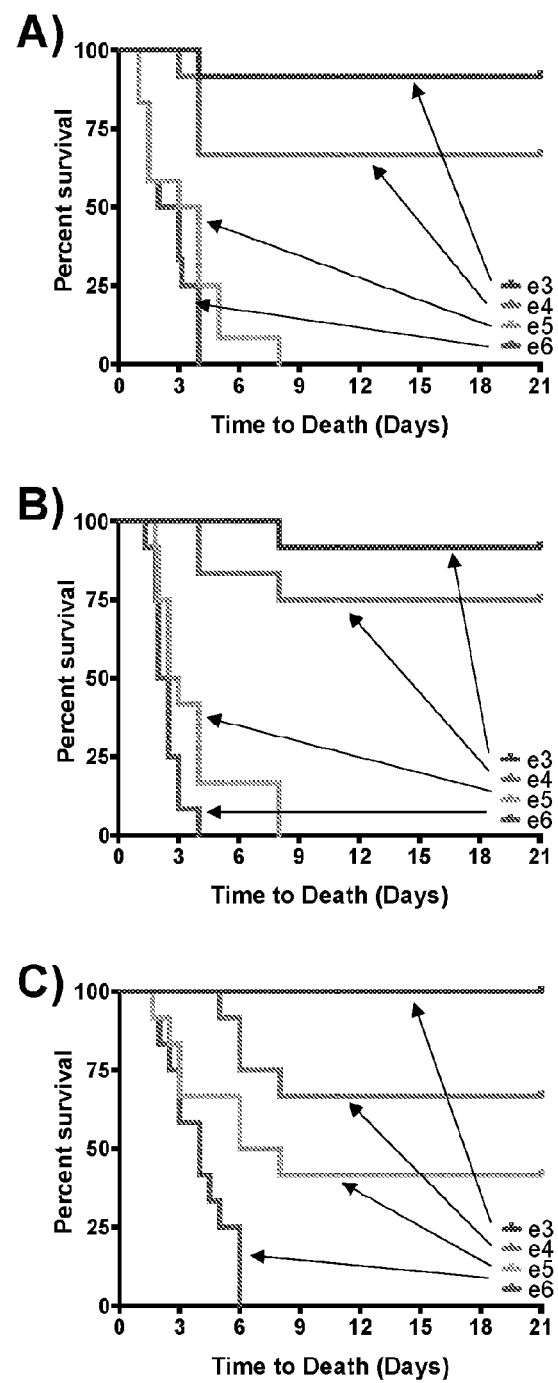
FIG. 7. Challenge dosing of D39. (A) Alum, (B) complete Freund's adjuvant, and (C) Co-PoP were formulated with 15 µg of PspA protein and challenged with four levels (for example, e3=$1 \times 10^3$ cells) of planktonic D39 in a sepsis model.

The delivery of GlpO and PncO, both recombinantly produced with 6× histitine tags, was facilitated using a novel cobalt porphyrin-phospholipid (Co-PoP) liposomal carrier capable of surface-orienting peptide-based antigens for enhanced immune responses and featuring an in-built adjuvant component (monophosphoryl lipid A) that outperformed comparative formulations featuring traditional alum and complete Freund's adjuvant (FIGS. 5-7). The liposomal device thus offers a unique vaccine formulation based upon a simple and stable antigen-carrier complex without the need for advanced chemical conjugation. Furthermore, the technology is well-aligned with the antigen discovery and production techniques offered by the aforementioned biofilm model and well-established recombinant protein production. Therefore, we adopted the technology here in the delivery and assessment of GlpO and PncO. Looking forward, the Co-PoP delivery platform offers even more potential in the way of unprecedented valency of antigens discovered (i.e.,

TABLE 1

Antigen cloning summary

| Antigen Gene | Primers | Source | Restriction Sites | Plasmid | Name |
|---|---|---|---|---|---|
| dexB | F: TAAGCACATATGCAAGAAAAATGGTGGCAT AATGCCGTAG (SEQ ID NO: 3) <br> R: TAAGCACTCGAGTTCCACACAGAAAGCATC CCA (SEQ ID NO: 4) | D39 | NdeI/XhoI | pET21c | pCJ05 |
| htrA | F: TAAGCACCATGGGGAAACATCTAAAAACAT TTTACAA (SEQ ID NO: 5) <br> R: TAAGCACTCGAGAGATTCTAAATCACCTGA AC (SEQ ID NO: 6) | D39 | NcoI/XhoI | pET20b | pCJ06 |
| glpO | F: TAAGCAGAGCTCGAATTTTCAAAAAAAACA CGTGAATTGTC (SEQ ID NO: 7) <br> R: TAAGCACTCGAGATTTTTTAATTCTGCTAA ATCGTTGTTAG (SEQ ID NO: 8) | D39 | SacI/XhoI | pET21c | pCJ07 |
| stkP | F: TAAGCACATATGATCCAAATCGGCAAGATT TT (SEQ ID NO: 9) <br> R: TAAGCAGCGGCCGCAGGAGTAGCTGAAGTT GTTTTA (SEQ ID NO: 10) | D39 | NdeI/NotI | pET21c | pCJ08 |
| blpB | F: TAAGCACCATGGGGAATCCTAATCTTTTTA GAAG (SEQ ID NO: 11) <br> R: TAAGCACTCGAGATCAGAATGGGTTAAAAT TTTA (SEQ ID NO: 12) | D39 | NcoI/XhoI | pET20b | pCJ09 |
| pncO | F: TAAGCACATATGAAAAAGTATCAACTTCTA TT (SEQ ID NO: 13) <br> R: TAAGCACTCGAGCCCCAAGACCCTATGTAG AAAA (SEQ ID NO: 14) | EF3030 | NdeI/XhoI | pET21c | pCJ10 |
| prtA | F: TAAGCAGAGCTCAAAAAAAGCACAGTATTG TC (SEQ ID NO: 15) <br> R: TAAGCACTCGAGATCTTGATTTTTTTCTT CAAT (SEQ ID NO: 16) | D39 | SacI/XhoI | pET21c | pCJ12 | the surface localization and presentation of 100 s of additional protein or peptide antigens) and emphasizes the point here that even if relevant antigens are identified, their ultimate potency may not be realized unless effective delivery methods are employed.

Figure 3:
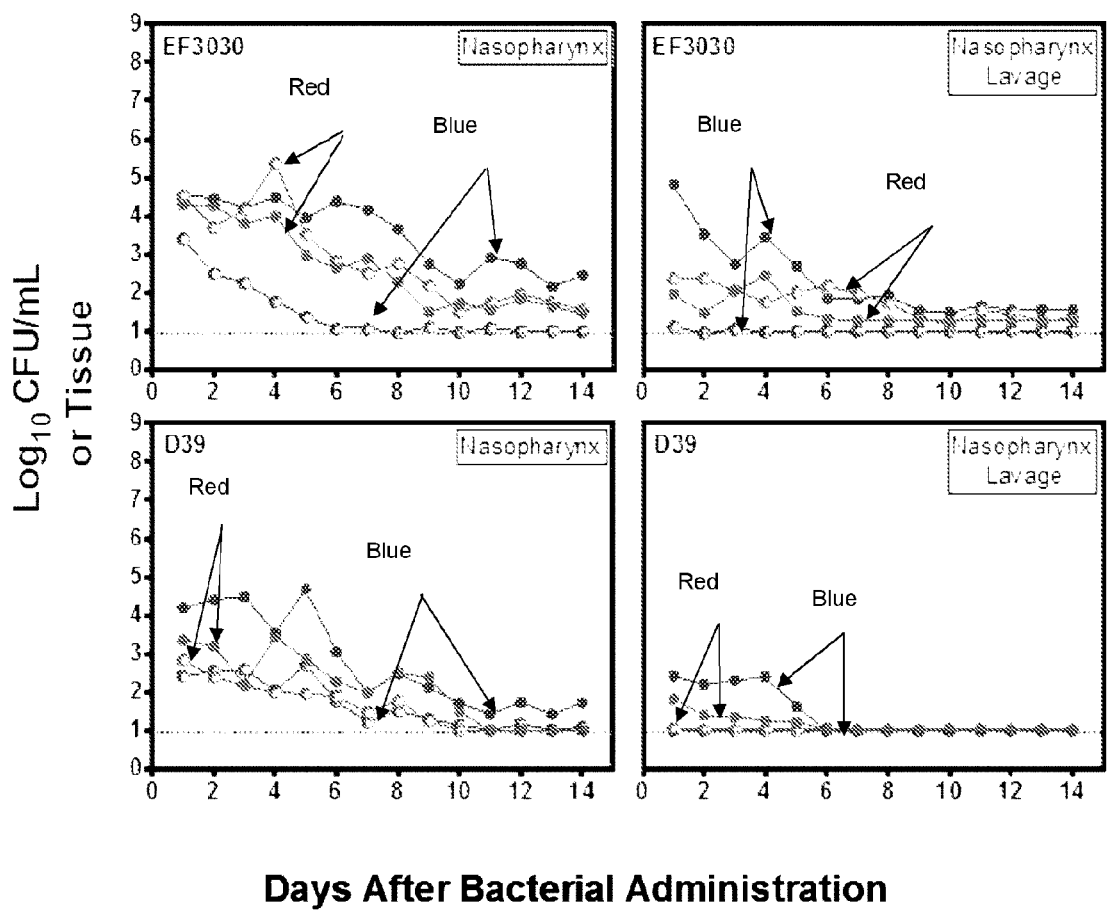
FIG. 3. Directed clearance of biofilm-released bacteria and protection against mouse-passaged challenge strains. (A) Bacterial burden at various anatomical sites was determined daily in unimmunized (filled circles) and GlpO+PncO immunized (open circles) mice. Mice were inoculated intranasally without anesthesia with planktonic (red) or heat-released (blue) EF3030 or D39 bacteria. Protective capabilities of GlpO+PncO immunization were further evaluated in sepsis (B) and pneumonia (C) models with established mouse-passaged pneumococcal bacteria. Dotted lines represents limit of detection for bacterial counts. For (B) and (C), for each set, the first group of dots from the left represents Sham and the second group of dots from the left represents GlpO+PncO. In B, and C, for each group of dots, thick bars indicate mean.
Figure 3:
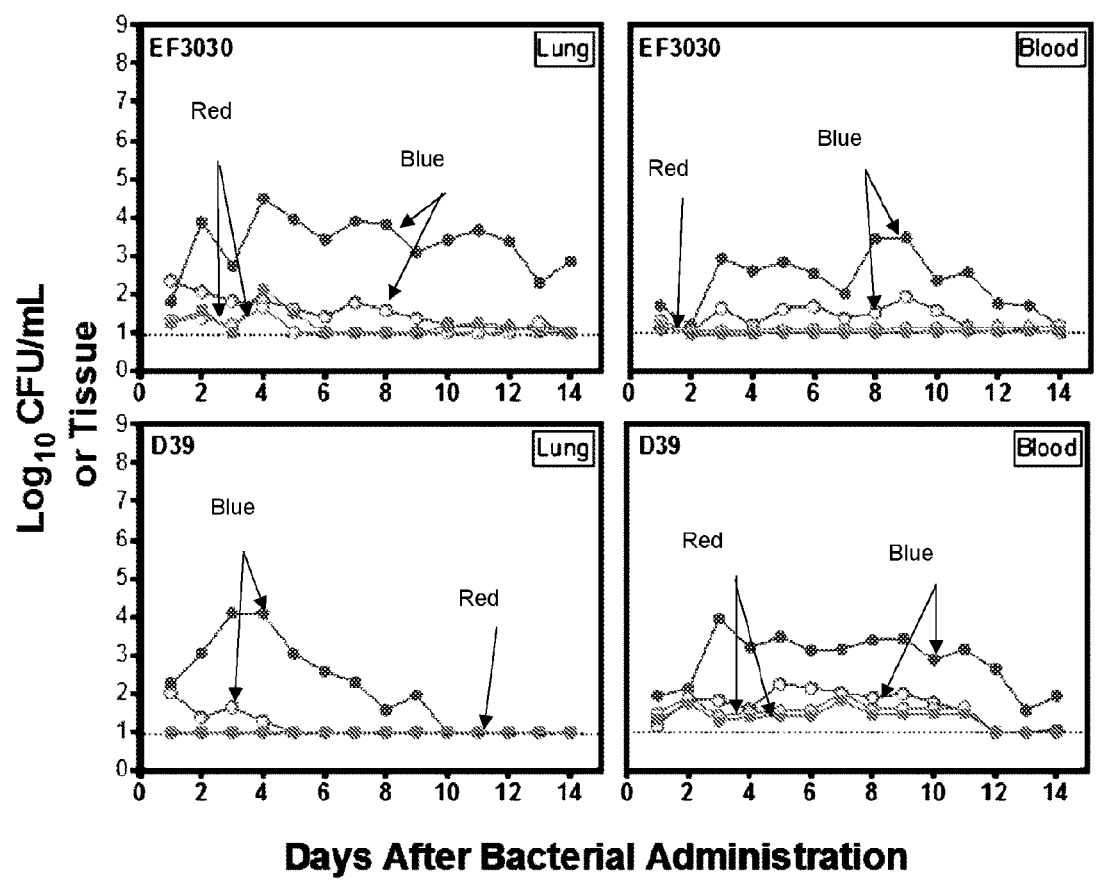
Figure 3:
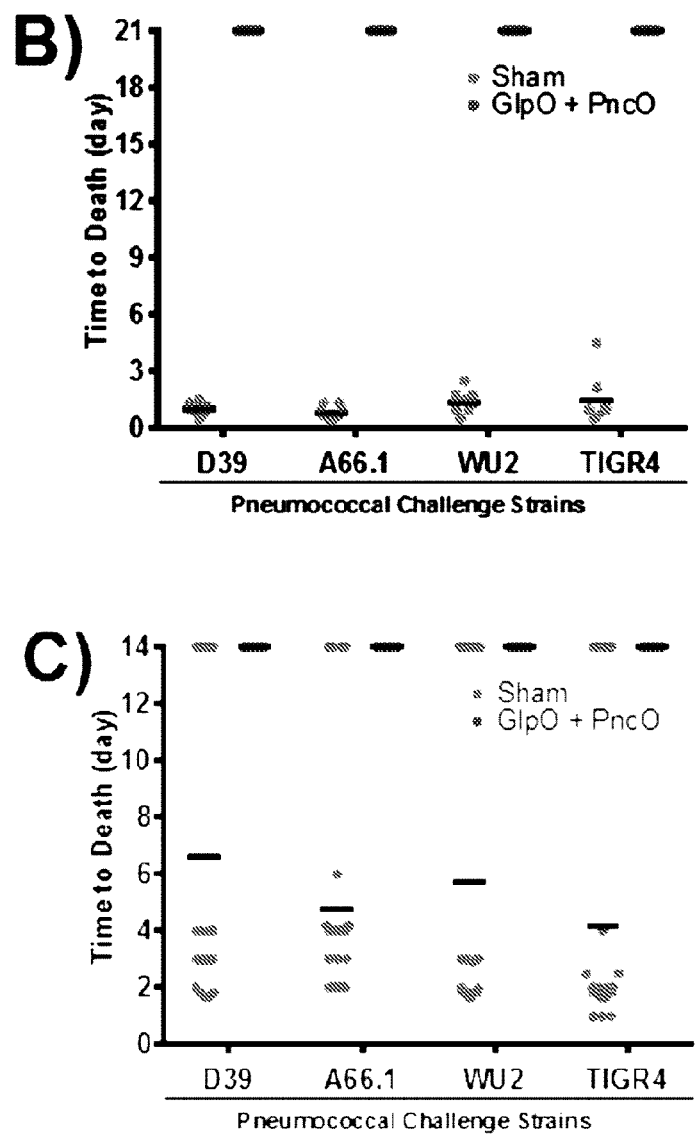

The directed nature of the new antigens was then tested in a series of experiments presented in FIG. 3A. Across different anatomical locations representative of bacterial colonization (nasopharynx) and displacement (nasopharynx lavage), disseminating pneumonia (lung), and invasive septicemia (blood), vaccinated and non-vaccinated mice were challenged with less virulent (planktonic) and virulent (biofilm-released) S. pneumoniae and bacterial clearance monitored over time. In the absence of an external stimulus (e.g., viral infection), mice will remain colonized with planktonic D39 or EF3030 for 1 to 3 weeks without infection of the lower respiratory tract or the development of bacteremia. However, biofilm-released bacteria will demonstrate a similar colonization pattern as compared to avirulent bacteria but will also have the propensity to disseminate into secondary anatomical sites and cause disease. Thus, in this study the planktonic EF3030 and D39 cells provided a clearance baseline to compare reduced bacterial loads using virulent challenge. Clearance of biofilm-released bacteria was only mediated in vaccinated mice; whereas, the bacterial load was significantly increased and lethal in non-vaccinated mice (FIG. 3A). Interestingly, the rate of clearance of planktonic bacteria was unchanged despite vaccination. Thus, the data further support a directed vaccination strategy using GlpO and PncO.

Figure 8:
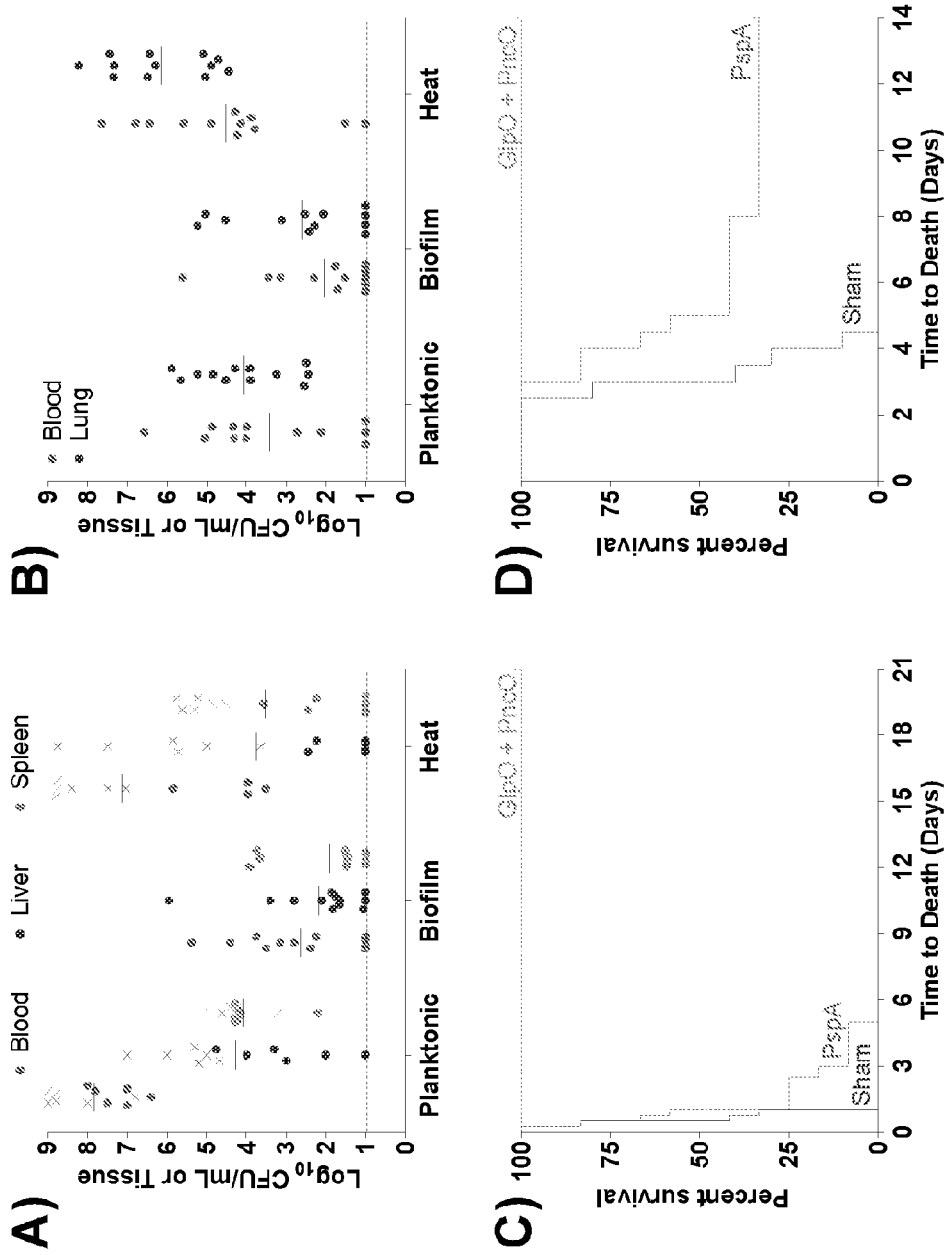
FIG. 8. Characterization of biofilm-released D39 bacteria virulence and vaccine protective capabilities. Bacterial burden was determined for pneumococcal populations after (A) intraperitoneal injections (sepsis model) or (B) intranasal aspiration after anesthesia (pneumonia model). Mice were inoculated with planktonic (broth grown), biofilm-associated, or biofilm-released D39. Each dot in the graphs represents an individual mouse; an "X" represents a mouse that became moribund and required euthanasia before the end of the experiment. Time to death assessment of mice inoculated with heat-released bacteria from the sepsis (C) and pneumonia (D) models after immunization with either PspA or GlpO+PncO. Dotted line represents limit of detection for bacterial counts. In (A), for each set, the first group of points (both dots and crosses) from left represents Blood, the second group of points (both dots and crosses) represents Liver and the third group of points (both dots and crosses) represents Spleen. In (B), for each set, the first group of points (dots) from left represents Blood, the second group of points (dots) represents Lung. In A and B, for each group of dots, thick bars indicate mean.
Figure 9:
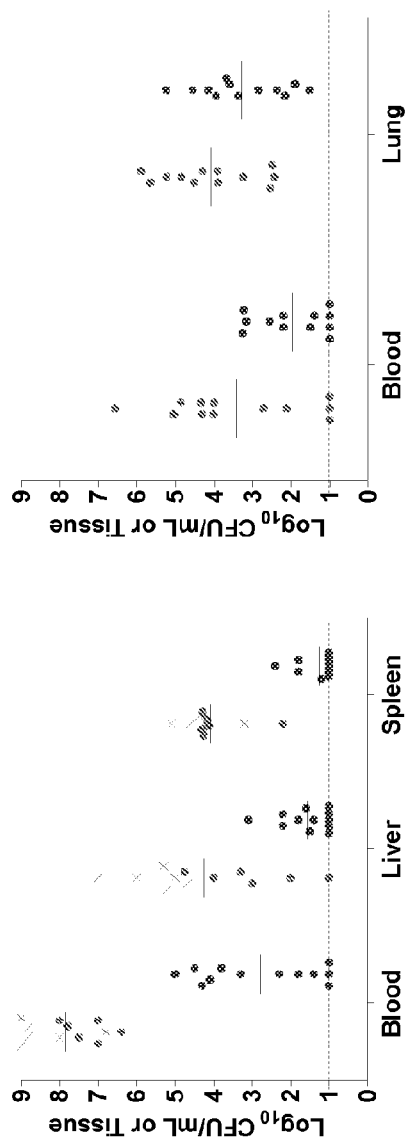
FIG. 9. Bacterial burden associated with universal protection against mouse-passaged pneumococcal challenge strains. Mice were immunized with GlpO+PncO s.q. and challenged with planktonic (A) D39, (B) A66.1, (C) WU2, and (D) TIGR4 cells in either a sepsis or pneumonia model. Each dot in the graphs represents an individual mouse; an "X" represents a mouse that became moribund and required euthanasia before the end of the experiment. Dotted line represents limit of detection for bacterial counts. For (A), (B), (C), and (D) in each set, for both Sepsis and Pneumonia, the first group of dots from left represents Sham, and the second group of dots from left represents GlpO+PncO. For each group of dots, thick bars indicate mean.
Figure 9:
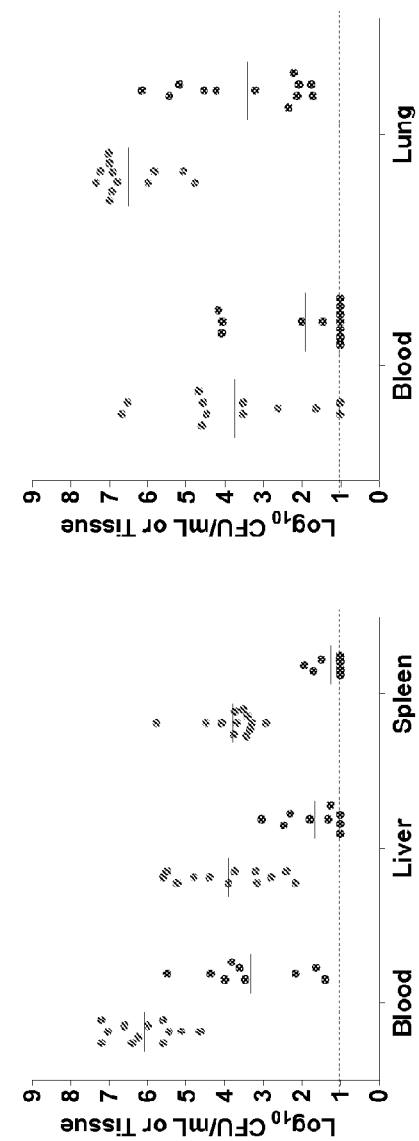
Figure 9:
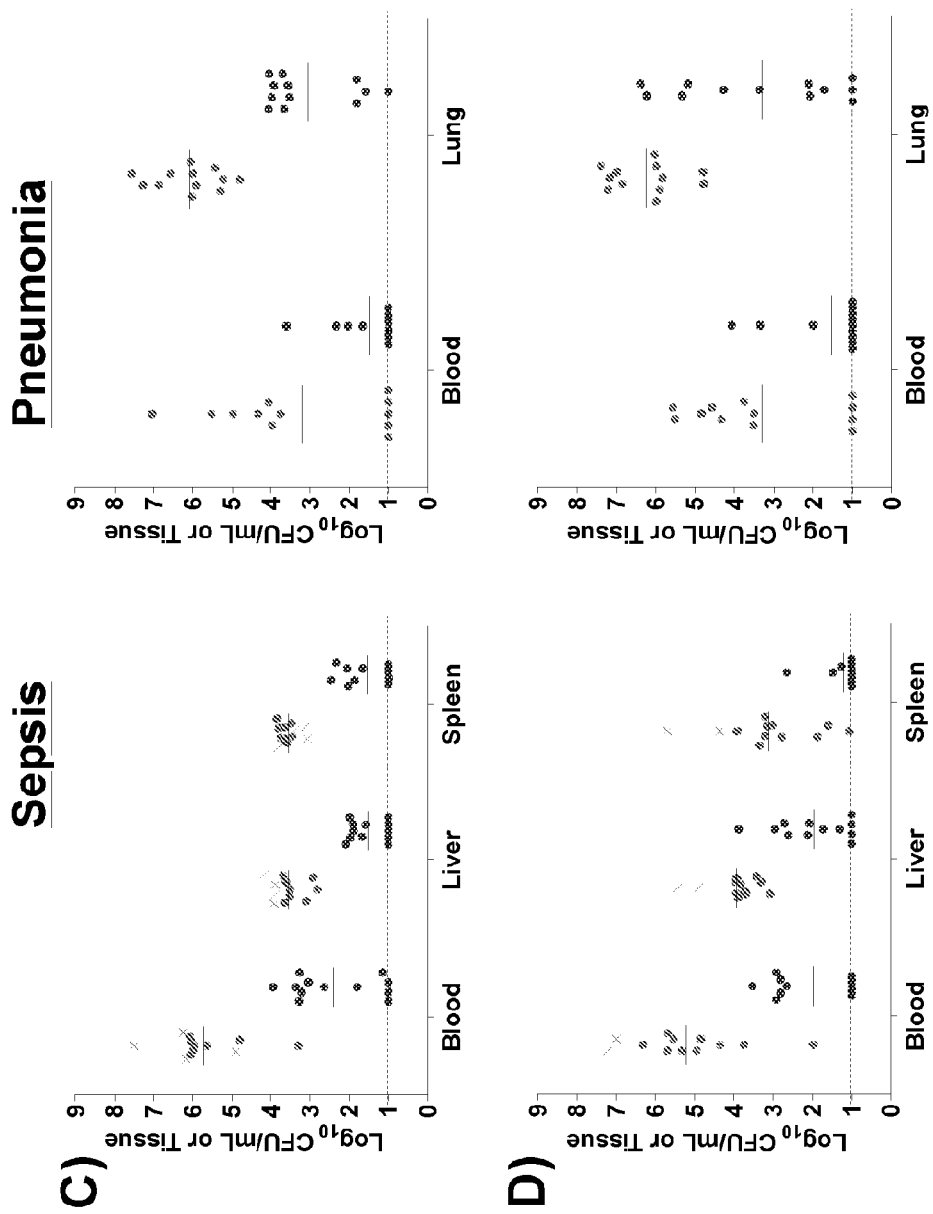
Figure 10:
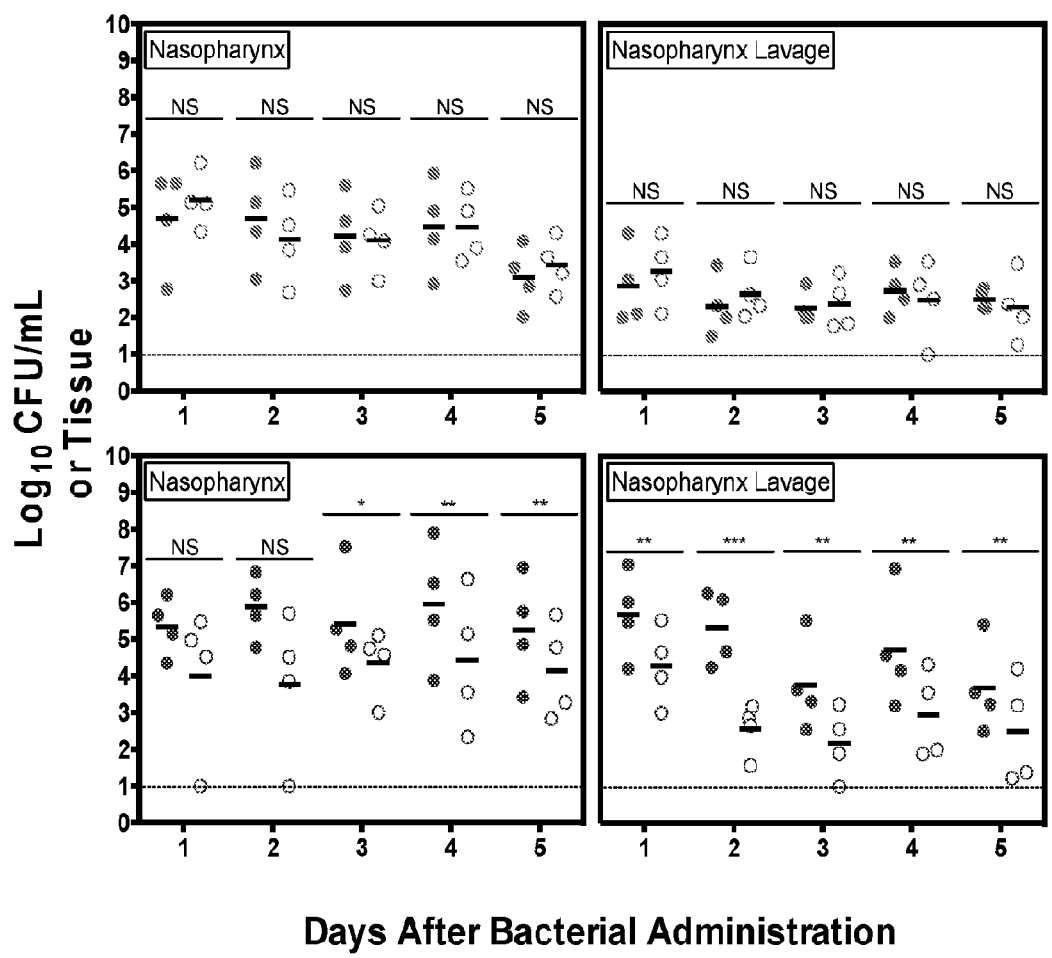
FIG. 10. Characteristics of directed clearance of virulent released bacteria and protection against an expanded set of strains. (A) Directed clearance of biofilm-released bacteria of passively immunized mice. Bacterial burden at various anatomical sites was determined daily in unimmunized (filled circles) and GlpO+PncO passively immunized (open-circles) mice. Mice were inoculated intranasally without anesthesia with planktonic (top row) or heat-released (bottom row) EF3030. Protective capabilities of GlpO+PncO immunization was further evaluated in the sepsis (B) model using an expanded set of mouse pneumococcal strains. Dotted line represents limit of detection for bacterial counts. *$P<0.05$, $P<0.01$, and *$P<0.001$. For (B), in each set, the first group of dots from left represents Sham, and the second group of dots from left represents GlpO+PncO. For each group of dots, thick bars indicate mean.
Figure 10:
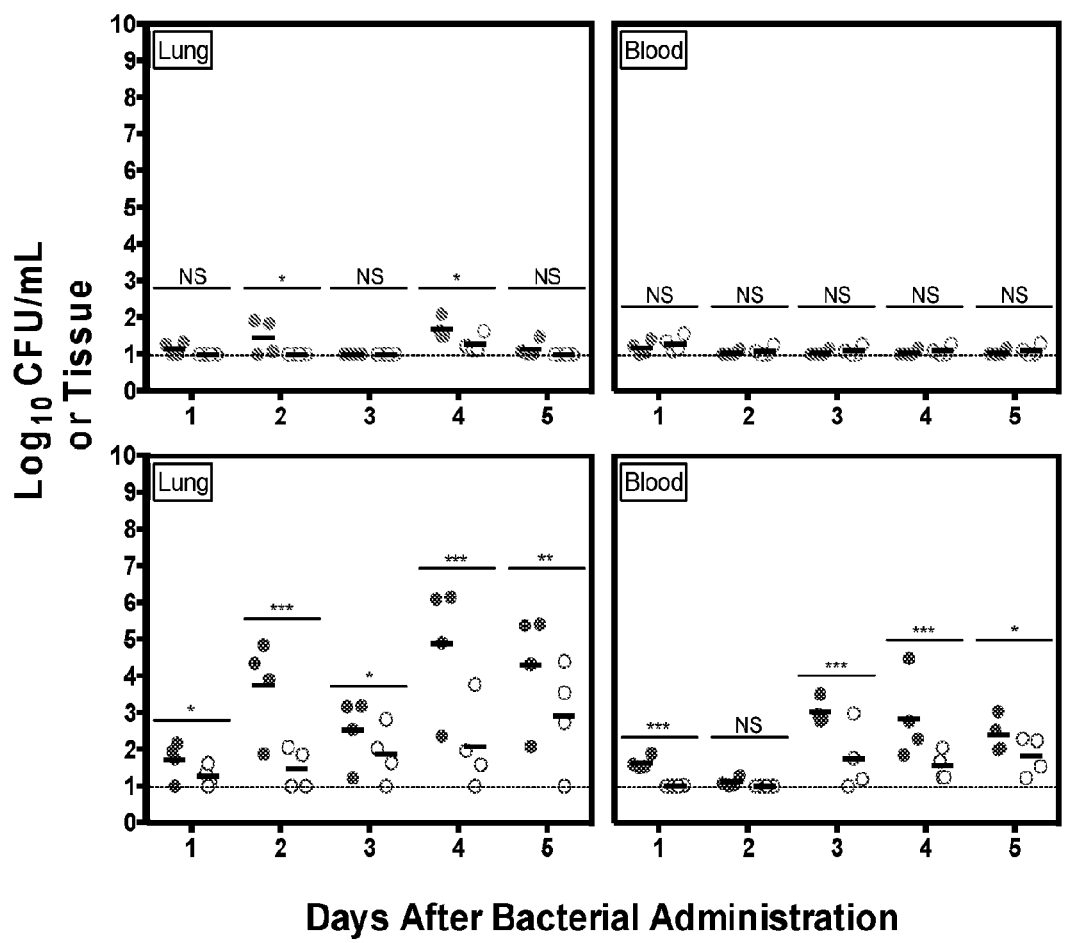
Figure 10:
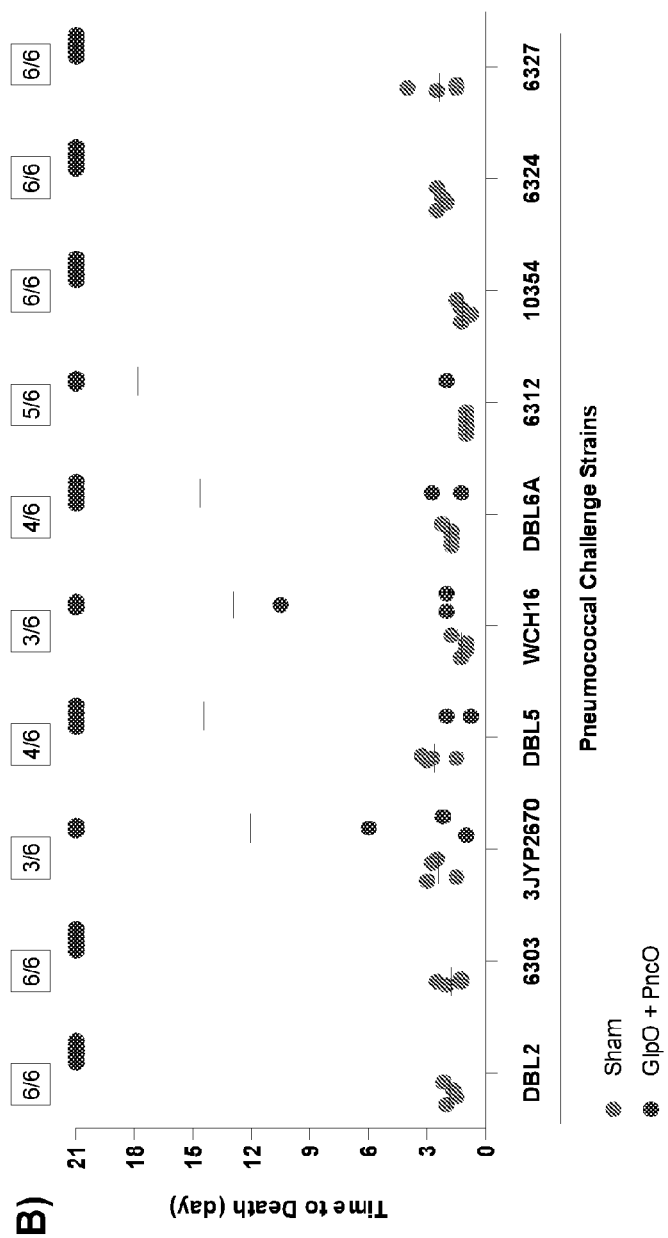

However, the antigenic drift potential of S. pneumoniae emphasizes the need for any new antigens to be general and effective across a wide range of challenge strains (Table 2). To this end, the new antigens were tested in mice infected with a range of S. pneumoniae strains chosen for their notable difficulty to protect against and the variability between strains with regard to serotype and genetic background. Complete protection was provided for both sepsis and pneumonia challenge models (FIGS. 3B&C; FIGS. 8&9). Ten additional strains were tested in protection experiments with average time to death ranging from 12-21 days as opposed to <3 days for controls (FIG. 10). These challenge assays included strains of serotype 12, 15B, and 27 that are not covered by current vaccines and suggest that 1) strains currently circulating and causing disease in the population can be protected against with this vaccine composition and 2) the methodology of in vitro biofilm-release can be used to produce mouse-virulent bacterial populations useful for future vaccine protection screening. The combined results emphasize a degree of coverage not previously reported when using a protein-based antigen with the added potential to continually identify and test new antigens in response to disease variation over time. Finally, broad protection is supported by a sequence conservation analysis of the new antigens across S. pneumoniae serotypes (Table 3). The results therefore support the widespread protection potential of GlpO and PncO and resistance to antigenic drift.

TABLE 2

S pneumoniae strains used in the current study. Italicized strains are not currently included in commercial vaccines.

| Strain | Capsule Type (Serotype) | Virulence Pattern | Included in Current Vaccines | This Study Protection % |
|---|---|---|---|---|
| D39 | 2 | 1 | Yes | 100% |
| D39 - Heat Released | 2 | 4 | Yes | 100% |
| DBL2 | 2 | 2 | Yes | 10000 |
| A66.1 | 3 | 1 | Yes | 100% |
| WU2 | 3 | 1 | Yes | 100% |
| ATCC6303 | 3 | 2 | Yes | 100% |
| 3JYP2670 | 3 | 2 | Yes | 50% |
| TIGR4 | 4 | 2 | Yes | 100% |
| DBL5 | 5 | 2 | Yes | 66% |
| WCH16 - Heat Released | 6A | 4 | Yes | 50% |
| DBL6A | 6B | 2 | Yes | 66% |
| *ATCC-6312 - Heat Released* | *12F* | *4* | *No* | *84%* |
| *ATCC-10354 - Heat Released* | *15B* | *4* | *No* | *100%* |
| EF3030 | 19F | 3 | Yes | 100% |
| EF3030 - Heat Released | 19F | 4 | Yes | 100% |
| *ATCC-6324 - Heat Released* | *24* | *4* | *No* | *100%* |
| *ATCC-6327 - Heat Released* | *27* | *4* | *No* | *100%* |

| Virulence Pattern Classification | Carriage | Lung Infection | Sepsis | Comments |
|---|---|---|---|---|
| 1 | − | ++ | +++ | Bacteria carries poorly and transitions to the blood wherever placed |
| 2 | ± | ++ | ++ | Bacteria causes strong infection wherever placed; occasionally will transition to the blood and cause death |
| 3 | ++ | +++ | ± | Bacteria carries well and infects locally but unlikely to kill; rarely transitions to the blood and causes death |
| 4 | ++ | +++ | ++ | Bacteria carries well and causes strong infection wherever placed and can transition to the blood |

TABLE 3

PncO and GlpO antigen description and analysis.

| Gene | Size (bp) | Function | Virulent Gene Expression (log2) Relative to Planktonic | Virulent Gene Expression (log2) Relative to Biofilm | Average log2 Fold Change | Surface Accessible | Strain Conservation (% Homology) Full Protein | Strain Conservation (% Homology) Surface Accessible Regions | Strain Conservation (% Homology) Surface Accessible Epitopes |
|---|---|---|---|---|---|---|---|---|---|
| pncO | 690 | Bacteriocin ABC transporter transmembrane protein | 8.5 | 4.8 | 6.6 | Yes | 95% | 93% | 97% |
| glpO | 1,827 | α-glycerophosphate oxidase | 9 | 5.9 | 7.4 | Yes | 99% | 98% | 98% |

Figure 4:
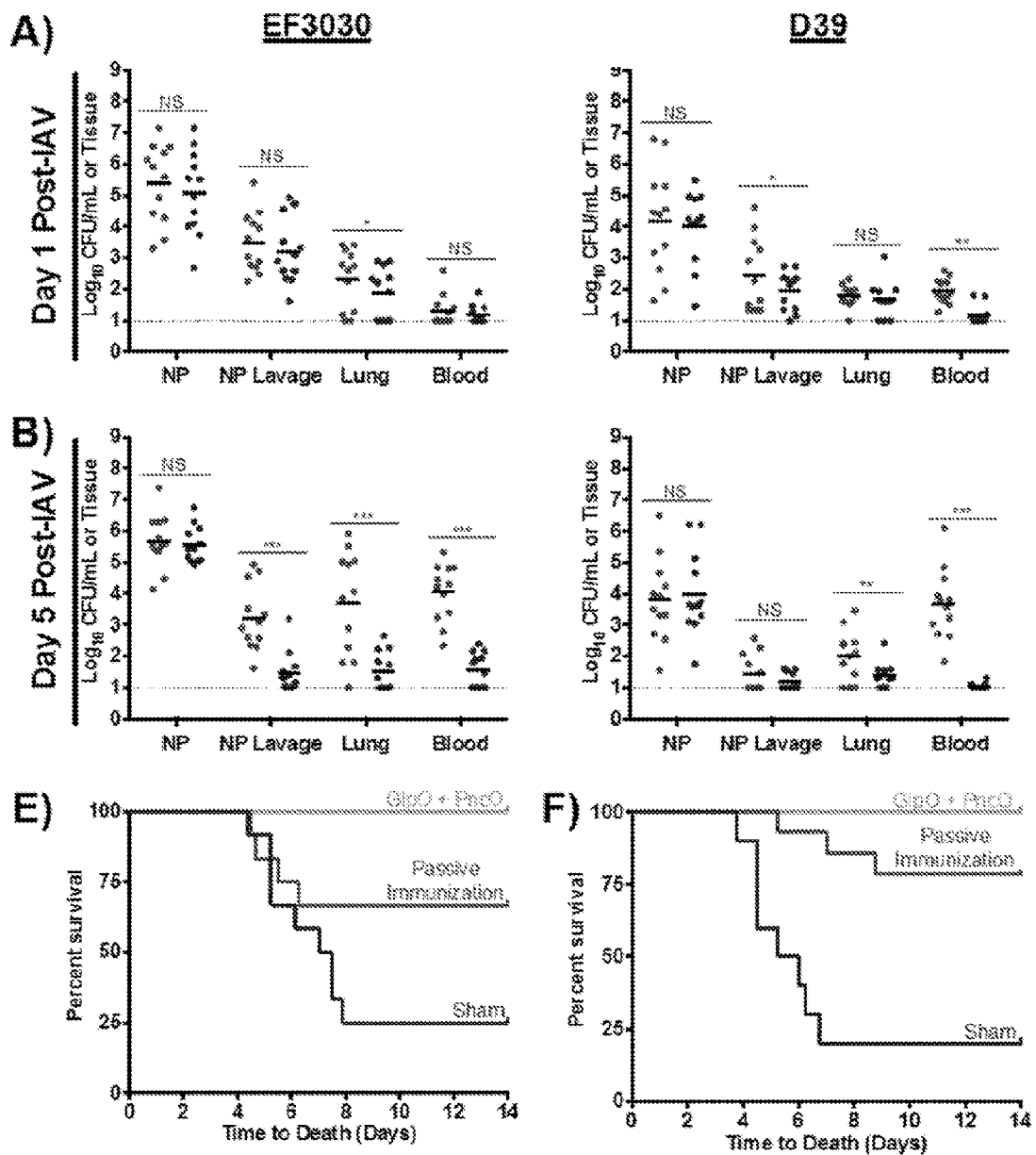
FIG. 4. Bacterial dissemination and time to death assessment of mice stably colonized with pneumococci and triggered with influenza A virus (IAV). Bacterial burden of EF3030 or D39 in unimmunized (red) or GlpO+PncO immunized mice was measured at 1 (A) or 5 (B) days post-infection with IAV. Protective capabilities of traditional or passively GlpO+PncO immunized mice against in vivo IAV-mediated bacterial release of EF3030 (E) or D39 (F). Dotted line represents limit of detection for bacterial counts. *$P<0.05$, $P<0.01$, *$P<0.001$. For A), and B), in each set, for both EF3030 and D39, the first group of dots from left represents Sham, and the second group of dots from left represents GlpO+PncO. In A and B, for each group of dots, thick bars indicate mean.

In a final set of experiments presented in FIG. 4, we explored protection in an in vivo model that mimics the clinical progression of pneumococcal disease onset. Epidemiological evidence suggests that pneumococcal disease is strongly associated with a concomitant infection with upper respiratory tract viruses, such as influenza A virus (IAV). Mice were infected intranasally with IAV 48 hours after colonization with *S. pneumoniae*, a protocol designed to mediate the release of virulent pneumococci from colonizing biofilms for subsequent dissemination to the lungs and blood (FIG. 4A). Mice vaccinated with GlpO and PncO displayed a limited spread of D39 and EF3030 *S. pneumoniae* strains in this clinically-relevant model system with the reduced onset of dissemination of virulent organisms indicated on day 1 post viral infection and significantly pronounced reduction in the lung and the blood on day 5 (FIGS. 4A&B). Of major importance is the fact that the nasopharyngeal burden in immunized and non-immunized animals remained unchanged, suggesting that the harmless and potentially beneficial commensal colonization was unaffected. This further supports a paradigm shift in protection against "accidental pathogens" or those commensals that colonize asymptomatically but have the capacity to cause disease in response to inflammation or other external triggers. When using this same in vivo model of IAV-induced pneumococcal disease, full protection against septicemia and death was conferred by the combination of GlpO and PncO using traditional immunization while partial protection was accomplished via adoptive/passive vaccination strategies (FIGS. 4E&F). The latter result indicates an important role of the humoral immune system arm in the mechanism driving the results obtained throughout this study, while simultaneously suggesting that an additional T cell response is also contributing.

Methods

This study was carried out in strict accordance with the recommendations in the Guide for the Care and Use of Laboratory Animals of the National Institutes of Health. The protocols were approved by the Institutional Animal Care and Use Committee at the University at Buffalo, Buffalo, N.Y. All bacterial inoculations and treatments were performed under conditions designed to minimize any potential suffering of the animals.

Reagents

Bacterial and cell culture media and reagents were purchased from Fisher Chemical and Sigma-Aldrich (St. Louis, Mo.). Chemically defined bacterial growth medium (CDM) was obtained from JRH Biosciences, Lexera, Kans. Sheep blood was purchased from Hemostat Laboratories (Dixon, Calif.). All remaining reagents were purchased from Sigma-Aldrich.

Antigen Preparation

All antigen genes were cloned from the genomic DNA of *S. pneumoniae* strains using primers summarized in Table 1. Each PCR product was then inserted into pET expression vectors as outlined in Table 1 using the flanking restriction sites indicated (designed within the primers). Constructs were verified by colony PCR and restriction digest analysis and were then chemically transformed into BL21(DE3) with resulting single-colony transformants cultured in 3 mL lysogeny broth (LB) at 37° C. with shaking prior to 15% glycerol stock storage at −80° C. Expression was initially confirmed by 3-5 mL LB cultures started from glycerol stocks and cultured at 37° C. with shaking until an $OD_{600}$ of 0.4 was achieved. After which, cultures were induced with isopropyl β-D-1-thiogalactopyranoside (IPTG) (1 mM) for 1 hour. Upon collection via centrifugation, cells were washed twice with PBS and resuspended in 25 mM Tris-HCL prior to boiling with loading dye and expression analysis/confirmation via SDS-PAGE.

Glycerol stocks were then used to start overnight 3 mL LB cultures incubated at 37° C. with shaking and used to inoculate (1% v/v) 1 L of terrific broth, which was then grown to a concentration of 0.4-0.6 $OD_{600}$ under the same culture conditions. IPTG induction (100 µM) occurred at this point prior to continued culture overnight at 22° C. After clarification by centrifugation, cells were resuspended in Buffer A (50 mM $Na_2PO_4$, 500 mM NaCl, and 10% glycerol) and lysed via French press. The resulting lysate was clarified by centrifugation and the resulting lysate supernatant clarified further via ultracentrifugation at 142,000×g (RFC) for 45 minutes. Lysate collected was confirmed by SDS-PAGE at this stage prior to column purification.

Antigen protein products were then purified by passing lysate supernatant through a fast protein liquid chromatography column (GE Healthcare HisTrap HP, 1×1 mL) using 2% Buffer B (50 mM $Na_2PO_4$, 500 mM NaCl, 10% glycerol, and 250 mM imidazole) and 98% Buffer A as the mobile phase. The protein was eluted with 100% Buffer B, and a UV absorbance of 280 nm was used to detect the fractions containing protein in the elution. Those fractions were pooled and protein content characterized by SDS-PAGE and quantified by Pierce™ Micro BCA™ Protein Assay assessment.

Vaccine Formulation and Immunization

Antigen cobalt porphyrin-phospholipid (Co-PoP) liposomal carrier vectors were generated as described previously (Shao et al., Nat Chem 7, 438-446, (2015)). Each injection dose contained 25 μg monophosphoryl lipid A (MPLA) in liposomes comprising DOPC:cholesterol:MPLA:Co-PoP at a molar ratio of 50:30:5:5. After dissolving liposomes in chloroform in a test tube, the solvent was evaporated and the film was further dried under vacuum overnight. Liposomes were then rehydrated with phosphate buffered saline (PBS) and sonicated. Binding ability of new antigens was evaluated by incubating 25 μg of protein with 20 μg of liposomes in 200 μL PBS within a well of a 96-well plate. Fluorescence in the FRET channel (ex: 430 nm, em: 525 nm) was measured periodically with a fluorescence microplate reader (Tecan Infinite II). Data were normalized to the FRET signal for protein without addition of liposomes. Dynamic light scattering was used to evaluate the particle diameter and zeta potential of liposomes containing three concentrations of PspA (0, 5, and 15 m). Once binding was confirmed, antigen was incubated at 4° C. with Co-PoP liposomes overnight before animal injection. FIGS. 5-7 summarize liposomal carrier characterization and immunization optimization with model antigen PspA.

Outbred 6-week-old female CD-1 mice (Harlan Laboratories, Indianapolis, Ind.) were used in immunization experiments. Mice were immunized by intraperitoneal injection (i.p.; 200 μL), subcutaneous injection (s.q.; 200 μL), and intranasal aspiration (40 μL). Final antigen (Table 1) doses ranged from 5 to 15 μg in either naked or liposomal format. When combined, PncO and GlpO (Table 3) were administered at 15 μg each. After 14 days, mice were boosted with the same formulations. At day 14 and day 28, serum samples were collected from the mice by retro-orbital bleeding. For passive immunizations, respective sera were diluted ten times and administered via i.p. injection (200 μL).

Bacterial Preparation and Biofilm Release

Bacterial strains used in this study are listed in Table 2 and were initially grown on Todd-Hewitt agar plates supplemented with 0.5% yeast extract and 5% sheep blood and incubated overnight at 37° C. Single colonies were used to inoculate 5 mL Todd-Hewitt broth containing 0.5% yeast extract and incubated at 37° C. to an $OD_{600}$ of 0.6. At this point, bacteria were used for challenge studies after washing one time with and resuspending in PBS.

NCI-H292 epithelial cells were cultured in RPMI-1640 medium in T75 flasks at 37° C. and 5% $CO_2$. After reaching 100% confluency, H292 cells were prefixed in 4% buffered paraformaldehyde at 34° C. for 48 hours followed by three washes with PBS. CDM-grown pneumococci were then seeded onto fixed H292 cells with change of media occurring every 12 hours. Formed biofilms were exposed to heat (38.5° C.) for 4 hours and released cells were then collected by centrifugation, washed and resuspended in PBS, and quantified by $OD_{600}$ measurement. Biofilm associated cells were disrupted by gentle pipetting, collected by centrifugation, washed and resuspended in PBS, and quantified by $OD_{600}$ measurement.

Scanning Electron Microscopy

Biofilms grown in vitro for 48 hours were fixed using 2.5% glutaraldehyde, 0.075% ruthenium red, and 0.075 M lysine acetate in 0.1 M sodium cacodylate buffer (pH 7.2) for 1 h at 22° C. This procedure has been shown to retain carbohydrate structures and improve preservation of biofilm morphology. Samples were washed three times without shaking for 15 min at 22° C. in 0.075% ruthenium red in 0.2 M sodium cacodylate buffer and were then dehydrated with a graded series of ethanol solutions (10, 30, 50, 75, 95, and 100%) at 22° C., with 15 min used for each step. Samples were exchanged into 100% hexamethyldisilazane and allowed to air dry before being mounted onto stubs, carbon coated, and analyzed using an SU70 scanning electron microscope at an acceleration voltage of 5.0 kV (available through the South Campus Instrumentation Center, University at Buffalo, Buffalo, N.Y.).

Challenge Models

To induce sepsis or pneumonia, mice were administered i.p. or i.n. (with isoflurane), respectively, with $1 \times 10^4$ to $1 \times 10^6$ CFU of pneumococci strains (Table 2). To induce colonization, mice were administered $1 \times 10^6$ CFU bacteria i.n. without isoflurane. To mimic influenza-induced pneumonia, pneumococci colonization was followed by intranasal inoculation with 40 plaque forming units of IAV. IAV strain A/PR8/34 (H3N2) (ATCC VR-777) was used, and titers were determined by plaque assays. Mice were monitored every four hours for signs of morbidity (huddling, ruffled fur, lethargy, and abdominal surface temperature). Mice found to be moribund were euthanized via $CO_2$ asphyxiation and cervical dislocation.

Tissue Bacterial Count

At predefined time points (24 and 48 h post-infection for intraperitoneal and intranasal challenges, respectively) or upon becoming moribund, mice were euthanized (as described above) and a combination of nasopharynx tissue, nasopharyngeal lavage fluid, lung, liver, spleen, and blood samples was collected and bacterial burden determined as described. Briefly, tissue and organ homogenate, lavage fluid, and blood were sonicated to ensure dissociation of bacterial aggregates and then serially diluted on tryptic soy and 5% blood agar plates prior to enumeration. Tissue burden data and associated challenge data are presented in FIGS. 8 and 9.

Antibody Analysis

To characterize antibody titers associated with delivery optimization (FIG. 6), an enzyme-linked immunosorbent assay (ELISA) was performed by coating a 96-well Costar high binding polystyrene plate with 10 μg/mL PspA in tris-buffered saline (TBS) at 4° C. overnight. The plate was blocked with 3% BSA in TBS-Tween 20 (TBS-T) for one hour at 22° C. Sera was diluted into TBS-T in ratios of 1:1,000, 1:5,000, 1:7,500 and 1:10,000 and added to the plate. The plates were then incubated at 37° C. with mild agitation for three hours. The secondary antibody (Anti-Mouse IgG, IgA, IgM (H+L) Highly X-Adsorbed-Biotin) was added to the wells in a 1:1,000 ratio and agitated for two hours. Streptavidin was added to each well in a 1:1,000 ratio and allowed to shake for 30 minutes. The signal was developed with p-nitrophenyl phosphate and the reaction was quenched using 0.75 M NaOH. The signal was detected using a plate reader spectrophotometer at an absorbance of 405 nm.

Disease Incidence Analysis

The data presented in FIGS. 1D, F, and G were obtained from the CDC's Active Bacterial Core Surveillance (ABC) for Streptococcus pneumoniae (cdc.gov/abcs/reports-findings/surv-reports.html). The infection rate for infectious pneumococcal disease was obtained from the annual reports from 1998-2014 for both children under 5 and the total population. The data presented in FIG. 1E was obtained from Table 2 in Richter, et al (2013), which provided information regarding pneumococcal strain prevalence from 1998-2011; the strain distribution for children under 5 was organized into three different groups (PCV-7, PCV-13, and NVT strains). FIG. 1F represents the efficacy of the PCV-7 vaccine by plotting the percent reduction in infection rate following the introduction of the vaccine. The baseline infection rate was determined by averaging the rates from 1998-1999. Similarly, the efficacy of the PCV-13 vaccine (FIG. 1G) was demonstrated by plotting the percent reduction in infection rate using the 2008-2009 infection rates as a baseline. The dashed lines in FIGS. 1F and 1G correspond to the prevalence of the PCV-7 and PCV-13 strains, respectively one year prior to the introduction of the vaccines.

Statistical Analysis

Column comparisons were analyzed for statistical significance using a two-tailed Student t test for unpaired data. Multivariance analysis was done using one-way analysis of variance (ANOVA) that was corrected using the Bartlett variance test and for multiple comparisons using the Bonferroni multiple-comparison test. For both tests, a P value of 0.05 was considered significant. Statistical analysis was performed using the GraphPad Prism software (version 6.0 h.283; GraphPad Software Inc., La Jolla, Calif.). All data resulted from a minimum of three samples with animal experiments using a minimum of four (and in most cases twelve) subjects.

Example 2

In this example, new antigens associated with pneumococcal disease virulence were utilized as a basis for testing the delivery and adjuvant capabilities of a hybrid biological-biomaterial vector. The hybrid design provides 1) dual passive and active targeting of antigen presenting cells (APCs), 2) natural and multi-component adjuvant properties, 3) dual intracellular delivery mechanisms, and 4) a simple formulation mechanism. In addition, the hybrid device enables device-specific, or in situ, antigen production via the biological component of the vector. This capability eliminates the need for dedicated antigen production and purification prior to vaccination efforts while leveraging the features of the overall delivery device. Here, we present the potent utilization of the vector towards pneumococcal disease highlighted by protective capabilities when tested against a range of clinically-relevant *Streptococcus pneumoniae* strains. More broadly, the results here point to similar levels of success with other diseases that would benefit from the production, delivery, and efficacy capabilities offered by the hybrid vector.

This work features a hybrid antigen delivery vector composed of biological and biomaterial components each designed to facilitate, enhance, and direct the immune response process. The biological portion of the vector is a bacterial cell (nonpathogenic *Escherichia coli*) that, as a result of the microbial framework, possesses natural adjuvant properties and also allows the delivery of either protein or genetic antigens. Coating of the bacterial core with a poly(beta-amino ester) (PBAE) covalently linked to mannose provides a combined delivery device with properties to assist antigen cargo cellular translocation. Namely, the size of the overall vector allows passive targeting of phagocytic APCs programmed to engulf such particles; in addition, the vector's composition and the surface characteristics endowed by the mannosylated PBAE will engage APC receptors and enhance uptake upon vector administration. The biomaterial and biological components can also be designed to facilitate endosomal escape and cytosolic trafficking post-phagocytosis. Finally, the bacterial core of the vector allows antigen cargo to be delivered as protein, nucleic acid, or both.

This last feature also provides an opportunity to directly generate and maintain the required antigen in lieu of a dedicated bioprocess to produce genetic or protein formats. Thus, the hybrid vector provides the added capability of "in situ" antigen production that can be coupled to the delivery features of the device. Combined, the vector offers a broad array of engineering opportunities meant to improve vaccine production (via rapid and scalable means of component generation, in situ antigen provision, and simple hybrid formulation) and potency (via the innate design and diverse engineering tools, i.e., polymer chemistry and molecular biology).

This premise is the basis for the following results. Within the framework of pneumococcal disease, new antigens were generated and delivered via the hybrid vector. Directed, broad, and potent results were obtained as assessed within disease challenge assays against a range of clinically-relevant *S. pneumoniae* strains. Beyond the protection data collected for this particular disease type, the vector format offers opportunities for other maladies (such as cancer or viral-based infectious disease) similarly expected to require an advanced delivery device capable of supporting a similarly advanced immune response.

Results

Hybrid Vector Assessment with Model and Novel Antigen Delivery

Figure 11:
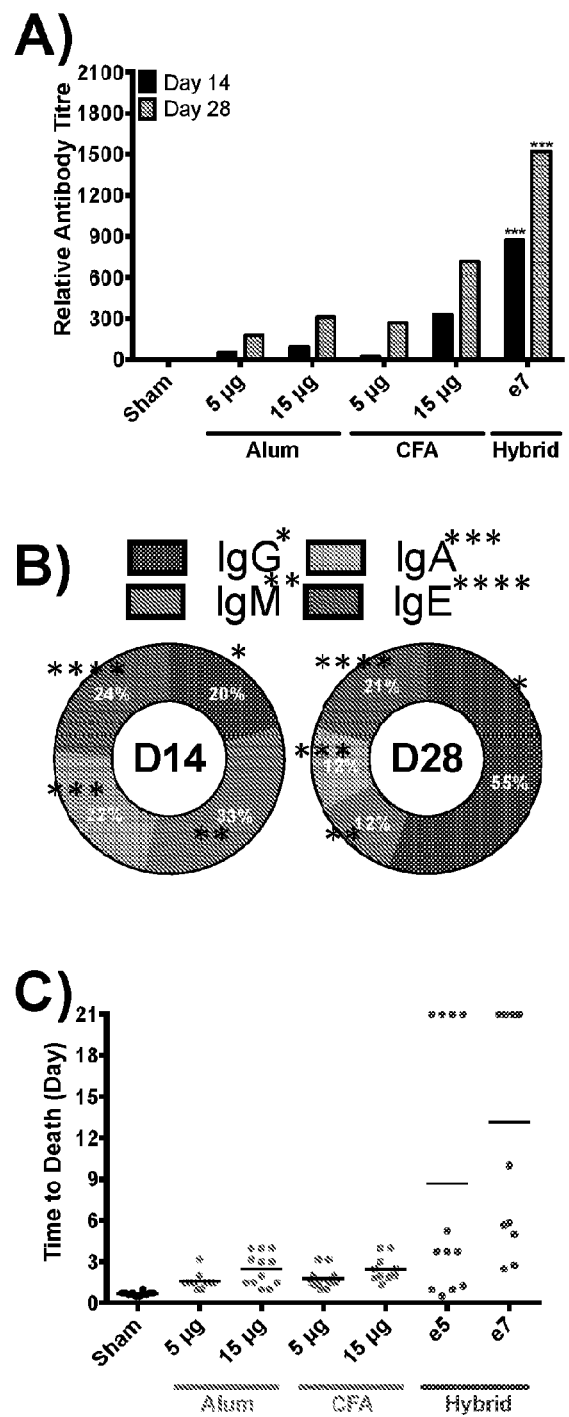
FIG. 11. Characterization and application of the hybrid vector. Comparison of antibody and challenge protection (A, B, and C) when testing with the PspA antigen located either within the hybrid vector or tested in traditional vaccine formulations with alum and complete Freund's adjuvant (CFA). Screening of individual virulent-specific antigens (D) prior to consolidating all antigens to plasmids within the hybrid vector tested within sepsis (E) and pneumonia (F) challenge assays against virulent *S. pneumoniae* strain D39. Vaccination was extended to other clinically-relevant *S. pneumoniae* strains within sepsis (G) and pneumonia (H) models. ***$P<0.001$ relative to controls on associated days. For (G), and (H) in each set, the first group of dots from left represents Sham, and the second group of dots from left represents GlpO+PncO. In C, D, G, and H, for each group of dots, thick bars indicate mean.
Figure 11:
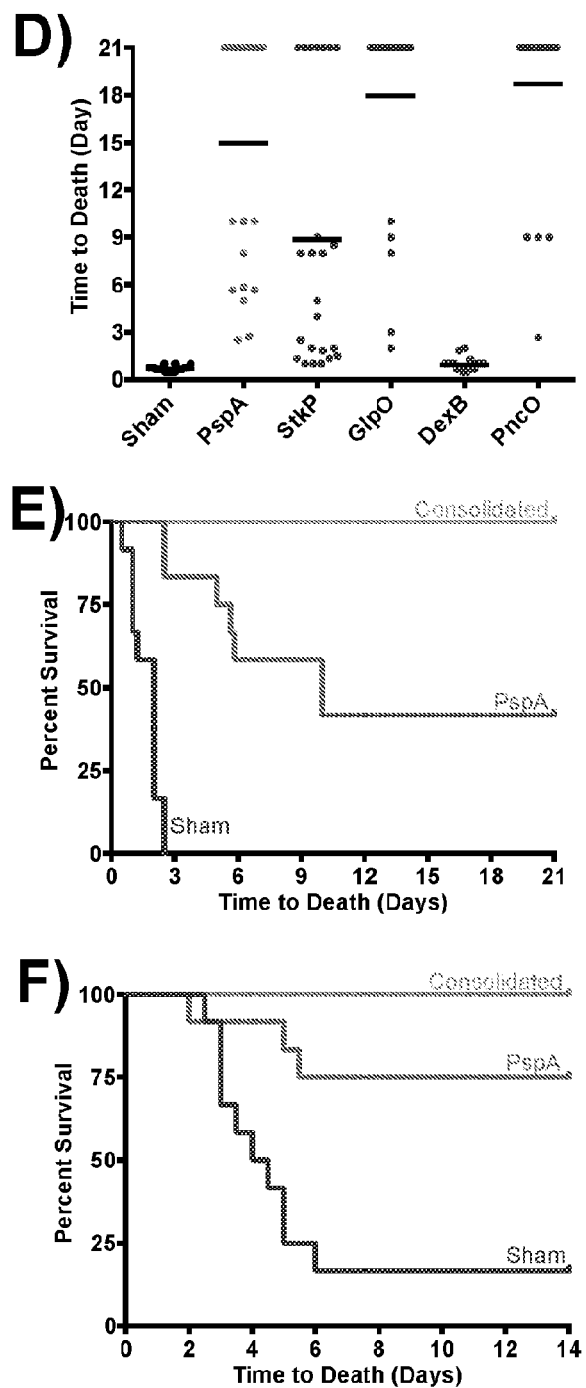
Figure 11:
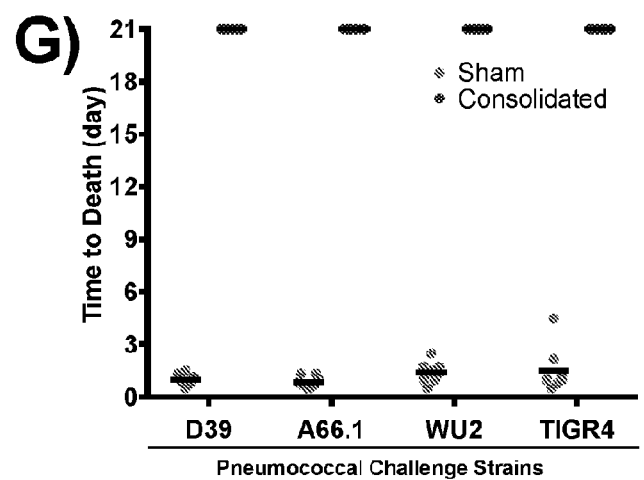
Figure 11:
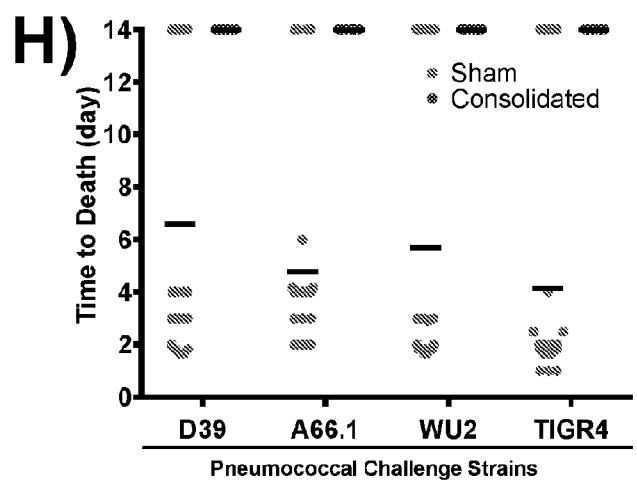
Figure 15:
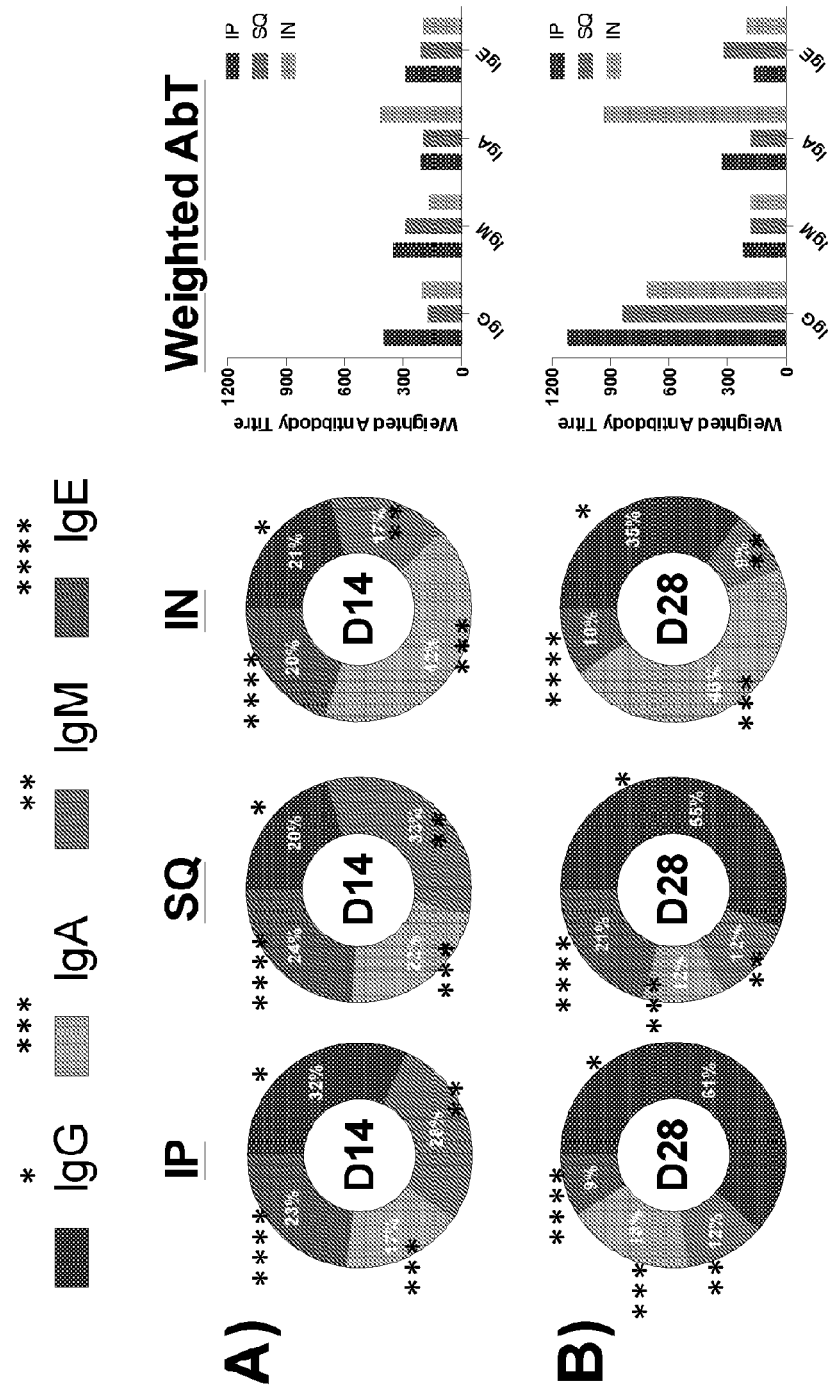

The data presented in this work marks the first application of the hybrid vector and the utility of the device is assessed in the context of pneumococcal disease, which afflicts millions worldwide annually especially resource-limited children and elderly. Initial experiments were dedicated to optimizing and characterizing the use of the hybrid vector when incorporating a model protein antigen for pneumococcal disease, PspA. The results demonstrate improved outcomes when compared to traditional vaccine formulations containing either alum or complete Freund's adjuvant (CFA; FIGS. 11A&C and 14). Importantly, these results were consistent across three different administration routes (intraperitoneal [IP], subcutaneous [SQ], and intranasal [IN]). There was also a balanced antibody response (FIGS. 11B and 15) with a transition over time to enhanced IgG content for IP and SQ administrations and IgG and IgA content for IN administration.

Figure 16:
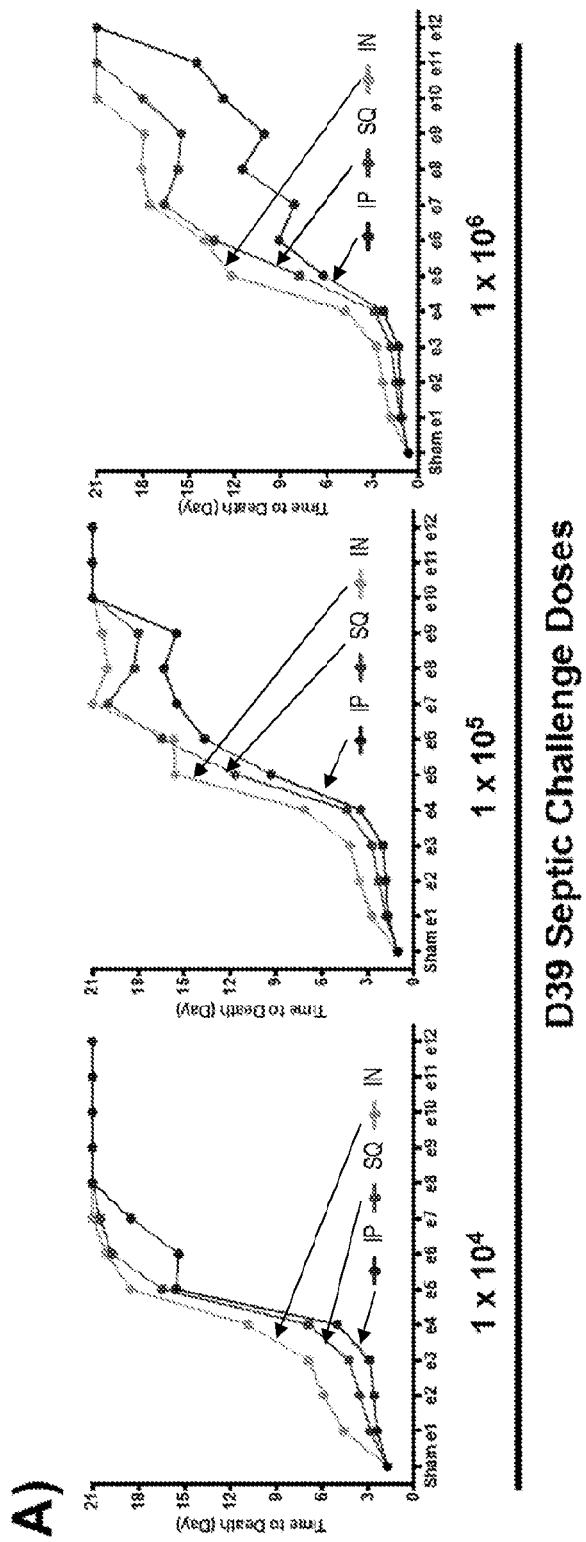
FIG. 16. Dosing and toxicity assessment of hybrid and bacterial vectors. (A) Hybrid vectors expressing PspA were administered at twelve concentrations ($10^1$ to $10^{12}$) either IP, SQ, or IN and challenged with three concentrations of D39 in a sepsis model. (B) Bacterial and hybrid vectors were administered over thirteen concentrations either IP, SQ, or IN and monitored for mouse viability.
Figure 16:
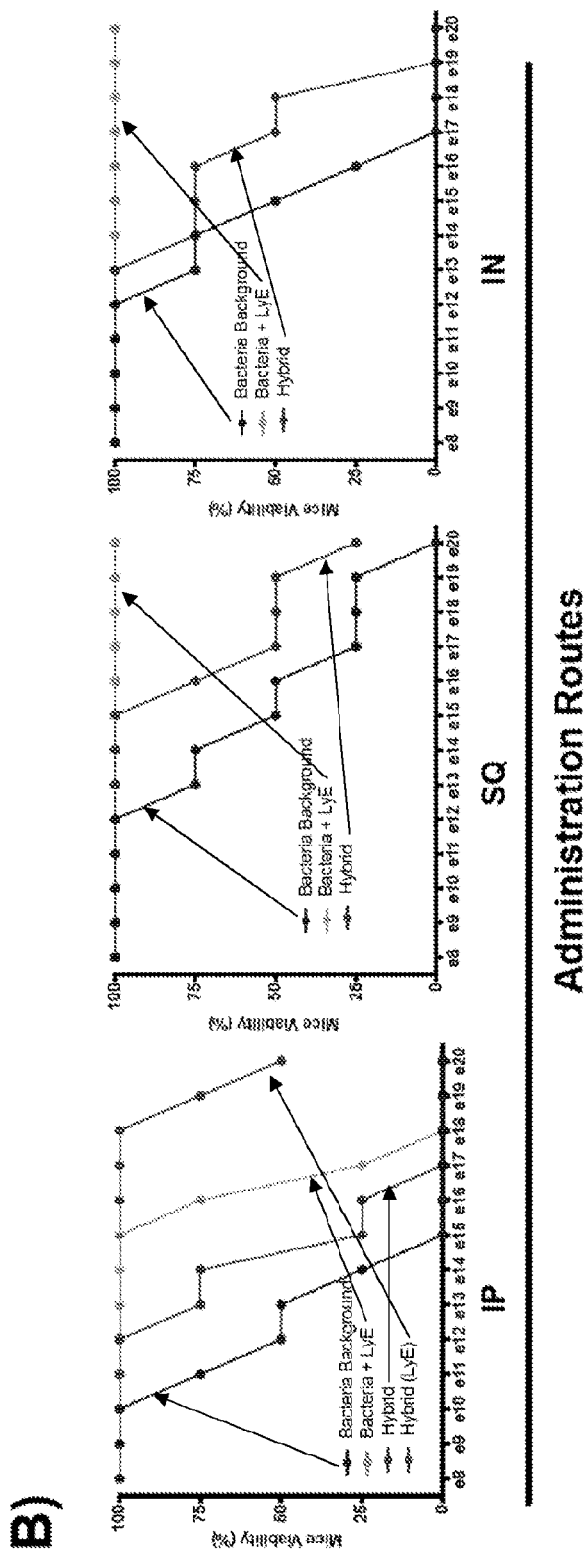
Figure 17:
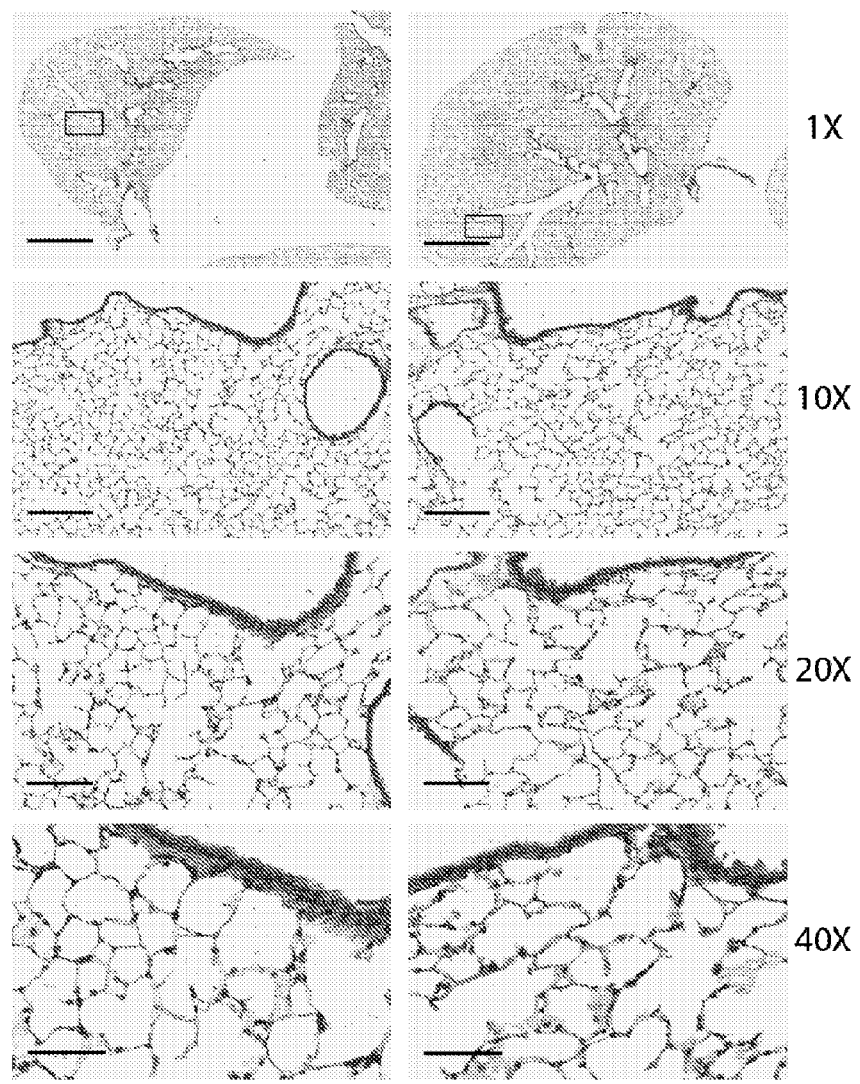
FIG. 17. Histological IN toxicity evaluation of hybrid devices. Specifically, mice were unvaccinated (left column) or vaccinated on days 0 and 14 by IN administration of $10^{13}$ hybrid devices containing the consolidated antigens (right column). On day 28, the mice were challenged with a sham injury (IN instillation of 50 µL normal saline), sacrificed 24 hours later by exsanguination, the lung vasculature flushed, and the lungs fixed. The hematoxylin-eosin-stained 5 µm sections above are from the right cranial lobe of the lungs. The boxes in the 1× images represent the areas that were subsequently acquired at 10×, 20×, and 40×. Scale bars represent 2 mm for 1×, 200 µm for 10×, 100 µm for 20×, and 60 µm for 40×. Both samples display normal histology with no evidence of tissue damage or inflammatory reaction. The bronchial and bronchiolar mucosa and alveoli are intact with typical architecture and no indication of necrosis, edema, or inflammatory infiltrate. Images represent typical findings from all lung lobes from two mice in each group.

Dosing levels of the hybrid vector containing PspA were also assessed and optimized across administration routes and in response to *S. pneumoniae* sepsis challenge using a D39 strain (FIG. 16). D39 was selected because of its notable virulence profile and acceptance as one of the harshest preclinical challenge strains. Increasing the challenge inocula of *S. pneumoniae* can be countered with increasing hybrid vector vaccination dosages (FIG. 16A); however, particularly aggressive challenge levels ($10^6$ *S. pneumoniae* cells) require a vaccination dose of $\geq 10^{10}$ hybrid devices to mediate full protection. Due to the bacterial content of the hybrid vector, it is important to assess such enhanced dosage levels for associated toxicity. Across administration routes, toxicity was not observed until $\geq 10^{13}$ hybrid vectors were administered (FIG. 16B). The design of the hybrid vector, however, allows both the chemical and biological aspects of the device to extend dosing level safety. Namely, the vector's polymer coating and the inclusion of a lysis E (LyE) gene provide alternative mechanisms of attenuation. In the case of LyE, the membrane perforative activity of this protein affords safety of up to $10^{20}$ dose levels for the resulting hybrid device (FIG. 16B). Given the added tissue sensitivity associated with intranasal administration, histology was performed with $10^{13}$ hybrid devices. This administration dose was selected as a result of being the highest delivery load with no associated toxicity. In support of the mouse subject viability tests in FIG. 16B, no tissue damage was observed via histological analysis as compared to the untreated control (FIG. 17).

Figure 12:
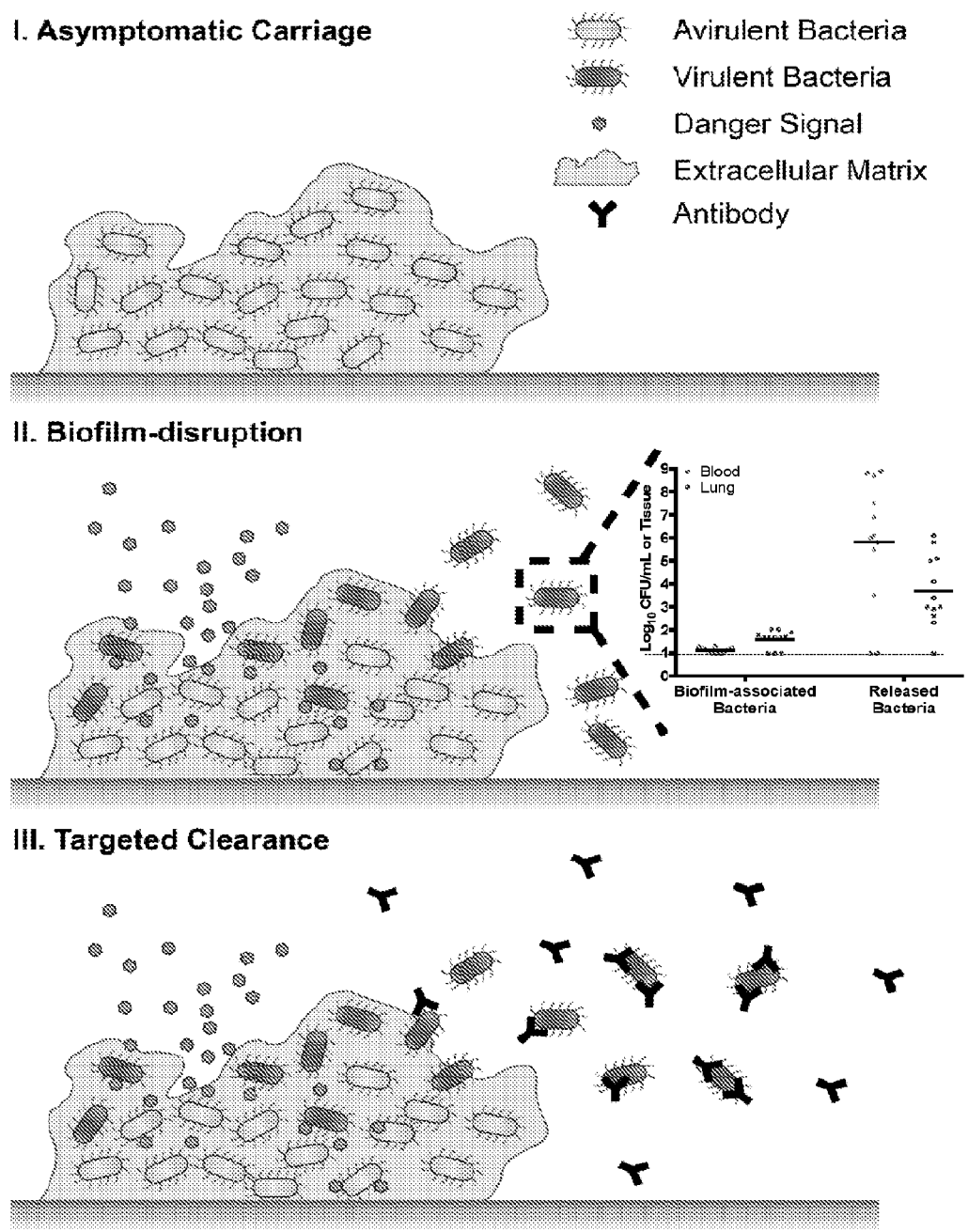
FIG. 12. Overview of pneumococcal disease progression and directed vaccination. Asymptomatic *S. pneumoniae* biofilm carriage is established in the nasopharynx (I) and can be triggered for virulent cellular release (II) and dissemination characterized by extended tissue burden and disease. Highlighting this transition is the inset graph demonstrating that only biofilm-released *S. pneumoniae* spread to surrounding blood and lung locations. In the inset, for each set, the first group of dots from left represents Blood, and the second group of dots from left represents Lung. The antigens delivered with the hybrid vector were chosen to elicit a directed immune response to only the virulent sub-population of *S. pneumoniae* (III).

The hybrid vector was then used to screen several antigen candidates selected due to enhanced expression during *S. pneumoniae* virulence transition during the course of pneumococcal disease progression (Table 4). As such, the antigens would serve as the basis of a "smart vaccine" capable of directing a subsequent immune response to only a virulent sub-set of *S. pneumoniae* cells (FIG. 12). FIG. 11D presents the degree of protection provided by antigen candidates StkP, DexB, GlpO, and PncO relative to PspA, with each individually delivered via the hybrid vector. Though individual protection varied by antigen, the design parameters of the hybrid vector allowed consolidated testing of all the candidates. Specifically, a two expression plasmid system (pCJ10 and pLF; Tables 1&5 and FIG. 18) was utilized to enable the vector-based in situ production of the antigen products while leveraging the delivery capabilities of the hybrid device. Using the two-plasmid system, complete protection was provided against the *S. pneumoniae* challenge strain D39 in both sepsis and pneumonia mouse models (FIGS. 11E&F).

TABLE 4

DexB, GlpO, StkP, and PncO antigen description and analysis.

| Gene | Size (bp) | Function | Virulent Gene Expression (log2) Relative to Planktonic | Virulent Gene Expression (log2) Relative to Biofilm | Average log2 Fold Change | Surface Accessible | Strain Conservation (% Homology) Full Protein | Strain Conservation (% Homology) Surface Accessible Regions | Strain Conservation (% Homology) Surface Accessible Epitopes |
|---|---|---|---|---|---|---|---|---|---|
| dexB | 1,608 | Glucan 1,6-α-glucosidase | 1.5 | 1.5 | 1.5 | No | 98% | N/A | N/A |
| glpO | 1,827 | α-glycerophosphate oxidase | 9 | 5.9 | 7.4 | Yes | 99% | 98% | 98% |
| stkP | 1,980 | Serine/threonine protein kinase | 0.7 | 0.7 | 0.7 | Yes | 99% | 99% | 99.4% |
| pncO | 690 | Bacteriocin ABC transporter transmembrane protein | 8.5 | 4.8 | 6.6 | Yes | 95% | 93% | 97% |

TABLE 5

Consolidated plasmid (pLF) cloning summary

| Antigen Gene | Primers | Source | Restriction Sites |
|---|---|---|---|
| dexB | F: GCGGGATCCCAAGAAAAATGG TGGCATAATGCCGTAG (SEQ ID NO: 17) R: ATAGGCGCGCCTTATAGTAAT TCCACACAG (SEQ ID NO: 18) | pCJ05 | BamHI/AscI |
| glpO | F: GCGGTCGACAAGGAGATATAA TGGAAATTTTCAAAAAAAC (SEQ ID NO: 19) R: GCGGCGGCCGCTTAATTTTTT AATTCTGC (SEQ ID NO: 20) | pCJ07 | SalI/NotI |
| stkP | F: GCGCATATGATCCAAATCGGC AAGATTTTTG (SEQ ID NO: 21) R: GCGCAATTGTTAAGGAGTAGC TGAAGTTGTTTTAG (SEQ ID NO: 22) | pCJ08 | NdeI/MunI |
| pspA | F: ATAGGCCGGCCAAGGAGATAT AATGGAAGAATCTCCCGTAGC CA (SEQ ID NO: 23) R: ATACTCGAGTTATTCTGGGGC TGGAGTTTCTGGA (SEQ ID NO: 24) | pUAB055 | FseI/XhoI |

To demonstrate the potency and versatility of the hybrid vector two-plasmid system, challenge levels and strains of *S. pneumoniae* were varied within vaccine protection assays.

Figure 19:
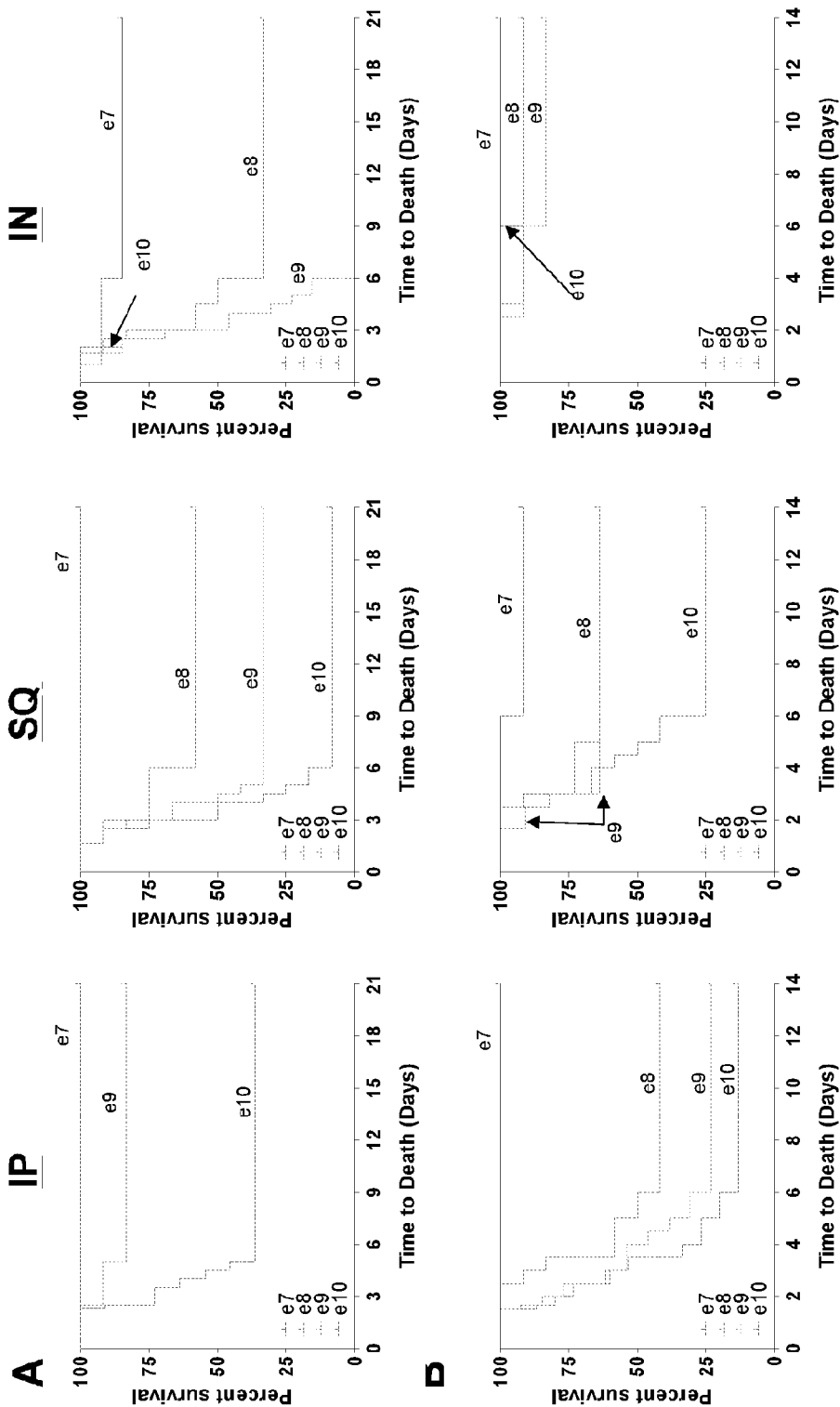
FIG. 19. Challenge dosing of D39. Hybrid vectors expressing antigens PspA, GlpO, PncO, StkP, and DexB were administered IP, SQ, or IN and challenged with four levels (for example, e7=1×$10^7$ cells) of D39 in sepsis (A) or pneumonia (B) models.
Figure 20:
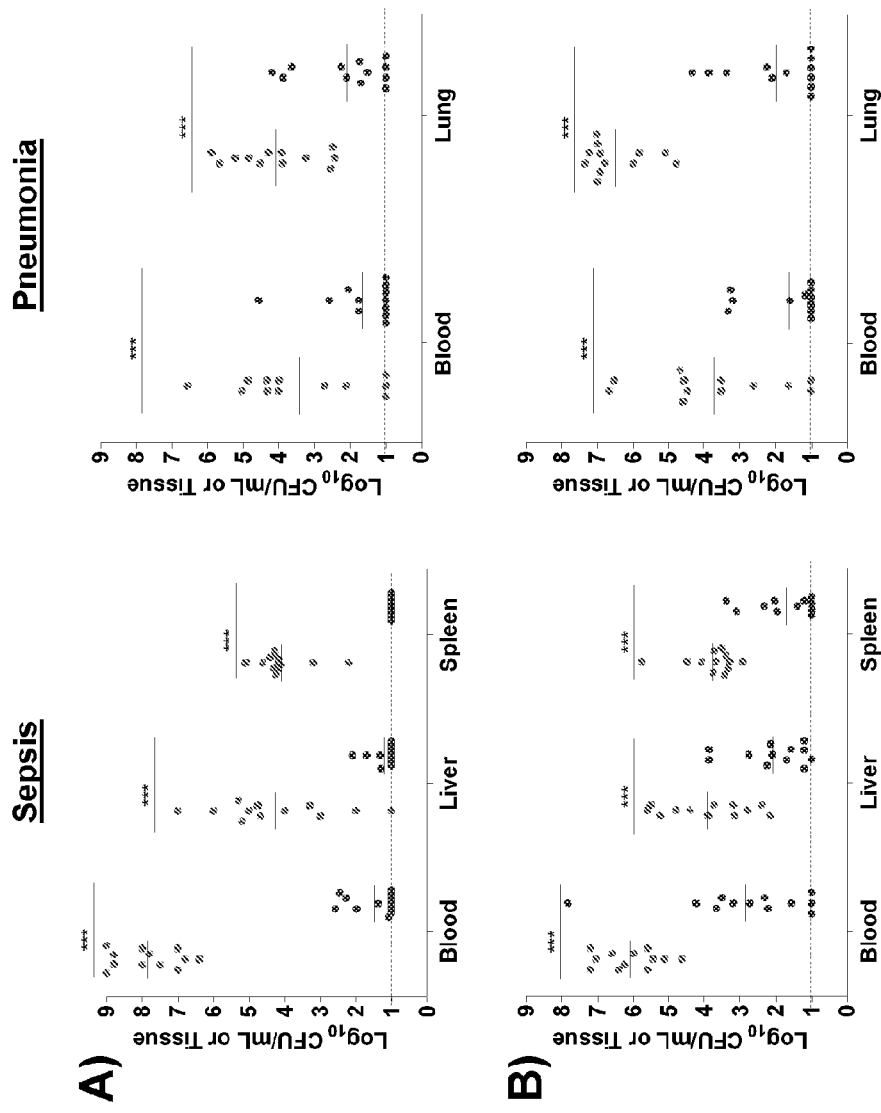
FIG. 20. Bacterial burden assessed for hybrid vector vaccination with the consolidated antigens against pneumococcal challenge strains that included D39 (A), A66.1 (B), WU2 (C), and TIGR4 (D) cells in either a sepsis or pneumonia model. Dotted line represents limit of detection for bacterial counts; ***$P<0.001$. For (A), (B), (C), and (D) in each set, the first group of dots from left represents Sham, and the second group of dots from left represents Consolidated. For each group of dots, thick bars indicate mean.
Figure 20:
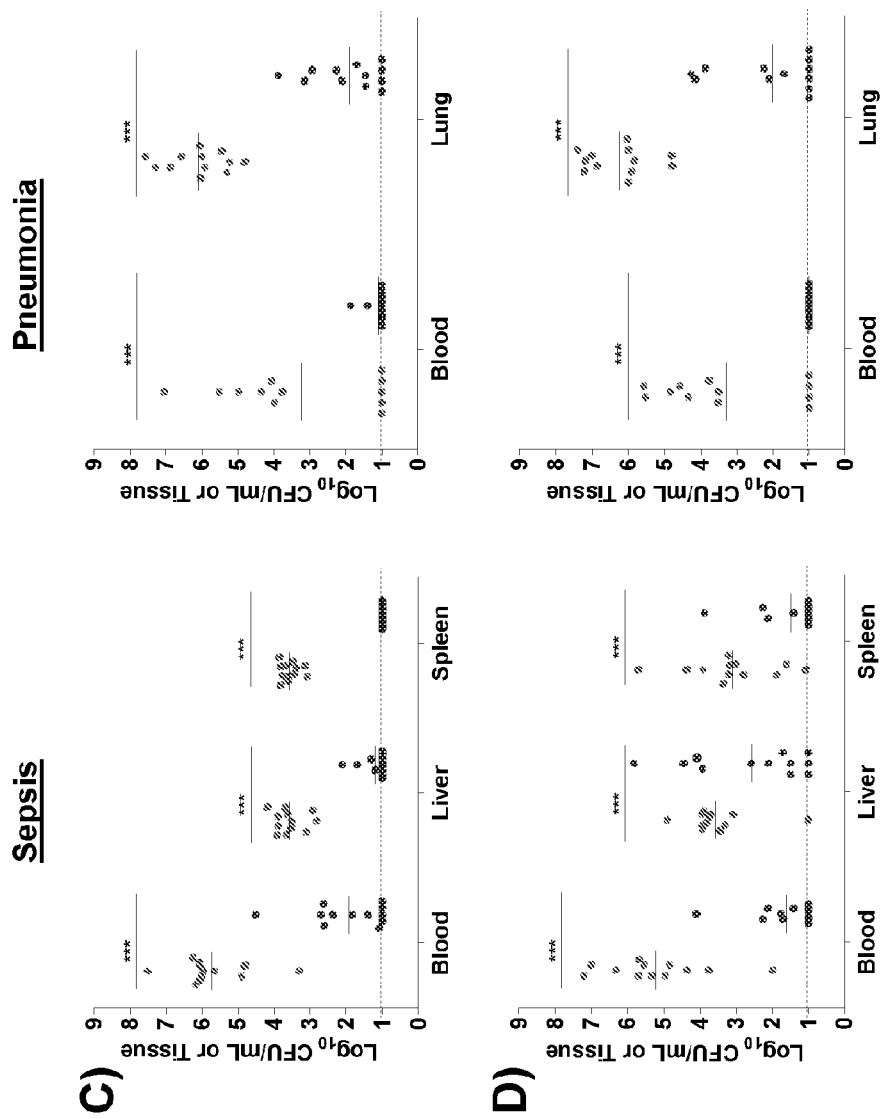

Strain D39 challenge was tested up to $10^{10}$ cells (FIG. 19) with strong protection (>80% survival) observed for the $10^7$ inoculum and varying degrees of protection provided beyond this level across administration routs. Protection conferred at these advanced challenge levels is considered impressive and highlights the combined adjuvant, delivery, and antigen consolidation capabilities of the hybrid vector. Furthermore, as supported by the data of FIG. 16, even better levels of protection would be expected with increased doses of the hybrid vector, readily possible as a result of engineering the degree of vector attenuation.

Finally, to further assess the protective capabilities of the antigens delivered with the hybrid vector, vaccination was tested against an extended panel of *S. pneumoniae* strains representing diverse serotypes notably difficult to protect against with current vaccine formulations; complete protection and reduced bacterial burden were observed (FIGS. 11G&H and 20).

Directed Protection and Expanded Strain Coverage

Figure 13:
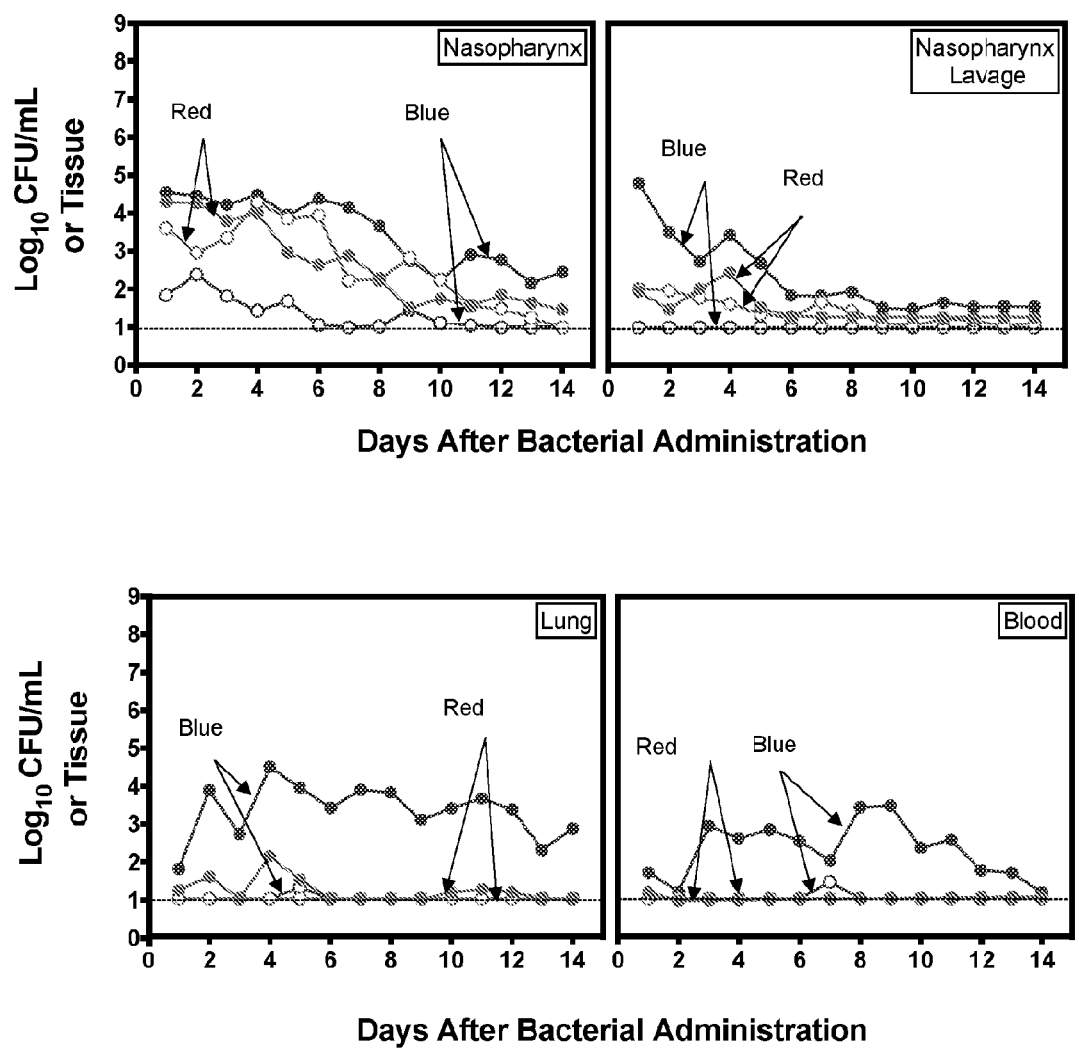
FIG. 13. Directed and extended protection using the hybrid vector. Assessment of bacterial burden was conducted across anatomical sites for unimmunized (filled circles) and immunized (using the consolidated antigens; open circles) mice challenged with avirulent (planktonic; red) or virulent (biofilm-released; blue) *S. pneumoniae* strain EF3030. Site-specific bacterial burden and protection was also tested over time for mice colonized with *S. pneumoniae* strain EF3030 and triggered for virulence progression using influenza A virus (IAV) inoculation (B, C, and D). Protection assessment was then extended to 10 additional clinically-relevant *S. pneumoniae* strains (E). Dotted line represents limit of detection for bacterial counts; ***$P<0.001$. For (B), (C), and (E) in each set, the first group of dots from left represents Sham, and the second group of dots from left represents Consolidated. In B, C, and E, for each group of dots, thick bars indicate mean.
Figure 13:
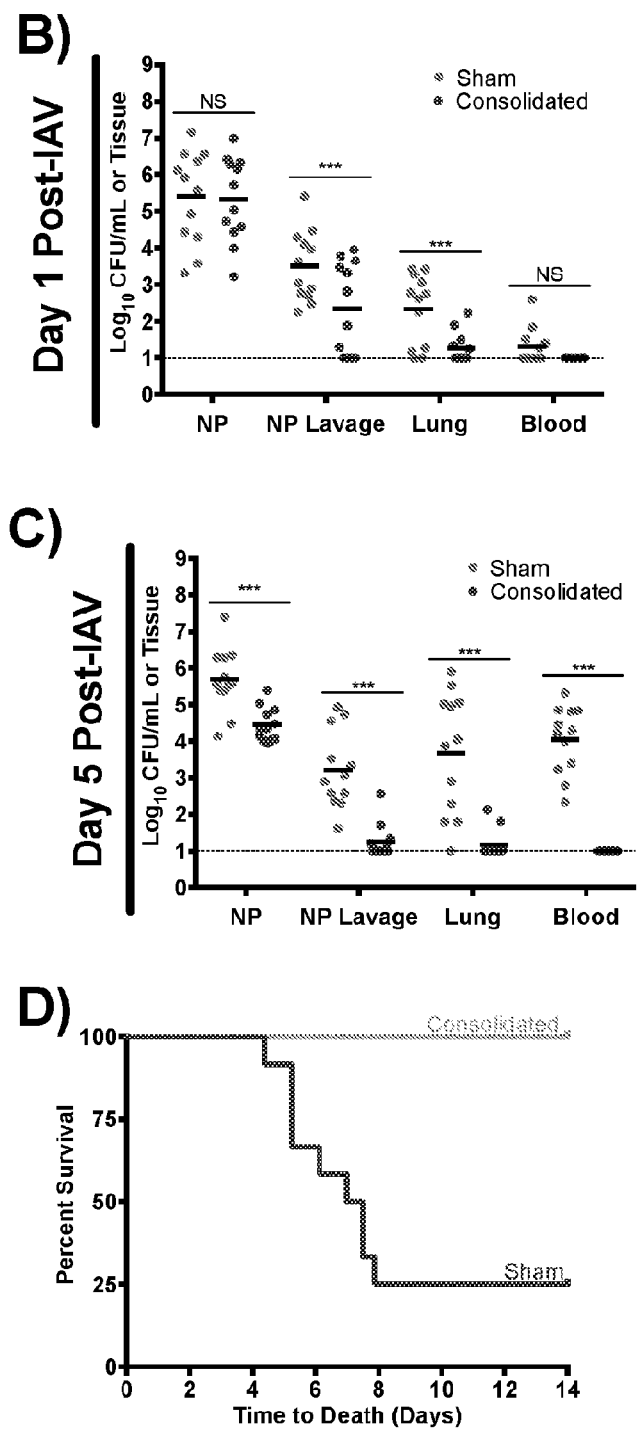
Figure 13:
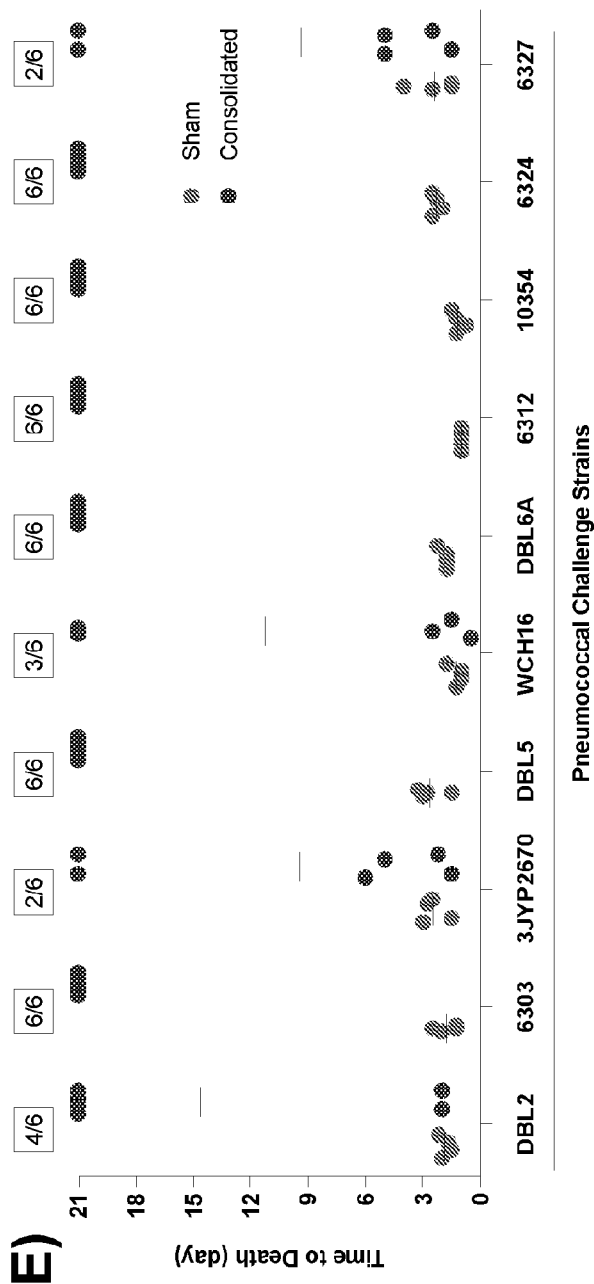
Figure 14:
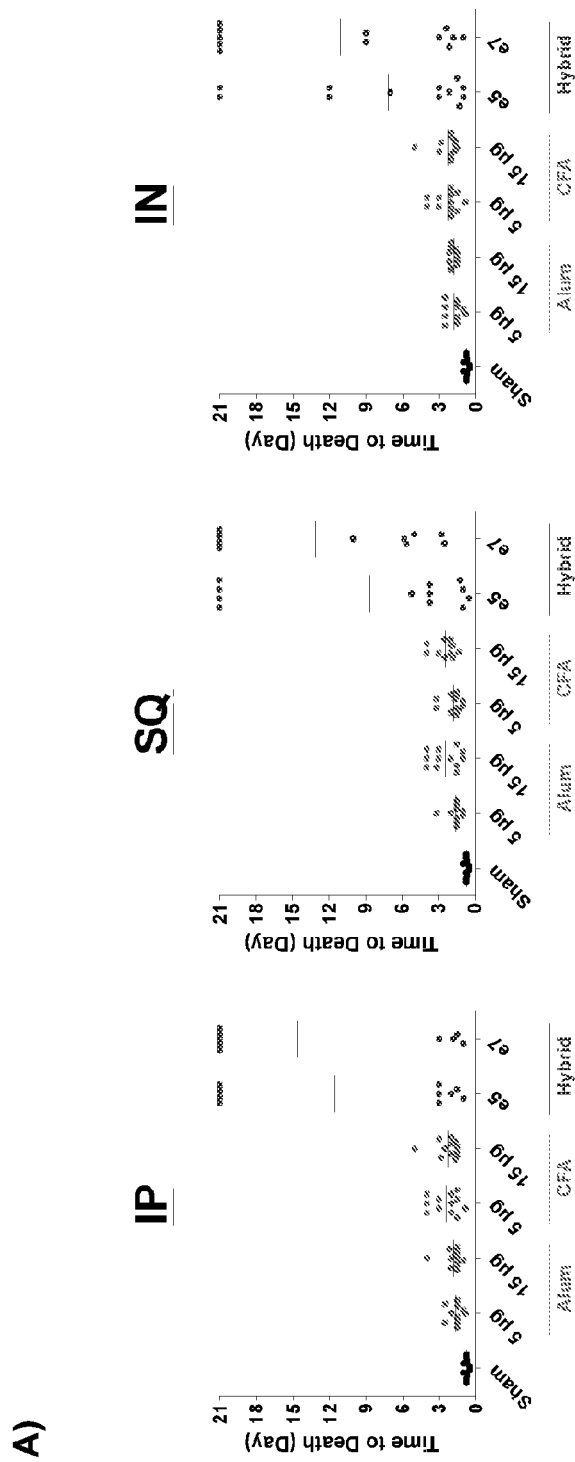
FIG. 14. Comparative assessment of vaccine outcomes across different formulations and administration routes with PspA. The hybrid vector housing PspA (via expression plasmid) is compared to protein formulations with either alum or complete Freund's adjuvant (CFA) and tested across intraperitoneal (IP), subcutaneous (SQ), and intranasal (IN) administration routes using sepsis (A) or pneumonia (B) mouse models challenged with *S. pneumoniae* strain D39. Similarly, antibody titres are compared (C). ***$P<0.001$ relative to controls on associated days. In A, and B, for each group of dots, thick bars indicate mean.
Figure 14:
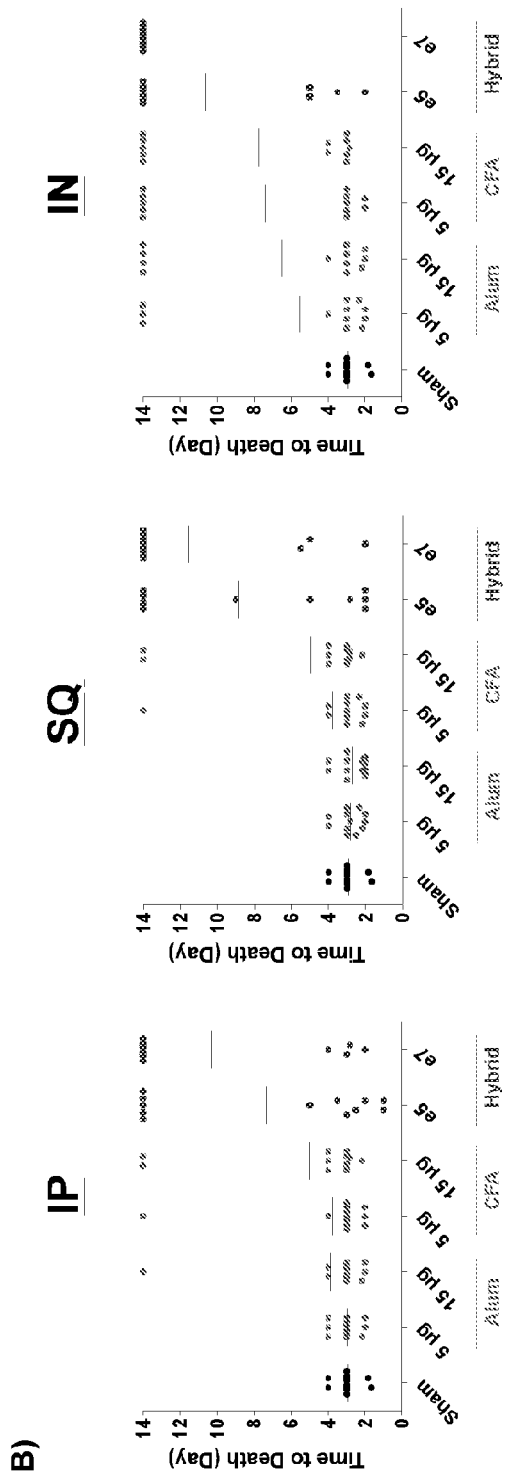
Figure 14:
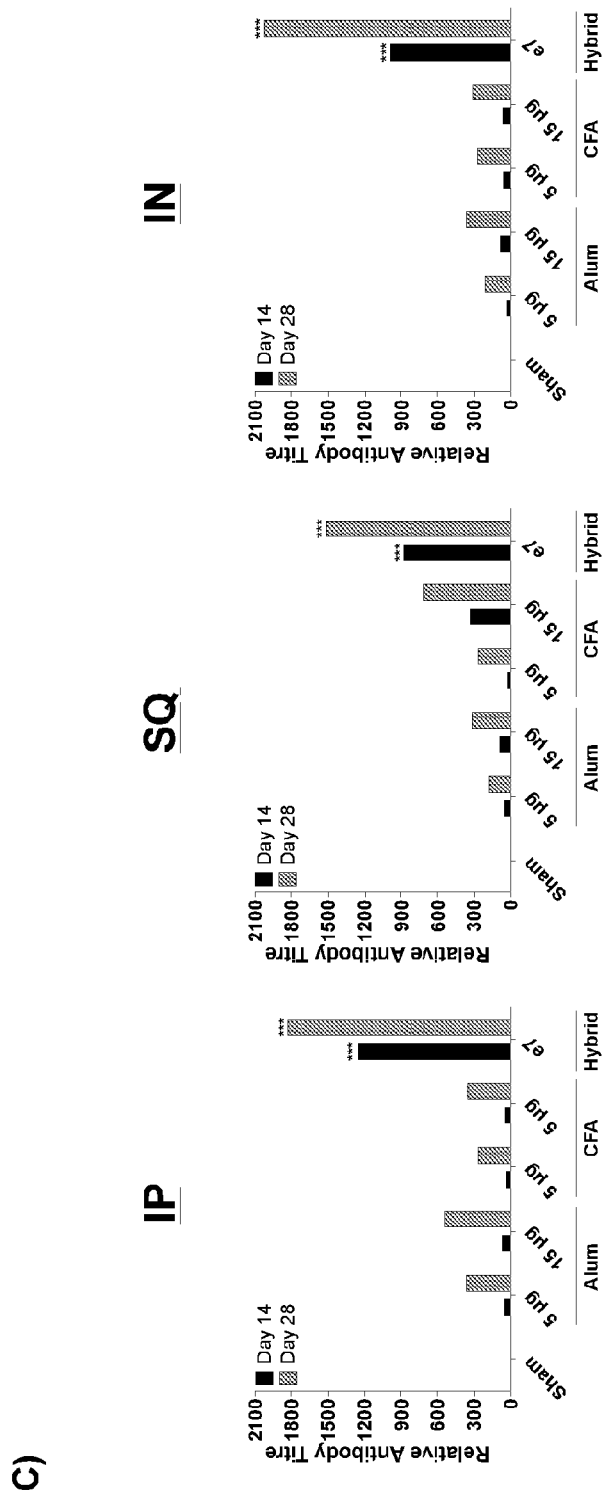

The directed nature of the vaccination strategy was tested first by comparing vaccinated and non-vaccinated mice subjects with avirulent and virulent *S. pneumoniae* strains (FIG. 13A). In these experiments, *S. pneumoniae* strain EF3030 was used due to planktonic (or broth cultured) cells demonstrating an avirulent phenotype; whereas, those cells released from in vitro or in vivo biofilms are virulent and cause disease (FIG. 12). The avirulent strains are cleared either with or without vaccination; whereas, only vaccinated mice are capable of demonstrating virulent bacterial clearance over time. This effect is further tested in the context of *S. pneumoniae* colonization followed by the addition of an in vivo virulence trigger (administration of influenza A virus [IAV]). Designed to more closely mimic the common clinical setting where influenza spurs pneumonia development, results indicate that bacterial dissemination is significantly reduced over time, in line with the theme of the immune response targeting only virulent populations, while complete protection is maintained with the consolidated set of antigens tested (FIGS. 13B,C,&D).

The consolidated aspect of the vaccine formulation also offers extended protection. Namely, the conserved nature of the individual antigens (Table 4), when presented in combination, provides the potential to cover a broad range of *S. pneumoniae* strains (Table 2). Extended protection was thus tested against a series of 10 additional *S. pneumoniae* strains with protection enhancement observed in all cases and complete protection provided in six cases (FIG. 13E).

Predicting Protection Potential

Figure 21:
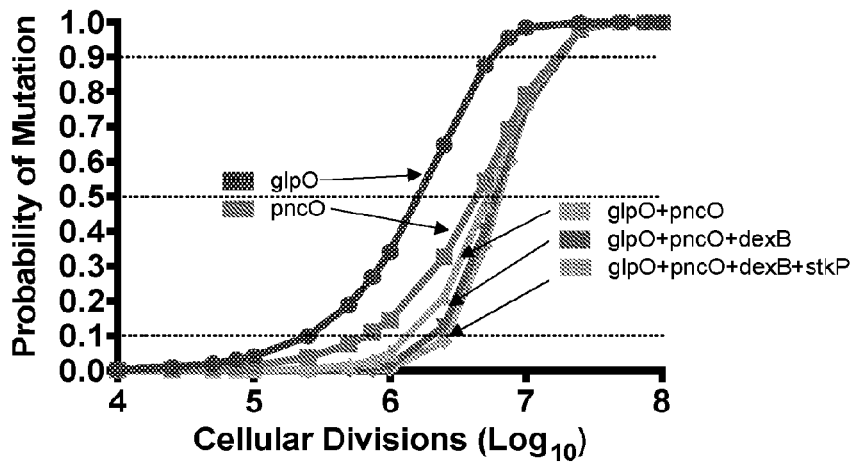
FIG. 21. Probability of mutations occurring in *S. pneumoniae* genes (glpO, pncO, dexB, and stkP) through cellular division. Probability of at least one mutation simultaneously occurring in glpO, pncO; glpO and pncO; glpO, pncO, and dexB; and glpO, pncO, dexB, and stkP over $10^8$ cellular divisions (A). Critical number of cellular divisions required to achieve a 10%, 50%, and 90% probability that at least one mutation will occur in each gene (B). A rate of $4.8×10^{-4}$ beneficial mutations per genome per duplication and a genome size of 2.1 Mbp were used in these calculations. In (B), for each set, bars from left to right are glpO, pncO, glpO+pncO, glpO+pncO+dexB, and glpO+pncO+dexB+stkP.
Figure 21:
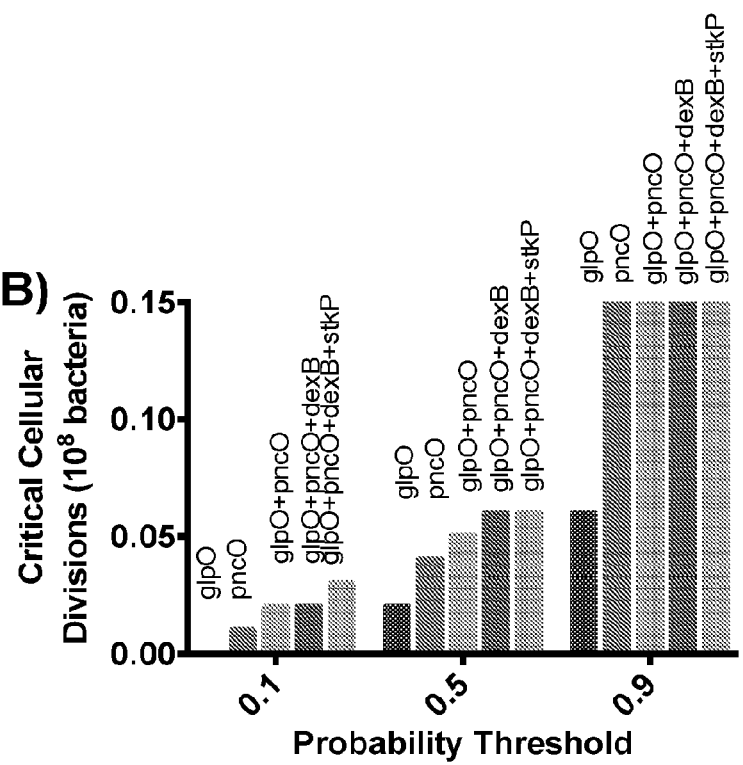

Though data presented support the broad protection potential of the consolidated antigens generated and delivered within the hybrid vector, the mutational potential of individual and combined antigens was predicted to further assess wide-spread and extended utilization of the vaccination strategy (FIG. 21). The results emphasize the cumulative resistance to mutation of the combined antigen vaccination strategy. Taken together, utilizing five antigens specific to virulence provides ample coverage and resistance to strain evasion. Thus, antigenic drift, as a result of innate *S. pneumoniae* mutation, and the associated threat to vaccine efficacy is minimized through consolidation.

Materials and Methods

Experimental Design.

A hybrid biological-biomaterial vector was tested in the delivery of virulent-specific antigens targeting pneumococcal disease progression. Success was assessed by mouse model immune response outcomes that included balanced antibody profiles, a directed targeting of virulent *S. pneumoniae* cells, reduced bacterial dissemination and tissue burden, and challenge protection. The hybrid vector allowed innate (or in situ) maintenance, consolidation, and production of the antigens in addition to other features that span vaccine production and enhanced delivery capability.

This study was carried out in strict accordance with the recommendations in the *Guide for the Care and Use of Laboratory Animals* of the National Institutes of Health. The protocols were approved by the Institutional Animal Care and Use Committee at the University at Buffalo, Buffalo, N.Y. All bacterial inoculations and treatments were performed under conditions designed to minimize any potential suffering of the animals.

Materials.

Bacterial and cell culture media and reagents were purchased from Fisher Chemical and Sigma-Aldrich (St. Louis, Mo.). Chemically defined bacterial growth medium (CDM) was obtained from JRH Biosciences, Lexera, Kans. Sheep blood was purchased from Hemostat Laboratories (Dixon, Calif.). Monomers were purchased from Sigma-Aldrich (St. Louis, Mo.) and TCI (Portland, Oreg.). Acetone (HPLC), chloroform (HPLC), n-hexadecane (99%), DMF (HPLC), and DMSO (≥99.7%) were purchased from Fisher Chemical. Phosphate buffered saline (PBS) was purchased from Life Technologies (Grand Island, N.Y.). All remaining chemicals and reagents were purchased from Sigma-Aldrich.

Polymer Synthesis.

Figure 22:
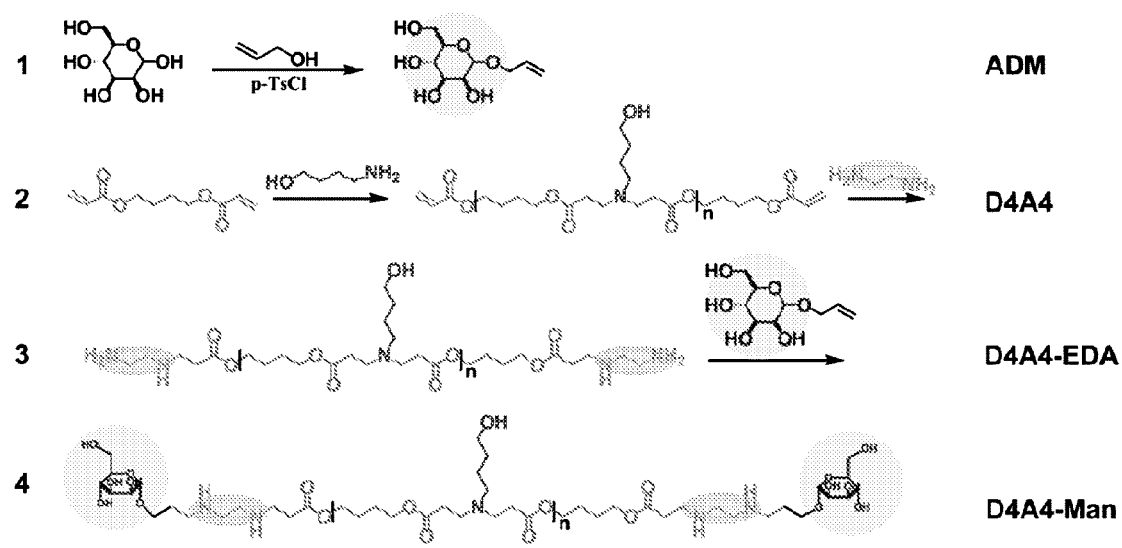
FIG. 22. Synthetic scheme for poly(beta-amino ester) D4A4-Man. Once generated, D4A4-Man was used as the coating of the hybrid vector.
Figure 23:
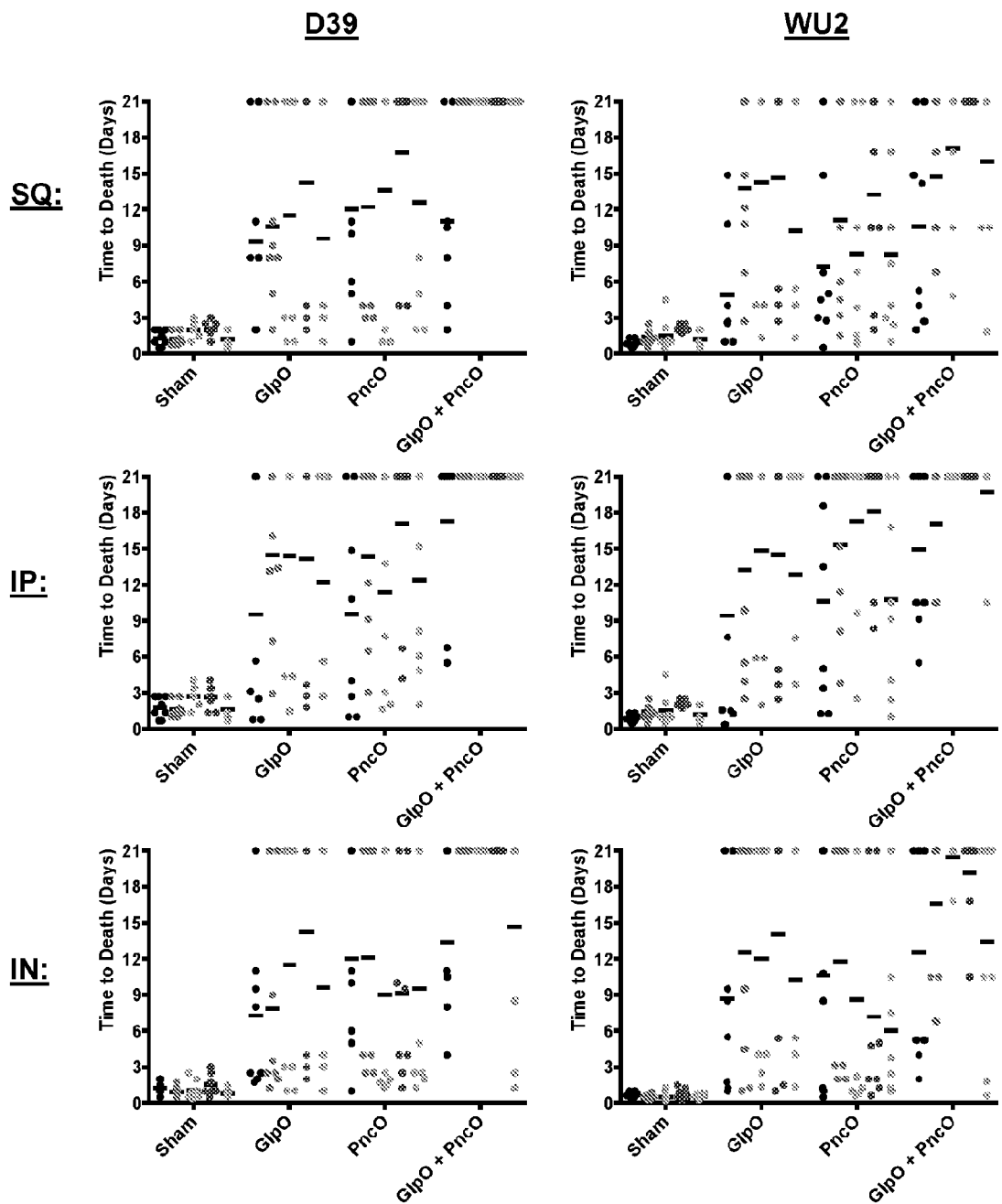
FIG. 23. Protection summary of vaccination strategies in a sepsis model. Various combinations of adjuvants (Alum, Fruends Adjuvant, Co-PoP containing MPLA, and Co-PoP containing CRM197) and antigens (GlpO, PncO, and GlpO+PncO) were administered across three delivery routes (SQ, IP, and IN). For each plot in this figure, the dots in each set from left to right are: Protein Alone, Alum, CFA/IFA, Co-PoP:MPLA, CO-PoP:CRM197. For each group of dots, thick bars indicate mean.
Figure 23:
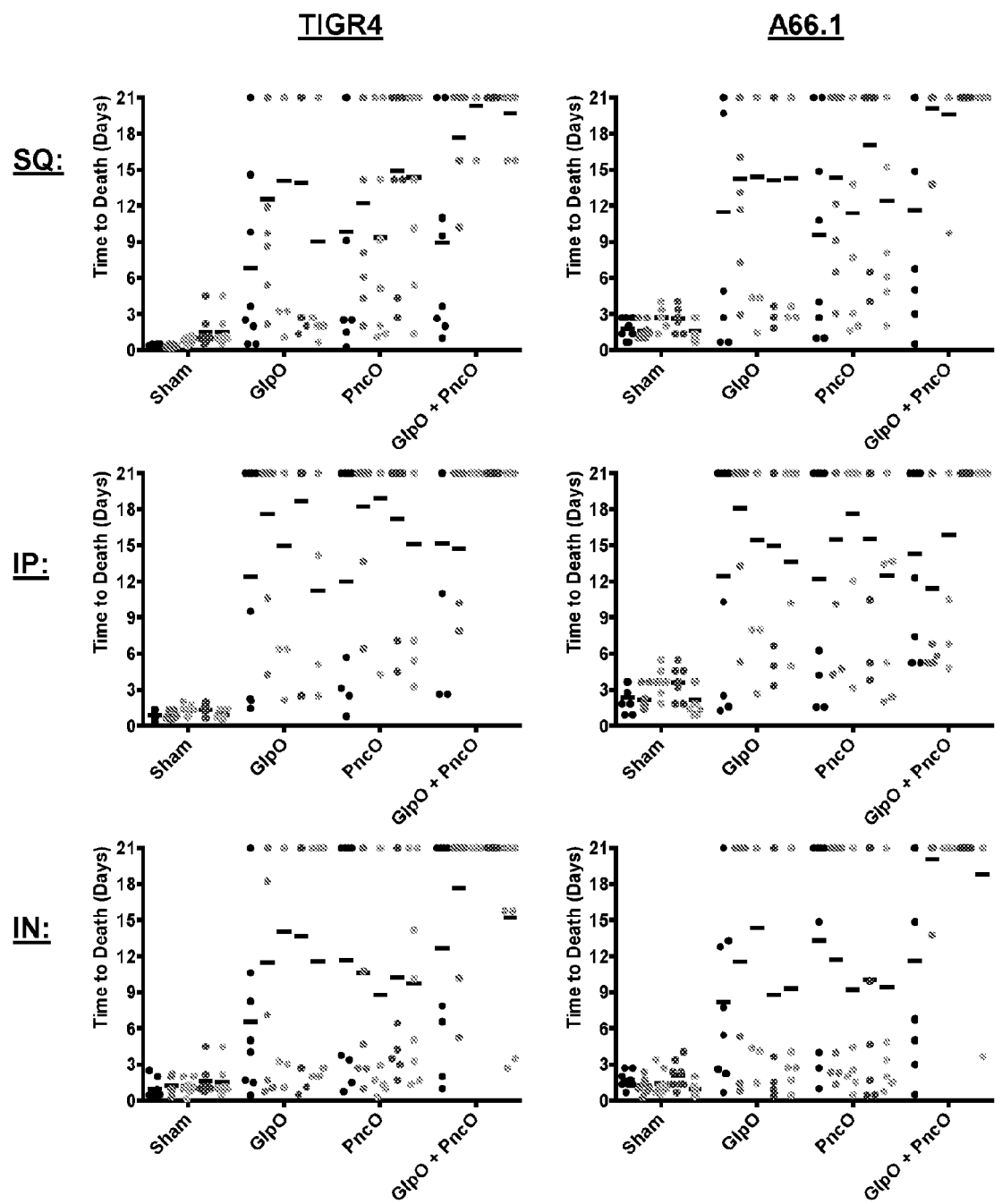
Figure 24:
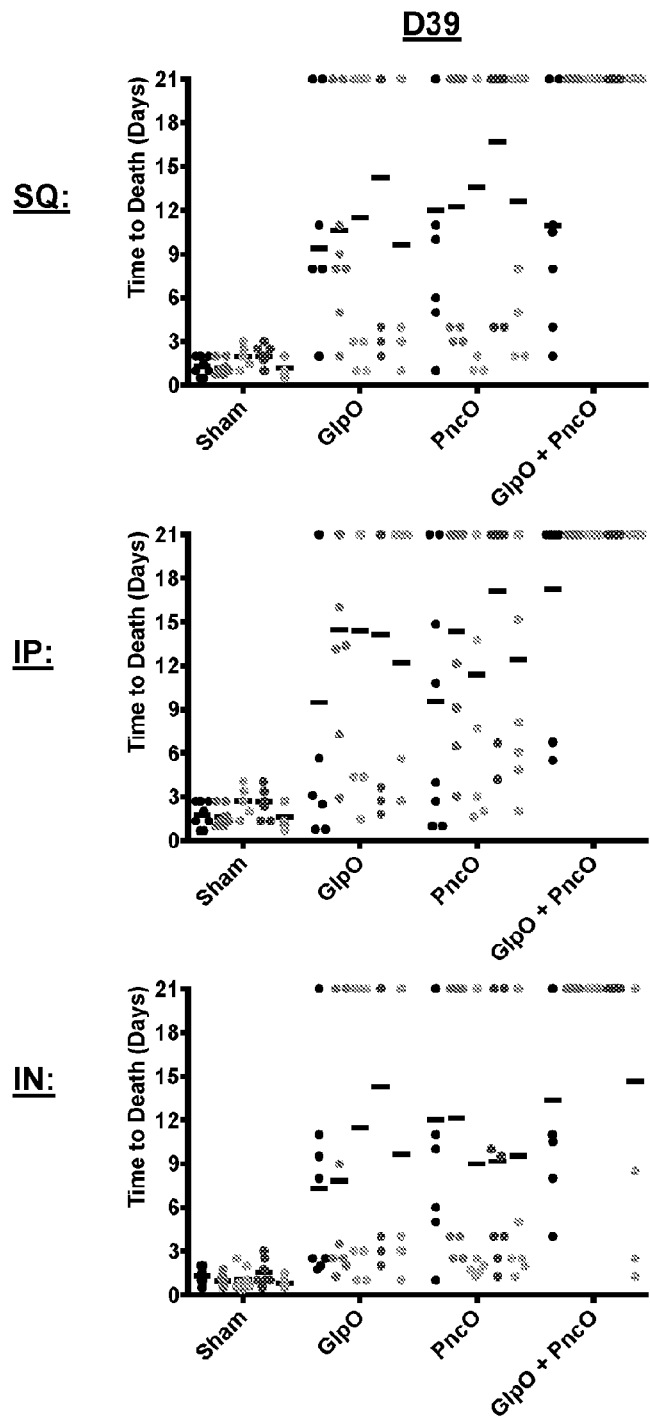
FIG. 24. Protection summary utilizing a D39 sepsis challenge model. For each plot in this figure, the dots in each set from left to right are: Protein Alone, Alum, CFA/IFA, Co-PoP:MPLA, CO-PoP:CRM197. For each group of dots, thick bars indicate mean. For each group of dots, thick bars indicate mean.
Figure 25:
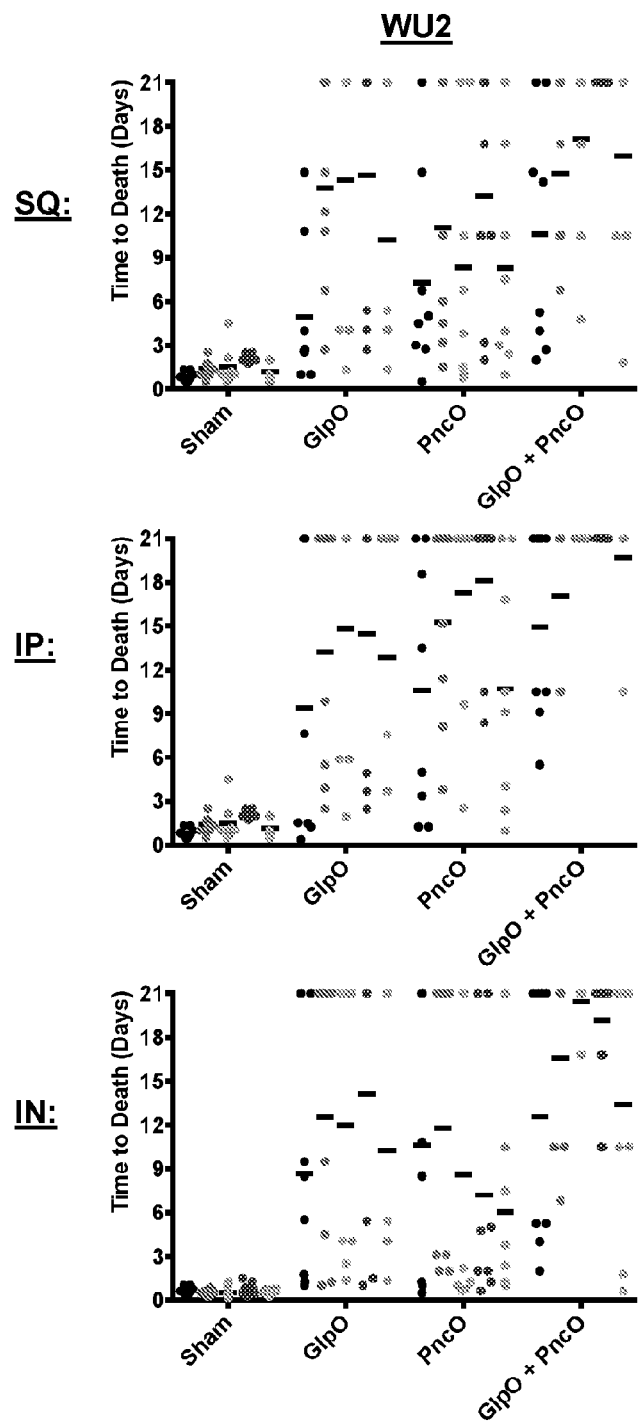
FIG. 25. Protection summary utilizing a WU2 sepsis challenge model. For each plot in this figure, the dots in each set from left to right are: Protein Alone, Alum, CFA/IFA, Co-PoP:MPLA, CO-PoP:CRM197. For each group of dots, thick bars indicate mean.
Figure 26:
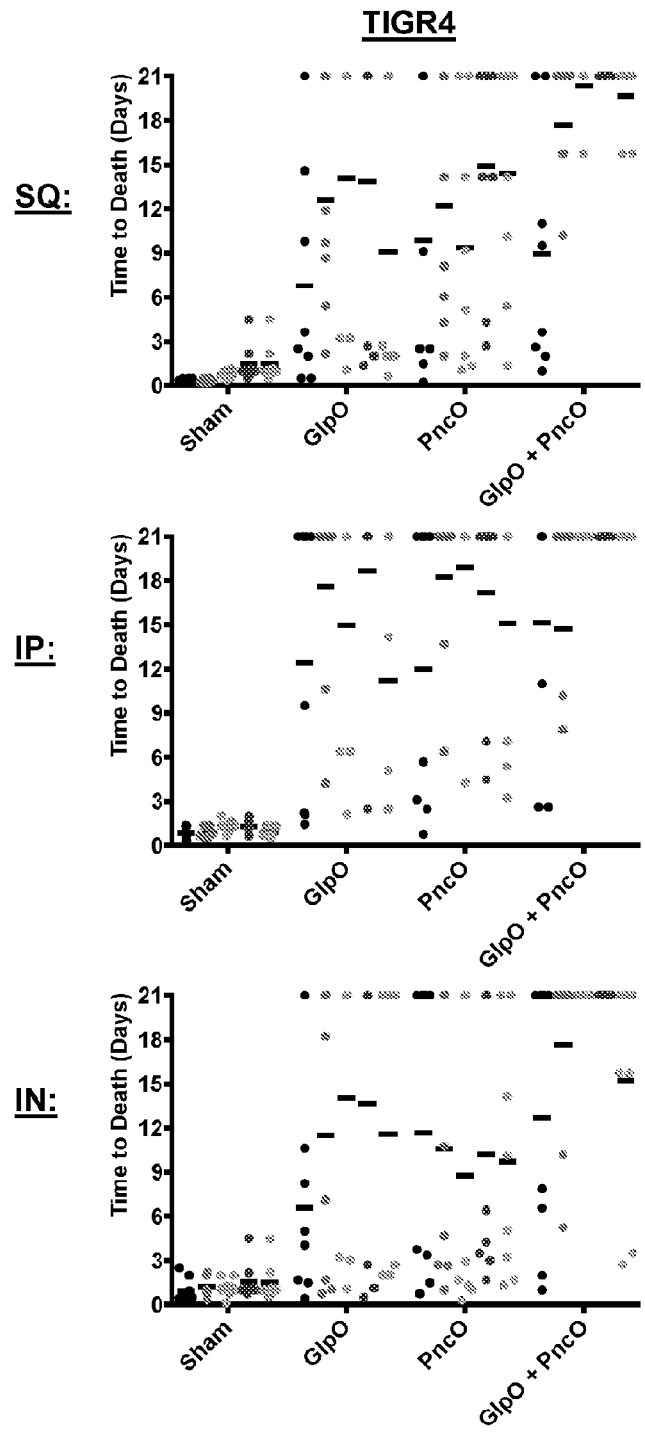
FIG. 26. Protection summary utilizing a TIGR4 sepsis challenge model. For each plot in this figure, the dots in each set from left to right are: Protein Alone, Alum, CFA/IFA, Co-PoP:MPLA, CO-PoP:CRM197. For each group of dots, thick bars indicate mean.
Figure 27:
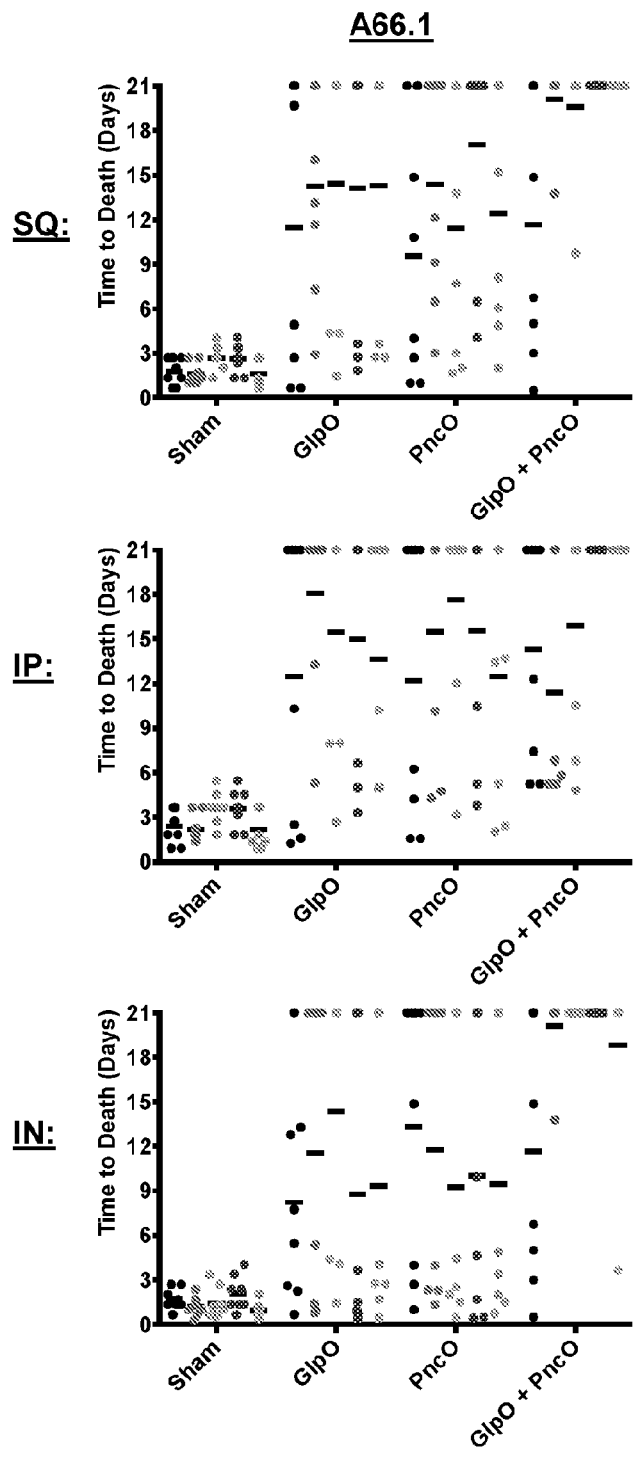
FIG. 27. Protection summary utilizing a A66.1 sepsis challenge model. For each plot in this figure, the dots in each set from left to right are: Protein Alone, Alum, CFA/IFA, Co-PoP:MPLA, CO-PoP:CRM197. For each group of dots, thick bars indicate mean.

The polymer used in this study, D4A4-Man, was synthesized in a four-step reaction (FIG. 22). Briefly, in step 1, allyl-α-D-mannopyranoside (ADM) was synthesized by dissolving 3 g of D-(+)-mannose and 18 mg p-TsCl in allyl alcohol (20 mL) at 90° C. under reflux for 24 h. The resulting reaction solution was concentrated by vacuum distillation at 35° C. Next, in step 2, acrylate-terminated D4A4 was synthesized in DMSO at a 1:1.2 amine/diacrylate molar ratio for 5 days at 60° C. with continuous stirring at 1,000 rpm. Acrylate-terminated polymers were purified by dialysis followed by evaporation under vacuum. Dialysis procedures were conducted against acetone using molecular porous membrane tubing (Spectra/Por Dialysis Membrane, Spectrum Laboratories Inc.) with an approximate molecular weight cut-off at 3,500 Da. In step 3, acrylate-terminated D4A4 was reacted with excess ethylenediamine to amine-cap the terminal ends (D4A4-EDA). Specifically, acrylate-terminated D4A4 was dissolved in DMSO at 167 mg/mL and reacted with 5 M ethylenediamine (in DMSO) at room temperature for 24 h. D4A4-EDA was purified by dialysis followed by evaporation under vacuum. In the last step, D4A4-EDA was reacted with ADM at a 1:2 molar ratio in DMSO at 90° C. for 24 h and then purified via dialysis. Structure and purity of D4A4-Man were confirmed using $^1$H NMR spectroscopy.

Bacterial Strains and Plasmid Generation.

Antigen genes were amplified from the genomic DNA of *S. pneumoniae* strains using primers summarized in Table S2. Each PCR product was cloned into pET expression plasmids using the flanking restriction sites indicated (designed within the primers). Constructs were verified by colony PCR and restriction digest analysis and were then chemically transformed into the BL21(DE3) *E. coli* cell line (Novagen). Resulting single-colony transformants were cultured in 3 mL lysogeny broth (LB) at 37° C. with shaking prior to 15% glycerol stock storage at −80° C. Plasmid selection antibiotics were used as needed during bacterial culture within LB medium. Expression was confirmed by 3-5 mL LB cultures started from glycerol stocks and grown at 37° C. with shaking until an OD$_{600}$ of 0.4 was achieved. After which, cultures were induced with isopropyl β-D-1-thiogalactopyranoside (IPTG) (1 mM) for 1 hour. Upon collection via centrifugation, cells were washed twice with PBS and resuspended in 25 mM Tris-HCL prior to boiling with loading dye and expression analysis/confirmation via SDS-PAGE. Plasmid pUAB055 was used to express and clone the pspA gene.

Figure 18:
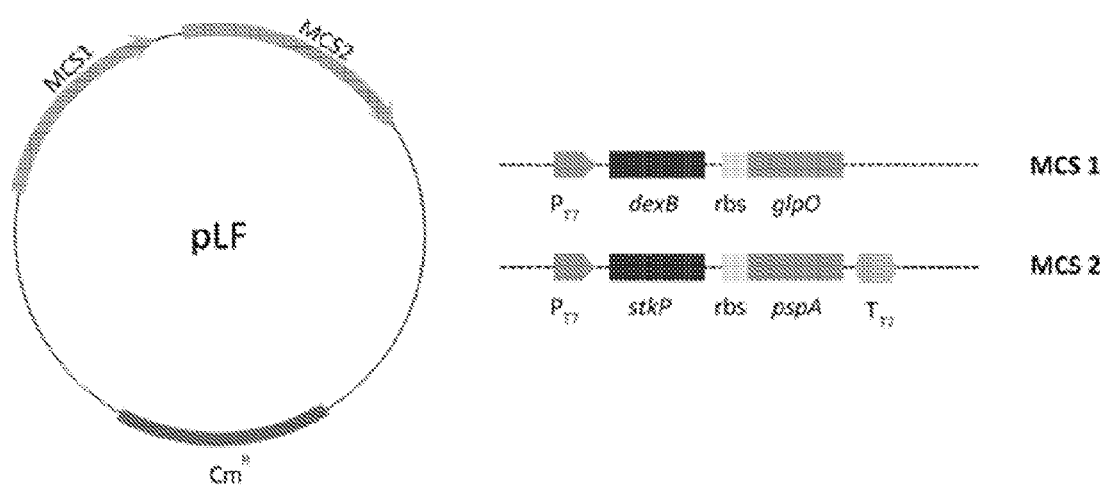
FIG. 18. The pLF consolidation design and organization. MCS: multiple cloning site; $Cm^R$: chloramphenicol resistance; $P_{T7}$: T7 promoter; rbs: ribosomal binding site; $T_{T7}$: T7 terminator.

To employ the two-plasmid system, pCJ10 was used in conjunction with a plasmid containing pspA, dexB, stkP, and glpO. The consolidated plasmid was assembled by subcloning each respective gene into a pACYCDuet-1 plasmid (FIG. 18 and Table 5). To construct pLF, the restriction enzymes/sites were utilized for the corresponding multiple cloning sites (MCSs) within pACYCDuet-1. Plasmids were chemically transformed into *E. coli* strain BL21(DE3) (as the basis for hybrid device preparation) and resulting transformants prepared and stored as glycerol stocks.

Hybrid Device Preparation.

Bacterial and hybrid vectors were prepared from bacterial cultures inoculated at 2% (vol/vol) from overnight starter cultures. Following incubation at 37° C. with shaking until 0.4-0.5 $OD_{600}$, samples were induced with 0.1 mM IPTG at 30° C. for 3 h. Bacterial vectors were then washed once and standardized to 0.5 $OD_{600}$ in PBS; whereas, bacteria to be used in hybrid vector formation were washed once and standardized to 1.0 $OD_{600}$ in 25 mM NaOAc (pH 5.15). Polymer was dissolved in chloroform, desiccated, and resuspended at 1 mg/mL in 25 mM NaOAc (pH 5.15) before being added in an equal volume to bacteria and mixed by vortexing on setting 5 (Analog Vortex Mixer; Fisher Scientific) for 10 s. Polymer/bacteria self-assembly was allowed to continue for 15 min, and devices were then diluted in PBS.

Hybrid Vaccine Immunization.

Outbred 6-week-old female CD-1 mice (Harlan Laboratories, Indianapolis, Ind.) were used in immunization experiments. Mice were immunized by IP injection (200 µL), SQ injection (200 µL), and IN aspiration (40 µL) using isoflurane; unless indicated otherwise, $10^7$ hybrid vectors were used in vaccination experiments. Immunization of controls included sham (PBS; all samples were prepared in PBS as the background solution); PspA plus alum; and PspA plus complete Freund's adjuvant (CFA), which was replaced with Incomplete Freund's Adjuvant (IFA) during booster immunizations. After 14 days, mice were boosted with the same formulations except in the case of the CFA adjuvant as noted above. At days 14 and 21, samples were collected by retro-orbital bleeding and clarified by centrifugation to collect serum.

S. pneumoniae Bacterial Preparation and Biofilm Release.

S. pneumoniae strains used in this study are listed in Table 6 and were initially grown on Todd-Hewitt agar plates supplemented with 0.5% yeast extract and 5% sheep blood and incubated overnight at 37° C. Single colonies were used to inoculate 5 mL Todd-Hewitt broth containing 0.5% yeast extract and incubated at 37° C. to an $OD_{600}$ of 0.6. At this point, S. pneumoniae strains used for challenge studies were washed one time with and resuspending in PBS. NCI-H292 epithelial cells were cultured in RPMI-1640 medium in T75 flasks at 37° C. and 5% $CO_2$. After reaching 100% confluency, H292 cells were prefixed in 4% buffered paraformaldehyde at 34° C. for 48 hours followed by three washes with PBS. CDM-grown pneumococci were then seeded onto fixed H292 cells with change of media occurring every 12 hours. Formed biofilms were exposed to heat (38.5° C.) for 4 hours and released cells were then collected by centrifugation, washed and resuspended in PBS, and quantified by $OD_{600}$ measurement. Strains presented in Table 6 are a mix of mouse-passaged strains, which directly confer virulence upon culture and administration, and clinical isolates, which usually do not cause disease upon direct administration and require heat release from the in vitro biofilm model (detailed directly above) to render a virulent phenotype.

Challenge Models.

To induce sepsis or pneumonia, mice were administered IP or IN (with isoflurane), respectively, with $1 \times 10^4$ to $1 \times 10^{10}$ CFU of pneumococci strains (Table 6). To induce colonization, mice were administered $1 \times 10^6$ CFU bacteria IN without isoflurane. To mimic influenza-induced pneumonia, pneumococci colonization was followed by intranasal inoculation with 40 plaque forming units of IAV. A mouse-adapted IAV strain A/PR/8/34 (H1N1) (ATCC VR-95) was used, and titers were determined by plaque assays. Mice were monitored every four hours for signs of morbidity (huddling, ruffled fur, lethargy, and abdominal surface temperature). Mice found to be moribund were euthanized via $CO_2$ asphyxiation and cervical dislocation.

Tissue Bacterial Count.

At predefined time points (24 and 48 h post-infection for IP and IN challenges, respectively) or upon becoming moribund, mice were euthanized (as described above) and a combination of nasopharynx tissue, nasopharyngeal lavage fluid, lung, liver, spleen, and blood samples was collected and bacterial burden determined. Briefly, tissue and organ homogenate, lavage fluid, and blood were homogenized to ensure dissociation of bacterial aggregates and then serially diluted on tryptic soy and 5% blood agar plates prior to enumeration.

Histology Analysis.

Following induction of isoflurane anesthesia, a midline abdominal incision was made and the abdominal aorta transected to exsanguinate and euthanize the animal. A midline incision was continued through the thoracic cavity and neck to allow injection of 5 mL normal saline into the right ventricle of the heart to flush the pulmonary vasculature of residual blood. A luer-lock hubbed 20 ga×½" cannula was inserted into the trachea and secured in place with a suture. The lungs were fixed by insulflation with 10% neutral buffered formalin at 20 $cmH_2O$ for 24 h at room temperature. The lung lobes were removed, embedded in paraffin, and 5 µm tissue slices were prepared and stained with hematoxylin and eosin by standard histopathology techniques. Histology images were acquired with an Aperio ScanScope CS slide scanner (Leica Biosystems, Buffalo Grove, Ill.) using a 40× objective lens and subsequently analyzed using Aperio ImageScope software (v.12.3 Leica Biosystems).

Antibody Analysis.

To characterize antibody titers associated with delivery optimization, an enzyme-linked immunosorbent assay (ELISA) was performed by coating a 96-well Costar high binding polystyrene plate with 10 µg/mL PspA in tris-buffered saline (TBS) at 4° C. overnight. The plate was blocked with 3% BSA in TBS-Tween 20 (TBS-T) for one hour at 22° C. Sera was diluted into TBS-T in ratios of 1:1,000, 1:5,000, 1:7,500 and 1:10,000 and added to the plate. The plates were then incubated at 37° C. with mild agitation for three hours. The secondary antibody (Anti-Mouse IgG, IgA, IgM (H+L), IgE, Highly X-Adsorbed-Biotin) was added to the wells in a 1:1,000 ratio and agitated for two hours. Streptavidin was added to each well in a 1:1,000 ratio and allowed to shake for 30 minutes. The signal was developed with p-nitrophenyl phosphate and the reaction was quenched using 0.75 M NaOH. The signal was detected using a plate reader spectrophotometer at an absorbance of 405 nm.

Statistical Analysis.

Column comparisons were analyzed for statistical significance using a two-tailed Student t test for unpaired data. Multivariance analysis was done using one-way analysis of variance (ANOVA) that was corrected using the Bartlett variance test and for multiple comparisons using the Bonferroni multiple-comparison test. For both tests, a P value of 0.05 was considered significant. Statistical analysis was performed using the GraphPad Prism software (version 6.0h.283; GraphPad Software Inc., La Jolla, Calif.). All data resulted from animal experiments using six to twelve subjects per group except histology analysis, which utilized two mouse subjects per group.

Example 3

This example provides additional data describing PncO and GlpO utilized in an expanded sepsis model. Results are shown in FIGS. 23-27. In this example, adjuvant components were added to the GlpO and PncO protein antigens and testing was carried out as described in the above examples. Across the adjuvants tested with GlpO and PncO, there is generally a similar trend of vaccination effectiveness (measured as protection against disease challenge).

The invention claimed is:

1. A method of eliciting an immune response in an individual against streptococcal infection comprising administering to the individual an effective amount of a composition comprising an immunologically effective amount of an isolated PncO polypeptide having a sequence of SEQ ID NO: 1, or having at least 90% homology to SEQ ID NO: 1, in a pharmaceutical carrier, wherein the polypeptide in the composition is incorporated into a nanovesicle, and wherein the nanovesicle comprises porphyrin phospholipid conjugates having cobalt chelated thereto.

2. The method of claim 1, wherein the elicited immune response is protective against an infection caused by S. pneumoniae.

3. The method of claim 2, wherein the infection caused by S. pneumonia is pneumonia.

4. The method of claim 1, wherein the polypeptide in the composition is incorporated into a hybrid biological delivery vehicle.

5. The method of claim 1, wherein the composition comprises an adjuvant.

6. The method of claim 1, wherein the nanovesicle has an adjuvant incorporated therein.

7. The method of claim 4, wherein the hybrid delivery vehicle has an adjuvant incorporated therein.

8. The method of claim 1, wherein the method further comprises administering a polypeptide GlpO having a sequence of SEQ ID NO:2 or having a sequence which has at least 90% homology to SEQ ID NO:2.

9. The method of claim 8, wherein the polypeptide polypeptide GlpO having a sequence of SEQ ID NO:2 or having a sequence which has at least 90% homology to SEQ ID NO:2 and the polypeptide PncO having a sequence of SEQ ID NO:1 or having a sequence which is at least 90% homology to SEQ ID NO:1 are administered in the same composition.

10. The method of claim 8, wherein the polypeptide GlpO having a sequence of SEQ ID NO:2 or having a sequence which has at least 90% homology to SEQ ID NO:2 and the polypeptide PncO having a sequence of SEQ ID NO:1 or having a sequence which has at least 90% homology to SEQ ID NO:1 are administered in separate compositions.

* * * * *